(12) United States Patent
El-Shafie

(10) Patent No.: US 10,179,922 B2
(45) Date of Patent: Jan. 15, 2019

(54) METHOD AND SYSTEM FOR PROCESSING A BIOMASS FOR PRODUCING BIOFUELS AND OTHER PRODUCTS

(71) Applicant: Moustafa Ahmed El-Shafie, Giza (EG)

(72) Inventor: Moustafa Ahmed El-Shafie, Giza (EG)

( * ) Notice: Subject to any disclaimer, the term of this patent is extended or adjusted under 35 U.S.C. 154(b) by 0 days.

(21) Appl. No.: 14/309,809

(22) Filed: Jun. 19, 2014

(65) Prior Publication Data

US 2014/0302570 A1    Oct. 9, 2014

Related U.S. Application Data

(63) Continuation of application No. 13/382,897, filed as application No. PCT/US2010/041441 on Jul. 8, 2010.
(Continued)

(51) Int. Cl.
| C02F 3/00 | (2006.01) |
| C02F 3/34 | (2006.01) |
| C11B 1/02 | (2006.01) |
| C11B 1/10 | (2006.01) |
| C12F 3/02 | (2006.01) |

(Continued)

(52) U.S. Cl.
CPC .............. *C12P 7/64* (2013.01); *A23K 10/12* (2016.05); *C02F 3/00* (2013.01); *C02F 3/34* (2013.01); *C11B 1/025* (2013.01); *C11B 1/10* (2013.01); *C12F 3/02* (2013.01); *C12M 47/06* (2013.01); *C12N 1/06* (2013.01); *C12P 3/00* (2013.01); *C12P 7/6409* (2013.01); *C12P 7/649* (2013.01); *C12P 7/6463* (2013.01);
(Continued)

(58) Field of Classification Search
CPC .. C12P 7/64; C12P 3/00; C12P 7/6409; C12P 7/6463; C12P 7/649; C12P 2201/00; A23K 1/007; C02F 3/00; C02F 3/34; C02F 2303/06; C02F 2305/14; C11B 1/025; C11B 1/10; C12F 3/02; C12M 47/06; C12N 1/06; Y02E 50/13
USPC .......................................................... 435/41
See application file for complete search history.

(56) References Cited

U.S. PATENT DOCUMENTS

| 3,089,821 A | 5/1963 | Folkers |
| 4,795,709 A | 1/1989 | Hopkins |

(Continued)

FOREIGN PATENT DOCUMENTS

| EP | 1538197 A1 * | 6/2005 | ........... C05G 3/0041 |
| WO | WO-2004002896 A1 * | 1/2004 | ............. A01N 63/00 |

OTHER PUBLICATIONS

EPA technical Manual (1999). Alternative Disinfectants and Oxidants Guidance Manual. Ch. 4: Chlorine Dioxide, p. 4-1 through p. 4-40 and Table of Contents.*

(Continued)

*Primary Examiner* — Sean C. Barron
(74) *Attorney, Agent, or Firm* — Seed IP Law Group LLP

(57) ABSTRACT

The present invention provides methods of processing a biomass, e.g., for producing lipid and non-lipid materials, by inducing autolysis of a biomass. The biomass may be generated using any species of microorganism and any available biodegradable substrate, including waste materials. The lipid and non-lipid materials are present in two separate layers of the autolysate, and they can be used to generate valuable products such as biofuels and nutritional supplements. The present invention further provides a processing apparatus useful for practicing the methods of the present invention.

14 Claims, 7 Drawing Sheets

Related U.S. Application Data

(60) Provisional application No. 61/223,995, filed on Jul. 8, 2009.

(51) Int. Cl.
  *C12M 1/00* (2006.01)
  *C12N 1/06* (2006.01)
  *C12P 3/00* (2006.01)
  *C12P 7/64* (2006.01)
  *A23K 10/12* (2016.01)

(52) U.S. Cl.
  CPC ...... *C02F 2303/06* (2013.01); *C02F 2305/14* (2013.01); *C12P 2201/00* (2013.01); *Y02E 50/13* (2013.01)

(56) References Cited

U.S. PATENT DOCUMENTS

| | | | | |
|---|---|---|---|---|
| 5,330,914 | A | * | 7/1994 | Uhlen ............... C12M 47/12 435/270 |
| 5,424,467 | A | | 6/1995 | Bam et al. |
| 6,166,231 | A | | 12/2000 | Hoeksema |
| 2002/0164731 | A1 | | 11/2002 | Eroma et al. |
| 2007/0178569 | A1 | | 8/2007 | Leschine et al. |
| 2008/0160593 | A1 | | 7/2008 | Oyler |
| 2008/0293132 | A1 | | 11/2008 | Goldman et al. |
| 2009/0064567 | A1 | | 3/2009 | Lippmeier et al. |
| 2009/0159538 | A1 | * | 6/2009 | Duve ............... A01N 59/00 210/754 |
| 2012/0122164 | A1 | | 5/2012 | El-Shafie | |

OTHER PUBLICATIONS

Van Maris et al. Alcoholic fermentation of carbon sources in biomass hydrolysates by *Saccharomyces cerevisiae*: current status. Antonie van Leeuwenhoek (2006), v90, p. 391-418.*
Teusink et al. Intracellular Glucose Concentration in Derepressed Yeast Cells Consuming Glucose Is High Enough to Reduce the Glucose Transport Rate by 50%. Journal of Bacteriology (1998), v183(3), p. 556-562.*
Meneghin et al. Chlorine Dioxide Against Bacteria and Yeasts From the Alcoholic Fermentation. Brazilian Journal of Microbiology (2008) 39:337-343. (Year: 2008).*
Annuar et al., "Evaluation of nitrogen sources for growth and production of medium-chain-length poly-(3-hydroxyalkanoates)from palm kernel oil by *Pseudomonas putida* PGA1," *Asia Pacific Journal of Molecular Biology and Biotechnology* 16(1): 11-15, 2008.
Benarde et al., "Kinetics and Mechanism of Bacterial Disinfection by Chlorine Dioxide," *Applied Microbiology* 15(2):257-265, 1967.
Breddam et al., "Acceleration of yeast autolysis by chemical methods for production of intracellular enzymes," *Applied Microbiology and Biotechnology* 35:323-329, 1991.
Collins Dictionary of Biology, "Alcoholic fermentation,"2005, retrieved from, URL=http://www.credoreference.com/enrty/collinsbiology/alcoholic_fermentation, download date May 20, 2013, 1 page.
Collins English Dictionary, "Autolysis," 2000, retrieved from, URL= http://www.credoreference.com/entry/hcengdict/autolysis, download date May 31, 2013, 1 page.
Dai et al., "Biodiesel generation from oleaginous yeast *Rhodotorula glutinis* with xylose assimilating capacity," *African Journal of Biotechnology* 6(18):2130-2134, 2007.
Dinnbier et al. "Transient accumulation of potatssium glutamate and its replacement by trehalose during adaptation of growing cells of *Escherichia coli* K-12 to elevated sodium chloride concentrations," *Archives of Microbiology* 150:348-357, 1988.
Leduc et al., "Autolysis of *Escherichia coli*," *Journal of Bacteriology* 142(1):52-59, 1980.
Leggett et al., "Anion Absorption by Baker's Yeast," *Plant Physiol* 39(3):387-390, 1964.
Ohta et al., "Genetic Improvement of *Escherichia coli* for Ethanol Production: Chromosomal Integration of *Zymomonas mobilis* Genes Encoding Pyruvate Decarboxylase and Alcohol Dehydrogenase II," *Applied and Environmental Microbiology* 57(4):893-900, 1991.
Ramírez-Orozco et al., "*Debaryomyces hansenii* growth in nonsterile seawater ClO$_2$-peptone-containing medium," *Can. J. Microbiol.* 47:676-679, 2001.
Bzducha-Wróbel et al., "Evaluation of the Efficiency of Different Disruption Methods on Yeast Cell Wall Preparation for β-Glucan Isolation,"*Molecules* 19(12):20941-20961, 2014.
Chisti et al., "Disruption of microbial cells for intracellular products," *Enzyme and Microbial Technology* 8(4):194-204,1986.
Comuzzo et al., "Effect of Different Lysis Treatments on the Characteristics of Yeast Derivatives for Winemaking," *Journal of Agricultural and Food Chemistry* 60(12):3211-3222, 2012.
Cornett et al., "Release of Autolytic Enzyme from *Streptococcus faecium* Cell Walls by Treatment with Dilute Alkali," *Journal of Bacteriology* 138(3):699-704, 1979.
International Search Report and Written Opinion, dated May 9, 2011, for International Application No. PCT/US2010/041441, 12 pages.
Lacriola et al., "Screen for Agents That Induce Autolysis in *Bacillus subtilis,*" *Antimicrobial Agents and Chemotherapy* 57(1):229-234, 2013.
Leduc et al., "Induction and Control of the Autolytic System of *Escherichia coli,*" *Journal of Bacteriology* 152(1):26-34, 1982.
Lesage et al., "Cell Wall Assembly in *Saccharomyces cerevisiae,*" *Microbiology and Molecular Biology Reviews* 70(2):317-343, 2006.
Rice et al., "Molecular Control of Bacterial Death and Lysis,"*Microbiology and Molecular Biology Reviews* 72(1):85-109, 2008.
Tsuchido et al., "Killing of *Bacillus subtilis* by Cell Suicide through Autolysis Induction," *Biocontrol Science* 1(1):19-24, 1996.
Xu et al., "Autolysis of *Aspergillus oryzae* Mycelium and Effect on Volatile Flavor Compounds of Soy Sauce," *Journal of Food Science* 81(8):C1883-C1890, 2016.
Dong et al., Combined algal processing: A novel integrated biorefinery process to produce algal biofuels and bioproducts, *Algal Research* 19:316-323, 2016.
Naghdi et al., "Progress on lipid extraction from wet algal biomass for biodiesel production," *Microbial biotechnology* 9:718-726, 2016.
OriginOil, "Algae Harvesting, Dewatering and Extraction," PowerPoint presentation, RAI Congress Centre, Amsterdam, Mar. 15-17, 2010, 30 pages.
Unkefer et al., "Review of the algal biology program within the National Alliance for Advanced Biofuels and Bioproducts," *Algal Research* 22:187-215, 2017.

* cited by examiner

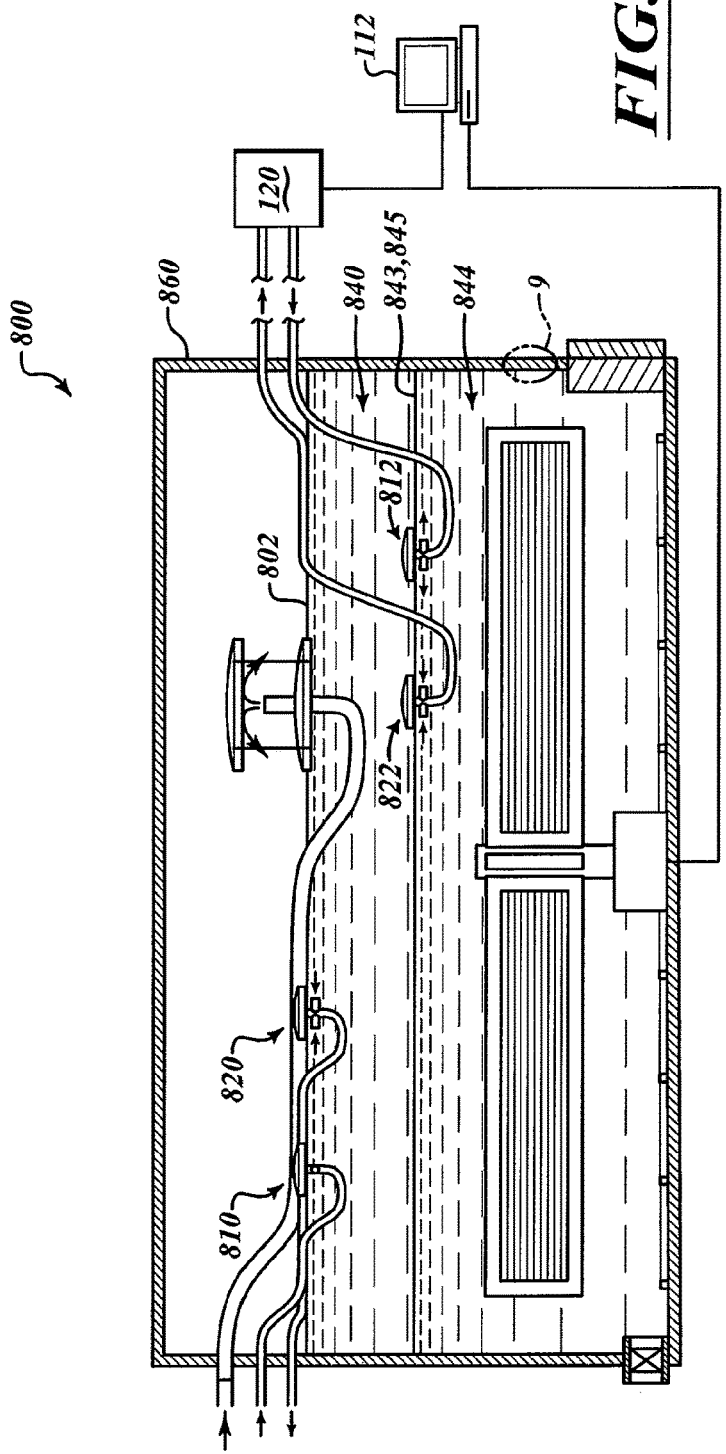

METHOD AND SYSTEM FOR PROCESSING A BIOMASS FOR PRODUCING BIOFUELS AND OTHER PRODUCTS

CROSS-REFERENCE TO RELATED APPLICATION

This application claims the benefit under 35 U.S.C. § 119(e) of U.S. Provisional Patent Application No. 61/223,995 filed Jul. 8, 2009, where this provisional application is incorporated herein by reference in its entirety.

BACKGROUND OF THE INVENTION

Field of the Invention

The present invention relates generally to methods of processing a biomass to obtain useful lipid and non-lipid materials, including intermediates for producing biodiesel and ethanol. In particular embodiments, a microorganism is grown on a biodegradable substrate and the resulting biomass is induced to undergo autolysis, thus releasing the lipid and non-lipid materials from the biomass. The present invention is also directed to a processing system useful for practicing the methods of the present invention.

Description of the Related Art

The global energy crisis is continuing to grow as fossil fuels are facing their inevitable depletion. At the same time, the burning of fossil fuels is increasing the production of greenhouse gases. Substituting biofuels for fossil fuels will decrease the greenhouse effect, and with a steady, sustainable, and uninterrupted supply, biofuels will not be a finite fuel source. However, liquid biofuels generated thus far have their own difficulties and concerns that need to be addressed and overcome.

The first generation of liquid biofuels was derived from plants, e.g., starch; cane sugar; and corn, rapeseed, soybean, palm, and other vegetable oils. Therefore, first generation biofuels compete with human and animal nutrition for agricultural crops, because these crops are produced on a limited amount of land. This limited amount of farm land cannot satisfy both global food and fuel needs, thereby generating the food vs. fuel conflict. Analysis has shown that alternative fuel vehicles will not be adopted unless the alternative fuels are made widely available (see, e.g., Struben and Sterman, Environment and Planning B: Planning and Design, 2008, 35(6):1070-1097 and Stauffer, Alternative-Fuel Vehicles: Enabling the Transition, MIT Energy Initiative Spotlight [online], [retrieved on Jul. 11, 2007]. Retrieved from the Internet: <URL: http://web.mitedu/mitei/research/spotlights/alternative-fuel.html>). Accordingly, first generation biofuels are limited by competition with food crops for land and cannot be abundant enough to become widely available, thus preventing the adoption of alternative fuels.

When it became clear that agricultural crops did not represent a steady, sustainable and uninterrupted supply for biofuels, researchers looked for new and abundant materials that contain ample polysaccharides and lipids to produce ethanol and biodiesel, respectively, and that are not in conflict with human and animal nutrition. The materials identified as new fuel sources were cellulose and algae, and the liquid biofuels produced from these materials are regarded as second generation liquid biofuels. Cellulose, or lignocellulose, was selected as the most abundant polysaccharide in nature, with an average polysaccharide content comprising 60% of the dry weight material. Algae were selected to produce lipids for several reasons. In particular, fatty acids constitute up to 40% or more of the overall mass of some types of algae, and algae have a fast rate of growth. In addition, algae consume the greenhouse gas carbon dioxide and produce the globally needed oxygen as a metabolic waste product.

However, the selection of lignocellulose and algae as starting materials introduced a new set of problems. In particular, generating ethanol from lignocellulose has a number of technical problems. Delignification of lignocellulose to liberate cellulose and hemicellulose from their complex with lignin is the rate-limiting and most challenging step in the production of ethanol from lignocellulose (Lin and Tanaka. *Appl Microbiol Biotechnol.* 2006; 69(6):627-642). In addition, depolymerization of the carbohydrate polymers (e.g., acid hydrolysis of the cellulose from wood) destroys most of the desired materials, simple fermentable sugars, in the process. Also, the fermentation of hexose and pentose sugars together generates a low ethanol yield. Hydrolysis of lignocellulose feedstock via high temperatures, acid treatment, and/or high pressure is also a complex energy consuming process. Enzymatic hydrolysis of pretreated cellulosic biomass with cellulase is a constrained process because the enzyme is inhibited by the hydrolysis products (i.e., glucose and short cellulose chains).

In addition to, and due in part to, the technical problems of generating lignocellulosic ethanol, its production cost is high despite the fact that lignocellulose is an inexpensive agricultural residue when compared to the starch-based agricultural products used in the production of first generation biofuels. Also, the costly initial investment to convert or build a lignocellulose refinery would result in a small number of lignocellulose refineries, high freight costs for delivering bulky cellulose long distances to the limited number of refineries, very large and costly storage areas to contain the biomass, and a large output of residual waste. The cost of lignocellulosic ethanol is not less than the cost of producing the first generation fuel. A study of the European ethanol market determined that the price of lignocellulosic ethanol would break even with that of fossil fuels when the price of oil is €90 ($115) per barrel (*Europe's Ethanol Market Potential*. Phoenix: Energy Business Reports, 2008). In the United States, a similar study indicated that the price of cellulosic biofuels would break even, without incentives, with that of fossil fuels when the price of oil is $90 per barrel (90-Billion Gallon Biofuel Deployment Study: Executive Summary. HITEC, February 2009 [online], [Retrieved on May 18, 2009]. Retrieved from the Internet: <URL: http://hitectransportation.org/news/2009/Exec_Summary02-2009.pdf>).

The high cost of lignocellulosic ethanol, the drastic drop in oil prices at the end of 2008, and the global economic crisis contributed in putting many lignocellulosic ethanol projects on hold and leading to a reluctance to invest in ethanol projects. Additionally, since the mid-1970s, extensive research has been carried out in the field of lignocellulosic ethanol production; however, the first lignocellulosic ethanol fuel plant was not operational until 2004 in Canada. It is a slowly developing technology, and it is only anticipated to replace one-third of the gasoline used in the United States by the year 2030. The political and environmental needs for alternative fuels are pressing (see, e.g., Milliken. "World has 10-Year Window to Act on Climate Warming—NASA Expert" Reuters, September 2006 [online], [Retrieved on May 18, 2009]. Retrieved from the Internet: <URL: http://www.commondreams.org/headlines06/0914-01.htm>), and the need for alternative fuels will also likely become heightened for economical reasons long before the lignocellulosic ethanol technology is able to meet them (see, e.g., The Rush to Ethanol: Not All Biofuels Are Created Equal [online], [Retrieved on May 18, 2009]. Retrieved from the Internet: <URL: http://www.newenergychoices.org/uploads/RushToEthanol-rep.pdf>).

Although the lipids derived from algae are readily converted to biodiesel by known methods, and lipid extraction via oilseed extraction is available (see, e.g., U.S. Pat. No. 4,456,556), the cultivation of algae is challenging. For example, growing algae in an open-pond system is much less expensive than growing algae in a closed photobioreactor system; however, the open-pond system is open to contaminants, and it is more difficult to provide optimal amounts of carbon dioxide and light while maintaining the temperature and pH to achieve maximum growth of the algae in an open-pond. Thus, stimulating exponential growth of algae in a closed or open system is costly, and cultivating algae on a commercial scale is exceedingly difficult. The industry is still testing a wide variety of methods for growing algae, e.g., open ponds, closed bioreactors, and other processes. Bioreactors have proven to be most effective in producing high quality algae at the greatest rate, but they are expensive, and it has yet to be shown that algae are economically feasible for commercial scale production (see, e.g., Benemann, Opportunities and Challenges in Algae Biofuels Production [online], [Retrieved on Jun. 22, 2009]. Retrieved from the Internet: <URL: http://www.futureenergyevents.com/algae/whitepaper/algae_positionpaper.pdf>).

In view of the limitations associated with the production of first and second generation biofuels, including the food vs. fuel conflict of first generation biofuels, and the high production costs associated with second generation biofuels, there is clearly a need in the art for new methods of efficiently and cost-effectively producing alternative fuels without taxing the environment or competing with food production. The present invention solves this problem by providing an efficient and cost-effective method to produce products useful in biofuels and other products.

BRIEF SUMMARY OF THE INVENTION

The present invention provides a new method to obtain both lipid and non-lipid materials from a biomass. In particular, the present invention provides a method for using a biomass, e.g., a biomass produced from a microorganism, to produce an autolysate from which both lipid and non-lipid materials may be obtained. In one embodiment, a microorganism is cultured or grown in the presence of a biodegradable substrate to produce a microbial biomass, which is then subjected to autolysis to release both lipid and non-lipid materials. In various embodiments, the microorganism utilizes any available biodegradable substrate.

In one general embodiment, the present invention provides a method of processing a biomass comprising: inducing autolysis of the biomass; and allowing the biomass to undergo autolysis in the presence of an organic solvent and an aqueous solution, thereby producing an autolysate comprising a layer comprising the organic solvent and a layer comprising an aqueous solution, wherein said layer comprising the organic solvent comprises lipids released from the biomass during the autolysis, and wherein said layer comprising the aqueous solution comprises non-lipid materials released from the biomass during autolysis. In certain embodiments, the method further comprises separately collecting one or both of the layer comprising the organic solvent and the layer comprising the aqueous solution (or a portion thereof). In other embodiments, the method further comprises fermenting a fermentable sugar to produce an alcohol, wherein the fermentable sugar is present in the aqueous solution. In particular embodiments, the fermenting step occurs prior to the collecting step.

In another general embodiment, the present invention provides a method of producing lipids and non-lipid materials by culturing a microorganism on a biodegradable substrate; harvesting the microorganism; inducing autolysis of the microorganism; and allowing the microorganism to undergo autolysis in the presence of an organic solvent and an aqueous solution, thereby producing an autolysate comprising a layer comprising the organic solvent and a layer comprising an aqueous solution, wherein the layer comprising the organic solvent contains lipids released from the microorganism during the autolysis, and wherein the layer comprising the aqueous solution contains fatty acids and non-lipid materials released from the microorganism during the autolysis. In particular embodiments, the method further comprises collecting one or both of the layer comprising the organic solvent and the layer comprising the aqueous solution. In particular embodiments, the method further comprises separately collecting both the layer comprising the organic solvent and the layer comprising the aqueous solution.

In certain embodiments of methods of the present invention, the microorganism is a fungus. The fungus may be a filamentous fungus, such as a white rot fungus. In a particular aspect, the white rot fungus is *Phanerochaete chrysosporium*. In yet another embodiment, the fungus is *Aspergillus fumigatus*. In particular embodiments, the fungus is yeast.

In other embodiments of the invention, the microorganism is a bacterium. In another embodiment, the microorganism is a protist. In a further embodiment, the protist is algae.

In one embodiment, the biodegradable substrate is a solid substrate. Particular embodiments of solid substrates comprise agricultural waste, landscaping waste, solid municipal waste, calcium carbonate, or coal. In another embodiment, the solid substrate is animate and comprises a parasite, such as a nematode.

In another embodiment of the methods of the present invention, the biodegradable substrate is a liquid substrate. Certain embodiments of liquid substrates comprise liquid municipal waste, blood, crude oil, salt water, or fresh water.

In certain embodiments, the methods of the present invention further comprise the step of sterilizing the biodegradable substrate. In one instance, sterilizing comprises adding chlorine dioxide.

In particular embodiments, the methods of the present invention further comprise the step of increasing the surface area of the biodegradable substrate. In particular embodiments, increasing the surface area comprises a mechanical process selected from grinding, chopping, or crushing.

In another embodiment, the methods of the present invention further comprise the step of optimizing the physiochemical conditions for culture of the microorganism. In certain embodiments, optimizing the culture conditions comprises supplying a nutritional supplement; supplying a gas such as $CO_2$ or $O_2$; or modulating the temperature, the humidity, or the pH.

In certain embodiments, the microorganism is harvested by mechanically collecting the microorganism. Particular embodiments of mechanically collecting the microorganism include manual collection, automated collection, and centrifugation. In one embodiment, harvesting the microorganism is accomplished by collecting a liquid solution containing the microorganism.

In one aspect of the invention, inducing autolysis comprises a mechanical process, such as homogenization. In another aspect, inducing autolysis comprises a chemical process. One exemplary chemical process comprises the addition of a chemical compound containing chlorine. Other embodiments of methods of inducing autolysis comprise sonicating the microorganism, an enzymatic process, modulating the temperature (e.g., increasing or decreasing the temperature), modulating the amount of light (e.g., increasing or decreasing the amount of light), and starving the microorganism. In various aspects of the invention, allowing the microorganism to undergo autolysis occurs over a period of days, hours, or minutes. In certain embodiments, autolysis may be inducing by killing the microorganisms or biomass.

In some embodiments, methods of the present invention further comprise the step of inhibiting cellular glucose oxidase. One embodiment of a method of inhibiting cellular glucose oxidase comprises adding $H_2O_2$ to the autolysate. The $H_2O_2$ can be neutralized by the addition of sodium bicarbonate.

Certain embodiments of the invention further comprise the step of storing the autolysate. In one embodiment, the autolysate is stored at a temperature below 10° C. In a further embodiment, the temperature is 2-3° C.

In one embodiment of the invention, the step of separately collecting one or more layers comprises decanting. In another embodiment, separately collecting comprises skimming. In yet another embodiment, separately collecting comprises collecting each layer out of a separation tower.

In particular embodiments, methods of the present invention further comprise the step of isolating or purifying the lipids from the organic solvent and/or aqueous solution. A further embodiment also includes the step of recovering the organic solvent. In certain embodiments, methods of recovering the organic solvent comprise evaporation and condensation. The invention also provides for reusing the recovered organic solvent. In particular embodiments, the organic solvent is hexane.

Certain embodiments further include producing biodiesel from the lipids obtained from the autolysate. In one aspect, producing biodiesel comprises transesterification of the lipids. In certain embodiments, transesterification utilizes a batch reactor, supercritical alcohol, an ultrasonic reactor, or microwave irradiation. In a related embodiment, glycerol is a byproduct of said transesterification. In a further embodiment, biodiesel and glycerol are produced at a ratio of about 9:1.

In certain embodiments of the invention, the aqueous layer comprises glucose. Particular embodiments further comprise the step of isolating or purifying the glucose from the aqueous layer. In one embodiment, isolating the glucose comprises chromatography. Another embodiment further comprises producing $H_2$ from the glucose. In a related embodiment, producing $H_2$ comprises a synthetic enzymatic pathway that yields $H_2$ and $CO_2$ from glucose. In a further embodiment, the $H_2$ is stored in a container. In yet another embodiment, the $H_2$ is used for fuel. In a related embodiment, the $CO_2$ is used to culture a microorganism.

In one aspect, the aqueous layer comprises a fermentable sugar. In related embodiments, the fermentable sugar comprises glucose, fructose, ribose, xylose, or sucrose. In certain embodiments, the method of producing lipids and non-lipid materials further comprises the step of fermenting the fermentable sugar to produce an alcohol or acetone. In one embodiment, the alcohol is ethanol. In particular embodiments, fermentation is performed by contacting the aqueous layer comprising a fermentable sugar with a microorganism capable of fermenting a sugar into an alcohol or acetone. In a related embodiment, the fermenting step utilizes *Saccharomyces cerevisiae*. In another embodiment, the fermenting step utilizes *Zymomonas mobilis*. In yet another embodiment, the fermenting step utilizes *Escherichia coli*. In certain embodiments, the fermenting step produces $CO_2$ that can be used to culture microorganisms. In another embodiment, the alcohol is butanol. In related embodiments, the fermenting step utilizes *Clostridium beigerinckii, C. acetobutylicum*, or *C. tetanomorphum*. In another embodiment, the alcohol is isopropanol. In another related embodiment, the method further comprises isolating the alcohol. In particular embodiments, the step of isolating utilizes steam stripping distillation, adsorption, gas stripping, or pervaporation.

In certain aspects of the invention, the aqueous layer comprises amino acids. Thus, in particular embodiments, the method includes the step of isolating or purifying amino acids from the aqueous layer. A related embodiment further comprises the step of producing a nutrition supplement from these amino acids. In a particular embodiment, the nutrition supplement is for animal consumption. In one embodiment, the animal is a human. In another embodiment, the nutrition supplement is a plant fertilizer.

In a certain embodiment, the aqueous layer comprises an organic acid. In another related embodiment, the aqueous layer comprises an inorganic acid. In yet another embodiment, the aqueous layer comprises a polyhydric alcohol. Thus, in particular embodiments, the method includes the step of isolating or purifying organic acid, inorganic acid, and/or polyhydric alcohol from the aqueous layer. A further embodiment comprises the step of producing a sweetener from the polyhydric alcohol. In one embodiment, the aqueous layer comprises a nitrogenous compound. In particular embodiments, the aqueous layer comprises an enzyme. Thus, in particular embodiments, the method includes the step of isolating or purifying nitrogenous compounds or enzymes from the aqueous layer. A related embodiment further comprises the step of producing a detergent from the enzyme. In yet another embodiment, the aqueous layer comprises a vitamin. Thus, in particular embodiments, the method includes the step of isolating or purifying amino acids from the aqueous layer. A related embodiment further comprises the step of producing a nutrition supplement from the vitamin.

Certain embodiments of the invention further comprise the step of isolating or purifying the non-lipid materials, or one or more non-lipid material. In particular related aspects, the isolating step comprises electrophoresis, chromatography, membrane separation, or centrifugation.

In another aspect, methods of the present invention further comprise using the aqueous layer as nutritional supplement. In certain embodiments, the nutritional supplement is used for consumption by an animal, a microorganism, or a plant.

In another related embodiment, the present invention includes a method of producing fresh water or purified water comprising culturing a microorganism on a biodegradable substrate in the presence of salt water, brackish water, waste water, or contaminated water; harvesting the microorganism; inducing autolysis of the microorganism; and allowing the microorganism to undergo autolysis in the presence of an organic solvent and an aqueous solution, thereby producing an autolysate comprising a layer comprising the organic solvent and a layer comprising an aqueous solution, wherein said layer comprising the aqueous solution comprises fresh or purified water; and collecting and the layer comprising the aqueous solution. In particular embodiments, fresh or purified water is further purified from some or all other lipid or non-lipid materials released from the microorganism during autolysis. In particular embodiments, the fresh water has less than 500 parts per million (ppm) of dissolved salts.

In a further related embodiment, the present invention includes processing system, comprising: a container having a chamber for holding biomass and autolysate, wherein said autolysate comprises an organic solvent layer and an aqueous layer; a mixing apparatus including at least one fin positioned in the chamber and a motor, the at least one fin moves to mix biomass and autolysate when the motor is energized; a feed apparatus including a biomass, lysate and/or autolysate source coupled to the container and an organic solvent source coupled to the container; a collection unit in fluid communication with the container, the collection unit configured to collect the aqueous layer of the autolysate and components therein; and a controller communicatively coupled to the feed apparatus and the collection unit, wherein the controller is configurable to command the collection unit to remove the aqueous layer from the chamber and, optionally, to separate or extract the components from the aqueous layer, and is configured to command the feed apparatus to adjust the composition of the autolysate. In particular embodiments, at least one fin is movable between a raised position and a lowered position and is rotatable about an axis of rotation. In certain embodiments, the controller is communicatively coupled to the mixing apparatus, the controller causes the motor to move the at least one fin vertically along the chamber based on at least one signal from a sensor. In particular embodiments, the collection unit includes a filter that separates the biomass, lysate and/or autolysate while the feed apparatus delivers an organic solvent from the organic solvent source to the chamber and while the feed apparatus delivers biomass, lysate and/or autolysate from the biomass, lysate and/or autolysate source to the chamber. In certain embodiments, the processing system further comprises: a biomass, lysate and/or autolysate inlet unit floatable on the organic solvent layer of the autolysate in the chamber and through which biomass, lysate and/or autolysate and/or autolysate from the biomass, lysate and/or autolysate source flows. In particular embodiments, the biomass, lysate and/or autolysate inlet unit includes a float having a curved upper surface and a delivery tube, the delivery tube outputs the biomass, lysate and/or autolysate such that the biomass, lysate and/or autolysate falls on the curved upper surface and drains to the upper surface of the organic solvent layer of the autolysate in the chamber. In particular embodiments, the processing system further comprises: an inlet unit floatable on the autolysate in the chamber and capable of outputting a flowable substance independent of a flow of biomass, lysate and/or autolysate from the biomass, lysate and/or autolysate inlet unit. In certain embodiments, the processing system further comprises an organic solvent layer collection unit in fluid communication with the container, the organic solvent collection unit configured to collect the organic solvent layer of the autolysate and components therein.

In another related embodiments, the present invention includes a method of processing biomass, comprising: delivering an aqueous solution comprising biomass, lysate and/or autolysate to a processing system, wherein the aqueous solution forms a layer comprising an aqueous solution; delivering an organic solvent out of a first port of said processing system, wherein said organic solvent forms a layer comprising the organic solvent above the layer comprising the aqueous solution, and wherein the first port is positioned above the layer comprising the aqueous solution; allowing the aqueous solution of the layer comprising the aqueous solution to ferment; and drawing organic solvent comprising lipids from the layer comprising the organic solvent into a second port positioned within the layer comprising the organic solvent while the aqueous solution ferments. In certain embodiments, the method further comprises: floating a biomass, lysate and/or autolysate inlet unit on the layer comprising the organic solvent, wherein the biomass, lysate and/or autolysate inlet unit delivers biomass, lysate and/or autolysate; floating an organic solvent inlet unit on the layer comprising the organic solvent, wherein the organic solvent inlet unit comprises the first port; and floating an outlet unit with the second port on the organic solvent layer while the organic solvent comprising lipids is drawn. In certain embodiments, the method further comprises: mixing the layer comprising the aqueous solution by moving mixing elements while the biomass, lysate and/or autolysate inlet unit, the organic solvent inlet unit, and the outlet unit float on the layer comprising the organic solvent. In particular embodiments, the method further comprises: delivering material from the layer comprising the aqueous solution to a collection unit; and separating one or more components of the delivered material from the layer comprising the aqueous solution using the collection unit. In particular embodiments, the method further comprises: delivering material from the layer comprising the organic solvent to a collection unit; and separating one or more components of the delivered material from the layer comprising the organic solvent using the collection unit. In particular embodiments, the material collected from the layer comprising the organic solvent comprises a lipid.

BRIEF DESCRIPTION OF THE SEVERAL VIEWS OF THE DRAWINGS

Non-limiting and non-exhaustive embodiments are described with reference to the following drawings. The same reference numerals refer to like parts or acts throughout the various views, unless otherwise specified.

FIG. 8 is a cross-sectional elevational view of a processing system, in accordance with one embodiment.

FIG. 9 is a detailed view of a portion of a container of the processing system of FIG. 8.

DETAILED DESCRIPTION OF THE INVENTION

Figure 1:
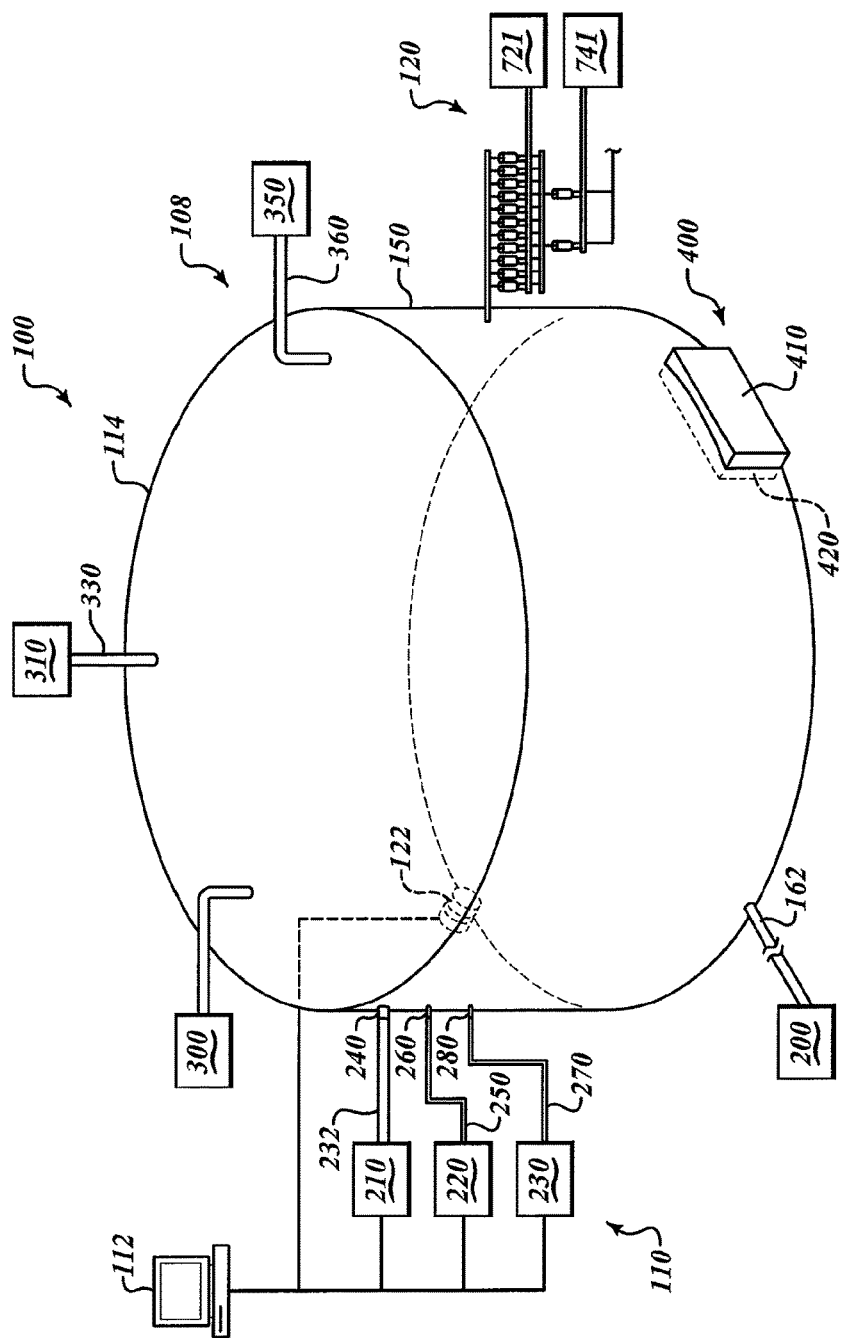
FIG. 1 is an elevational view of a processing system that may be used for any or all of the steps of autolysis, fermentation, separation, and storage.

The present invention provides a method of processing a biomass in order to produce useful lipid and non-lipid materials, e.g., from a biodegradable substrate. Accordingly, the present invention also provides a method of producing lipids and non-lipid materials from an autolysate produced from a microorganism utilized to degrade a biodegradable substrate. Both lipid and non-lipid materials can be generated simultaneously from the autolysate, and a wide variety of products, including biodiesel, alcohol, and nutritional supplements can be obtained and produced from the lipid and non-lipid materials. As used herein, the term "lipid" refers to fatty acids and their derivatives, and substances related biosynthetically or functionally to these compounds. Lipids include both water-soluble lipids and non-water-soluble lipids.

One of the great disadvantages of first and second generation methods of producing biofuels is that both methods view the biomass as a source of only one component, either sugars or lipids. By definition, a biological cell contains both sugars and lipids together in addition to many other valuable materials that can be converted into higher value "bioproducts". The present invention provides a novel and innovative method for obtaining valuable materials, both lipid and non-lipid, from a biomass.

The methods of the present invention are advantageous for many reasons. Because the present invention uses any available biodegradable material and any microorganism, it eliminates the food vs. fuel conflict of first generation biofuels, is available for use all over the world, because biodegradable materials and microorganisms are present in all parts of the world, and eliminates the use of heat and acids for starch hydrolysis by utilizing autolysis instead. With regard to second generation biofuels, the methods of the present invention are advantageous, because they can rely on the microorganism for delignification of lignocellulose and depolymerization of polysaccharides as they are converted into the microbial biomass. In addition, glucose and other simple sugars are not destroyed by the current methods, because autolysis is used instead of manmade hydrolysis. Also, high temperature, acid treatment, and/or high pressure are not required, because autolysis is used instead of manmade hydrolysis.

The methods of the present invention present a relatively affordable initial investment in comparison to second generation biofuels, and are thereby more cost-effective. In addition, the microorganism may be cultivated and autolysed at the site of the substrate (i.e., transformation goes on where the biodegradable material is present), thereby further reducing costs by limiting transportation expenses. Furthermore, the utilized microorganism may be cultivated on degradable waste materials, and in this way can be cultivated proximal to the consumers. Since the production-distribution grid for the biofuels is smaller in size, the transportation costs associated with the biofuels is also reduced. The lipid and non-lipid materials produced from the methods of the present invention can all be used or recycled in some way so that there are little or no costs associated with transporting, storing, and managing residuals or waste products. Because the biodegradable substrate can be waste material, the raw materials are essentially cost free. The new, low cost, organic and/or biological products generated according to the methods of the present invention may contribute to a wide variety of industries.

The methods of the present invention are also advantageous over both first and second generation biofuels because, in addition to biofuel production, several revenue centers (e.g., amino acids, enzymes, and chemical building blocks) are opened within the same project, thus increasing the profitability. Furthermore, methods of the present invention may be practiced using biomass generated by other processes that already use microorganisms (e.g., pharmaceutical, brewing, fermentation, and the production of fungal spores as a biological pesticide). Overall, the methods of the present invention embody an integrated bio-refinery process utilizing an ecotechnology.

As described herein, methods of the present invention may be used to generate a variety of valuable products. In addition, they are useful in protecting and restoring the environment. For example, amino acids, vitamins, antibiotics, peptides, nutrients, elements prepared according to the methods of the present invention may be used in fertilizers, including totally soluble organic fertilizer. This will reverse the increase in land use change, because organic top soil, built up by organic soluble fertilizers, is an important sink for atmospheric $CO_2$. It will also reverse land desertification by rebuilding organic lands' top soil, and it will expedite sandy and clay lands reclamation that will serve as a new sink for atmospheric $CO_2$ and will cultivate plants that absorb atmospheric $CO_2$. In addition, it will reduce $N_2O$ and $CH_4$ emitted by manure fertilizers and by chemical fertilizers. This will also encourage and expedite urban high-rise vertical organic farming that will reduce GHG emissions by reducing the transportation of farm goods and absorbing atmospheric carbon, supply towns and cities with fresh produce, and reduce the need for irrigation water.

In addition, the methods of the present invention make waste water treatment much easier and more economical, e.g., agricultural waste water will be recyclable. Soluble organic fertilizers in agricultural run-offs will not pollute waterways or ground water, etc. Instead, agricultural run-offs will be loaded with nutrients usable by fish, plants, livestock, poultry, swine etc. Thus, the methods and products of the present invention will reverse the dead zones created by agricultural run-offs to areas full of nutrient zones. In addition, they will reduce acid rain by reducing $N_2O$ in agricultural run-offs.

Furthermore, the use of amino acids, vitamins, antibiotics, peptides, fatty acids, sugars, and other basic nutritional elements obtained according to the methods of the present invention, which are typically organic and completely digested, as supplements in ruminant animals' food will reduce their $CH_4$ emission and, thus, increase the animals' productivity.

Biodegradable Substrate

As described above, one advantage of the present invention is that the microorganisms used to produce lipid and non-lipid materials may be grown on a wide variety of inexpensive and readily available biodegradable substrates. A "biodegradable substrate" or "substrate" as used herein refers to any material that can be consumed and/or degraded (e.g., aerobic or anaerobic degradation) by a microorganism. The biodegradable substrate may be inanimate or living (e.g., parasites). The biodegradable substrate may be a liquid or a solid, and it may be inorganic or organic. In certain preferred embodiments, the biodegradable substrate is waste or a byproduct. Preferably, but not necessarily, the substrate possesses a high energy density.

Examples of solid biodegradable substrates include, but are not limited to, cellulosic waste materials, farming, agricultural, and landscaping waste (e.g., non-edible portions of plants, leaves, stems, branches, flowers, seeds, clippings, husks, mulch, and manure), solid municipal waste (e.g., household and commercial waste, such as paper, cardboard, yard and food waste), calcium carbonate (e.g., limestone, eggshells, and shells of marine organisms), coal (e.g., peat, anthracite, and graphite), and parasites (e.g., nematodes, cestodes, trematodes, and protozoa).

Examples of liquid biodegradable substrates include, but are not limited to, liquid municipal waste (e.g., household and commercial waste, such as wastewater and sewage), non-potable water, urine, blood and other bodily fluids (e.g., slaughterhouse waste), silage, industrial organic waste, dairy farming waste, fruit and vegetable washing water, cooling water (e.g., water used in iron and steel production), mining slurry, sludge, and crude oil and derivatives (e.g., petroleum, motor oil, and lubricants). Aqueous substrates may contain saltwater or freshwater.

Since any available biodegradable substrate may be used, the substrate does not need to be transported long distances, if at all. Unlike the production of first and second generation biofuels, the feedstock material, i.e., the biodegradable substrate, can be utilized at or near its source. Furthermore, the final products, the lipid and non-lipid materials obtained from the autolysate, can be generated in close proximity to or at the site of the substrate to reduce costs for transportation and distribution of the newly obtained materials.

In addition, new feedstock sources, such as crops, do not need to be generated and harvested to begin the process, e.g., when the substrate is a waste material. Furthermore, the generation of fuel and other valuable products from waste material reduces the global need for waste removal and storage, such as municipal landfills. Since there are biodegradable materials and microorganisms all over the world, the wide availability of alternative fuels will not be a problem using the present methods as is the case with first and second generation biofuels. Furthermore, the present invention will eliminate problems associated with the reliance on fossil fuel sources. Using the methods of the present invention, the dependency will shift to a reliance on globally available and abundant materials to produce biofuels.

Microorganisms

A wide variety of different microorganisms may be used according to the methods of the present invention. In particular embodiments, the microorganism used may be selected based upon its ability to degrade a desired substrate. For example, brown rot fungi are capable of consuming cellulose and hemicellulose; white rot fungi are capable of consuming lignocellulose; and *Saccharomyces cerevisiae* and *Zymomonas mobilis* are capable of consuming glucose. Information regarding the ability of various microorganisms to consume or degrade particular biodegradable substrates is available in the art.

Microorganisms that may be used according to the present invention include, but are not limited to, bacteria, fungi, and protists. These microorganisms include, e.g., unicellular and multi-cellular organisms; prokaryotes and eukaryotes; aerobes, anaerobes, and facultative anaerobes; rod shaped, sphere shaped and spiral shaped organisms; sexually and asexually reproduced organisms; thermophiles, psychrophiles, mesophiles, acidophiles, alkaliphiles, and other extremophiles; and autotrophic and heterotrophic organisms. Additionally, the microorganisms utilized according to the present invention may be wild type organisms or genetically modified organisms.

"Biomass" or "microorganism biomass" or "microbial biomass" is used herein to refer collectively to the microorganisms utilized to degrade the substrate, and it is the source of the autolysate. In particular, these terms may refer to the microorganism biomass generated following culturing of the microorganism on a biodegradable substrate.

Bacteria

Microorganisms that can be utilized for the degradation of a substrate include any bacterial species. Such bacteria include, but are not limited to, Gram-positive and Gram-negative bacteria, acidobacteria, actinomycetes, cyanobacteria (i.e., blue-green algae), endospore-forming bacteria, enteric bacteria, firmicutes, fusobacteria, green non-sulfur bacteria, green sulfur bacteria, mycoplasms, myxobacteria, phototrophic bacteria, planctomycetes, proteobacteria, pseudomonads, rickettsias, spirochetes, sulfur-reducers, and thermophilic bacteria. For example, bacteria from the following genera may be used: *Acinetobacter, Achromobacter, Alcaligenes, Alcanivorax, Aromatoleum, Arthrobacter, Bacillus, Bradyrhizobium, Brevibacterium, Burkholderia, Chromobacterium, Clostridium, Corynebacterium, Desulfitobacterium, Desulfovibrio, Desulfotomaculum, Fibrobacter, Flavobacterium, Geobacter, Lactobacillus, Methylosinus, Methylomonas, Methylobacterium, Micrococcus, Mycobacterium, Nitrosomonas, Nocardia, Pseudomonas, Rhizobium, Rhodococcus, Sarcina, Spirillum, Streptomyces, Thermus, Vibrio*, and *Xanthomonas*.

Fungi

Microorganisms that can be utilized for the degradation of a substrate further include any fungal species. Such fungi include, but are not limited to, microscopic species from the following divisions: Zygomycota, Ascomycota, Basidiomycota, Deuteromycota, and Lichens. Examples of fungi that may be used include, but are not limited to, *Acremonium strictum, Actinomucor elegans, Antrodia radiculosa, Aspergillus aculeatus, Aspergillus awamori, Aspergillus ficuum, Aspergillus foetidus, Aspergillus japonicus, Aspergillus nidulans, Aspergillus niger, Aspergillus oryzae, Aspergillus sojae, Aspergillus tubigensis, Aspergillus versicolor, Bjerkandera adusta, Blumeria graminis, Chaetomium bolichotlitum, Cladosporium resinae, Erysiphe nectar, Fusarium oxysporum, Geomyces pannorum, Leveillula taurica, Meruliporia incrassate, Neurospora crassa, Paecilomyces lilacinus, Paecilomyces ramosus, Paecilomyces viridis, Penicillium atramentosum, Penicillium bilaiae, Penicillium camemberti, Penicillium candida, Penicillium funiculosum, Penicillium glaucum, Penicillium herquei, Penicillium lanosocerulum, Penicillium roquefortii, Penicillium similicissum, Phanerochaete chrysosporium, Phanerochaete sorida, Phlebia radiata, Pilobolus crystaffinus, Pilobolus longipes, Pluerotis ostreatus, Puccinia triticina, Pycnoporus cinnabarinus, Rhizopus stolonifer, Sordaria fimicola, Stagonospora gigaspora, Tilletia tritici, Tolypocladium inflatum, Trametes hirsute, Trametes versicolor, Ustilago maydis, Veticillium sp.*, and *Verticillium dahliae*. In certain embodiments, the fungus is a filamentous fungus (e.g., *Aspergillus fumigatus* and *Phycomyces blakesleeanus*), a brown rot fungus (e.g., *Trichoderma ressei* and *Trichoderma hazanium*), or a white rot fungus (e.g., *Phanerochaete chrysosporium*). In other embodiments, the fungus is a yeast.

Yeast is a type of fungus, and a wide variety of yeast species are comprised by the Ascomycota and Basidomycota divisions. Examples of yeast species that may be used include, but are not limited to, *Candida kefyr, Candida krusei, Candida lusitaniae, Candida milleri, Candida tropicalis, Candida utilis, Endomycopsis vernalis, Lipomyces lipofer, Lipomyces starkeyi, Pichia pastoris, Rhodotorula glutinis, Rhodotorula gracilis, Saccharomyces bayanus, Saccharomyces boulardii*, and *Yarrowia lipolytica*. In particular embodiments, the yeast is *Saccharomyces cerevisiae*.

Protists

Microorganisms that can be utilized for the degradation of a substrate include any protist species. As used herein, "protist" includes, but is not limited to, protozoa, algae, and fungi-like protists. Protists are single or multi-cellular eukaryotes. Protozoa that may be used include, e.g., organisms from the phyla Actinopoda (e.g., *Actinophrys, Actinosphaerium, Raphidiophrys, Heterophrys, Oxnerella*), Aoomastigina, Apicomplexa (e.g., *Aggregata, Atoxoplasma, Cystoisospora, Plasmodium, Schellackia* and *Toxoplasma*), Ciliophora (e.g., *Paramecium and Tetrahymena*), Foraminifera, and Rhizopoda. Fungi-like protists (e.g., slime and water molds) include organisms from the phyla Acrasidae, Myxogastria (e.g., *Physarum polycephalum* and *Fuligo septica*), and Oomycota (e.g., *Pythium oligandrum* and *Pythium acanthicum*).

Algae that may be used include, but are not limited to, microorganisms (i.e., microalgae) from the phyla Bacillariophyta (i.e., diatoms such as *Thalassiosira pseudonana, Phaeodactylum tricornutum*, and *Cyanidioschyzon merolae*), Chlorophyta (i.e., green algae such as *Chlamydomonas reinhardtii* and *Ulva lactuca*), Chrysophyta (i.e., golden algae such as *Chromulina pascheri, Dinobryon bavaricum* and *Dinobryon divergens*), Dinoflagellata (e.g., *Gonyaulex tamarensis* and *Ceratium* sp.), Euglenophyta (e.g., *Euglena gracilis*), Paeophyta (i.e., brown algae such as *Ochromonas minima*), and Rhodophyta (i.e., red algae such as *Cyanidioschyzon merolae*).

The microorganism utilized according to the methods of the present invention can be any microorganism capable of degrading the biodegradable substrate. Selection of the microorganism species may be based on the desired lipid and non-lipid materials to be obtained following autolysis of the microorganism. Preferably, the species of microorganism utilized will have a high affinity for the available substrate and will require the least amount of supplemental nutrients in the presence of the substrate. Certain microorganisms will have a higher specific growth rate ($\mu$) and a greater biomass yield (Yx/s) in the presence of the available substrate in comparison to other microorganisms. Also, certain microorganisms are capable of achieving a high cell density when grown on the substrate. If producing liquid biofuels is the main target, microorganisms that have high polysaccharide and/or lipid cell contents are preferred.

In certain embodiments, the methods of the present invention are practiced using two or more different microorganisms. In other embodiments, a single microorganism species is used. When more than one species of microorganism is used, the different microorganisms may be used simultaneously, interchangeably, or consecutively. Simultaneous culture refers to growing two or more different microorganisms on the substrate at the same time (at least for a portion of the time that each microorganism is cultured). An example of a simultaneous culture is a symbiosis, such as the fungi and algae that make up lichen; the fungi component supplies water and minerals while the algae component provides carbohydrate fuel from photosynthesis. An interchangeable culture refers to growing two or more different microorganisms on the substrate at different stages in order to enhance consumption of the substrate. For example, white rot fungus and brown rot fungus may be utilized alternately to depolymerize lignin and its components (i.e., cellulose and hemicellulose), respectively. The alternate use of the two or more microorganisms may be repeated as necessary to degrade the substrate. Consecutive culture refers to growing two or more different microorganisms in sequential order. A consecutive culture may be particularly useful in the case of a toxic and/or poisonous substrate or autolysate. In the case that one microorganism generates a toxic substance or toxin (i.e., a natural poison produced by a living organism) in the autolysate, a second species of microorganism, such as a fungus or bacterium that is capable of detoxifying the toxic substance, may be introduced for bioremediation of the toxic substance. As used herein, "poison" refers to any substance, natural or synthetic, that is harmful or deadly to living cells even in small quantities. In particular embodiments, the toxic substance falls in any of these three categories: (1) A chemical that has a median lethal dose ($LD_{50}$) of more than 50 milligrams per kilogram but not more than 500 milligrams per kilogram of body weight when administered orally to albino rats weighing between 200 and 300 grams each; (2) a chemical that has a median lethal dose ($LD_{50}$) of more than 200 milligrams per kilogram but not more than 1,000 milligrams per kilogram of body weight when administered by continuous contact for 24 hours (or less if death occurs within 24 hours) with the bare skin of albino rabbits weighing between two and three kilograms each; or (3) a chemical that has a median lethal concentration ($LC_{50}$) in air of more than 200 parts per million but not more than 2,000 parts per million by volume of gas or vapor, or more than two milligrams per liter but not more than 20 milligrams per liter of mist, fume or dust, when administered by continuous inhalation for one hour (or less if death occurs within one hour) to albino rats weighing between 200 and 300 grams each.

Some species of microorganisms, particularly fungi and bacteria, are useful in the bioremediation of heavy metals and toxic compounds found in contaminated waste waters. For example, these microorganisms are able to grow and flourish in contaminated wastewater and simultaneously remove the heavy metal from the substrate and into the cell of the utilized microorganism. Accordingly, in certain embodiments of methods of the present invention, a microorganism useful in the bioremediation of heavy metals and/or toxic compound is cultured with a biodegradable substrate comprising heavy metals and/or toxic compounds, e.g., waste water. In particular embodiments, once bioremediation has taken place, this microorganism (i.e., the first microorganism) is then collected, and a second microorganism is introduced to the substrate. The amino acids of the first microorganism will chelate the heavy metals, thereby leaving the other lipid and non-lipid materials to be utilized as described herein. The second microorganism will generate a poison-free or poison-reduced autolysate containing the lipid and non-lipid materials, as well as clean recycled water produced by both microorganisms. Other means of removing heavy metals from a substrate include the use of chitin and/or chitosan to absorb the heavy metals.

In another example, seawater algae are able to utilize and desalinate salt water, thereby producing recoverable intracellular fresh water. In yet another example, a microorganism utilized to degrade agricultural waste partially retrieves fresh water used for irrigation.

In one example, the fungus *Fusarium oxysporum* may be chosen as the microorganism to degrade a substrate containing zircon. It has been shown that extracellular enzymes of *F. oxysporum* generate zirconium nanoparticles from zircon sand (Bansal et al. *Langmuir.* 2007, 23(9): 4993-4998). By using *F. oxysporum*, zirconium is generated in addition to the other lipid and non-lipid materials derived from the autolysate.

In yet another example, nematophagous fungi are utilized as the microorganism biomass. Culturing the fungi on the biodegradable substrate (e.g., nematode contaminated moist, sandy soil) kills the nematodes present in or on the substrate, and the spores produced by the fungi growing on the substrate can be collected (e.g., vacuumed) prior to the induction of autolysis of the biomass. The collected spores can then be packaged and sold and/or used as a bio-nematicide product.

In another example, if the biodegradable substrate is crude oil or coal, a white rot fungus, such as *Phanerochaete chrysosporium* or *Neosartorya fischeri*, capable of utilizing crude oil or coal as a carbon source to produce valuable bioproducts such as biofuel and hydrogen may be utilized (see, e.g., Bumpus. *Appl Environ Microbiol.* 1989, 55(1): 154-8 and Igbinigie et al. *Biotechnol J.* 2008, 3(11):1407-16).

Methods of Processing a Biomass for the Production of Lipid and Non-Lipid Materials The present invention provides novel methods of processing a biomass, which are useful in obtaining lipids and other useful materials from a biomass. Thus, the methods of the present invention provide a novel way of producing lipids and non-lipid materials from a microorganism biomass. A wide variety of products including biodiesel, alcohol, and nutritional supplements can be obtained and produced from the lipid and non-lipid materials according to the methods of the present invention.

In particular embodiments, methods of the present invention comprise one or more of the following steps: culturing or incubating a microorganism with a biodegradable substrate to produce a microbial biomass; inducing autolysis of the microbial biomass; allowing the microbial biomass to undergo autolysis; contacting the biomass and any resulting lysed biomass ("lysate") with an organic solvent and/or an aqueous solution, resulting in an autolysate mixture ("autolysate") comprising a layer comprising the organic solvent ("organic solvent layer") and a layer comprising the aqueous solution ("aqueous layer"); fermenting a sugar present in the aqueous layer; collecting one or both layers of the resulting autolysate; and isolating or purifying lipids and/or non-lipid materials from one or both layers of the autolysate, as described further below. It is understood according to the methods of the present invention that the organic solvent layer may comprise other cellular components in addition to lipids, and it is also understood that certain lipids (or a portion of certain lipids) may be present in the aqueous solution.

In certain embodiments of methods of the present invention, the biomass is allowed to undergo autolysis prior to being contacted with the organic solvent and/or aqueous solution; while in certain embodiments, the biomass is allowed to undergo autolysis in the presence of the organic solvent and aqueous solution. In particular embodiments, initiation of autolysis occurs before contacting the biomass with the organic solvent, and the biomass and any autolysed biomass ("lysate") that has been produced since initiation of autolysis is contacted with the organic solvent and/or aqueous solution, and autolysis is then allowed to continue.

In certain embodiments, the present invention includes a method of processing a biomass comprising: inducing autolysis of the biomass; and allowing the biomass to undergo autolysis to produce a lysate; contacting the biomass and/or lysate with an organic solvent and an aqueous solution, thereby producing an autolysate comprising a layer comprising the organic solvent and a layer comprising an aqueous solution, wherein said layer comprising the organic solvent comprises lipids released from the biomass during autolysis, and wherein said layer comprising the aqueous solution comprises non-lipid materials released from the biomass during autolysis. In certain embodiments, the biomass is allowed to undergo autolysis in the presence of the organic solvent and the aqueous solution. In particular embodiments, the method also comprises separately collecting one or both of the layer comprising the organic solvent and the layer comprising the aqueous solution (or a portion thereof on one or both). In certain embodiments, this method may comprise fermenting a fermentable sugar present in the aqueous solution to produce an alcohol. In particular embodiments, the fermenting step occurs prior to collecting one or both of the layers, but it may also be performed on a collected aqueous layer. In one exemplary embodiment, the biomass is a fungus.

In one embodiment, the present invention includes a method of processing a biomass comprising: inducing autolysis of the biomass; and allowing the biomass to undergo autolysis in the presence of an organic solvent and an aqueous solution, thereby producing an autolysate comprising a layer comprising the organic solvent and a layer comprising an aqueous solution, wherein said layer comprising the organic solvent comprises lipids released from the biomass during the autolysis, and wherein said layer comprising the aqueous solution comprises non-lipid materials released from the biomass during autolysis. In particular embodiments, the method also comprises separately collecting one or both of the layer comprising the organic solvent and the layer comprising the aqueous solution (or a portion thereof on one or both). In certain embodiments, this method may comprise fermenting a fermentable sugar present in the aqueous solution to produce an alcohol. In particular embodiments, the fermenting step occurs prior to collecting one or both of the layers, but it may also be performed on a collected aqueous layer. In one exemplary embodiment, the biomass is a fungus.

Accordingly, in particular embodiments, methods of the present invention comprise the simultaneous or overlapping autolysis and fermentation of a biomass and/or sugars released from the biomass during autolysis. In other embodiments, methods of the present invention comprise the simultaneous or overlapping autolysis of a biomass and separation of lipid and non-lipid products released from the biomass into the organic solvent and aqueous solution. In further embodiments, methods of the present invention comprise the simultaneous or overlapping autolysis of a biomass, separation of lipid and non-lipid products released from the biomass into organic solvent or aqueous solution, and fermentation of the biomass and/or sugars. As used herein, the term "simultaneous" indicates that at least a portion of each step being performed simultaneously is conducted at the same time. For example, one or more step, e.g., autolysis or fermentation, may be performed for a longer or shorter period of time, so long as a portion is performed during the same time period.

In a related embodiment, the present invention includes a method of producing lipids and non-lipid materials comprising: culturing a microorganism on a biodegradable substrate; harvesting the microorganism; inducing autolysis of the microorganism; and allowing the microorganism to undergo autolysis in the presence of an organic solvent and an aqueous solution, thereby producing an autolysate comprising a layer comprising the organic solvent and a layer comprising an aqueous solution, wherein said layer comprising the organic solvent comprises lipids released from the microorganism during the autolysis, and wherein said layer comprising the aqueous solution comprises non-lipid materials released from the microorganism during autolysis. In particular embodiments, the method also comprises separately collecting one or both of the layer comprising the organic solvent and the layer comprising the aqueous solution (or a portion thereof on one or both). In certain embodiments, this method may comprise fermenting a fermentable sugar present in the aqueous solution to produce an alcohol. In particular embodiments, the fermenting step occurs prior to collecting one or both of the layers, but it may also be performed on a collected aqueous layer. In one exemplary embodiment, the biomass is a fungus.

Various steps of these methods are described in further detail below.

Substrate Preparation

As noted above, a wide variety of different substrates, i.e., biodegradable substrates, may be used according to the methods of the present invention. In some instances, it may be beneficial to increase the surface area to volume ratio of the substrate, thereby facilitating faster degradation of the substrate by the microorganism. The surface area of a substrate may be increased by creating smaller pieces of the substrate. A variety of methods for increasing the surface area of a solid biodegradable substrate are contemplated, and include, but are not limited to, grinding, chopping, crushing, breaking, slicing, and cutting. The surface area to volume ratio of a liquid substrate may be increased depending on the dimensions of a container holding the substrate. For example, a container having a shallow depth in comparison to the length and width has a greater exposed surface area than a container having a greater depth and has the same capacity. Maximizing the surface area of a liquid substrate may also be beneficial for gas exchange and/or for microorganisms that grow on the surface of the substrate rather than submerged. In various embodiments of methods of the present invention, the surface area of a biodegradable substrate is increased before contacting the substrate with a microorganism and/or during culture of the microorganism on the substrate.

Prior to incubating the biodegradable substrate with the microorganism, it may be desirable to sanitize, sterilize, or disinfect the substrate. Substrates may be sanitized, sterilized, or disinfected using a variety of techniques and methods depending on the type of substrate. For example, substrates may be sterilized using heat, radiation, and chemicals. Sterilization methods relying on the use of heat include, but are not limited to, steaming, autoclaving, boiling and flaming. Sterilization via irradiation includes, but is not limited to, UV irradiation, gamma irradiation, and x-ray irradiation. A wide variety of chemical compounds may be used to sanitize, sterilize, or disinfect a substrate, and examples of these chemical compounds include, but are not limited to, chlorine compounds (e.g., bleach and chlorine dioxide), alcohols (e.g., ethanol and isopropanol), ethylene oxide, ozone, aldehydes (e.g., glutaraldehyde and orthophthalaldehyde), hydrogen peroxide, acids (e.g., peracetic acid and performic acid), iodine, potassium permanganate, and phenol.

In certain embodiments, chlorine dioxide is used or applied to disinfect the substrate. Chlorine dioxide may be used as a gas, a solid in powder or tablet form, or instantaneously dissolved in water as a liquid solution. The amount and/or concentration of chlorine dioxide used may be directly related to the density of the contaminant microorganism within the substrate. Following an exposure period (e.g., about 1 to 30 minutes, about 2 to 20 minutes, about 5 to 15 minutes, or about 5 to 10 minutes) with the chlorine dioxide, the substrate may, optionally, then be exposed to UV irradiation and/or mechanical agitation to decompose the chlorine dioxide. Decomposition of the chlorine dioxide may take, for example, about 1 to 30 minutes, about 2 to 20 minutes, about 5 to 15 minutes, or about 5 to 10 minutes. The exposure time (i.e., the time from chlorine dioxide application to decomposition) is indirectly proportional to the chlorine dioxide concentration and directly proportional to the size of the contaminating microorganism (i.e., exposure time, chlorine dioxide concentration, and contaminant size are interrelated). In certain preferred embodiments, the substrate is used immediately following sterilization.

Incubation

According to certain methods of the present invention, the microorganism is cultured or incubated in contact with a biodegradable substrate for a period of time (i.e., incubation time) to allow for the degradation of the substrate and to increase the microorganism's biomass, (i.e., microbial biomass). In certain embodiments, the microorganism is cultured directly on a substrate, and in certain embodiments, the microorganism is cultured in the presence of a substrate. For example, the microorganism and substrate may both be present in a liquid solution, allowing the microorganism to contact the substrate. Typically, the liquid solution is capable of supporting growth or proliferation of the microorganism and may be, e.g., a culture medium for the microorganism used.

The microorganism is cultured or incubated in contact with the biodegradable substrate under conditions permissive of or supportive of growth or proliferation of the microorganism. The applied incubation physiochemical conditions, length of incubation, and nutritional supplements utilized during culture may be determined based upon the microorganism utilized and/or the substrate utilized. In certain embodiments, the microorganism is cultured in an environment providing optimal or near-optimal physiochemical conditions for growth. Optimization of the culture environment may include modulating, for example, temperature, humidity, and/or pH. If the biodegradable substrate does not provide all of the nutrients required for exponential growth of the microorganism, one or more nutritional supplements can be provided, such as the autolysate remnants or amino acids derived from a prior biomass. Also, various gases can be supplied to the culture environment as appropriate to maximize growth of the microorganism. For example, algae require carbon dioxide, while white rot fungi consume oxygen in order to replicate, grow, and degrade the substrate. In some instances, optimization of the culture environment may include sterilization of the substrate as described above prior to inoculation with the selected microorganism. Optimal methods for culturing various microorganisms are known in the art.

Altering incubation conditions may change the types of components produced and/or the amount or ratio of components present in the autolysate (e.g., lipids, proteins, and vitamins). Therefore, in order to produce the desired biomass components, incubation conditions may be varied to generate a greater or lesser amount of one or more components. Furthermore, incubation conditions that are suitable for one microorganism might not be suitable for another microorganism.

In order to produce the desired biomass yield, the number of cells or spores to be inoculated may determined by the cell density, specific growth rate, substrate size, and incubation area and/or volume. The microorganism is then incubated for a period of time to generate the desired biomass yield. In one embodiment, the microorganism is cultured with the substrate using optimized conditions until the end of the exponential growth phase, thereby allowing for maximum recovery of the desired lipid and non-lipid materials. The length of the incubation period may alter the types of components produced and/or the amount or ratio of components present in the autolysate (e.g., lipids, proteins, and vitamins). Therefore, in order to produce the desired biomass components, the length of incubation may be varied to generate a greater or lesser amount of one or more components. For example, longer incubation times will allow for the production of secondary metabolites (e.g., toxic materials and vitamins) by the microorganism. Thus, in certain embodiments, it is desirable to shorten the incubation period to avoid or reduce the production of toxic or harmful products. In contrast, in certain other embodiments it is desirable to lengthen the incubation period to generate a greater amount of a certain product. Therefore, the incubation conditions and time may be optimized to generate the desired components from the biomass.

In certain embodiments, the Area Growth Rate (AGR), defined as:

$$AGR=biomass\ dry\ weight/unit\ area/incubation\ period$$

is equal to or greater than 20 grams/square meter/week, equal to or greater than 25 grams/square meter/week, equal to or greater than 30 grams/square meter/week, equal to or greater than 35 grams/square meter/week, equal to or greater than 40 grams/square meter/week, equal to or greater than 45 grams/square meter/week, equal to or greater than 50 grams/square meter/week, equal to or greater than 55 grams/square meter/week, equal to or greater than 60 grams/square meter/week, or equal to or greater than 65 grams/square meter/week.

At the end of the incubation period, the biomass is harvested. The biomass may be considered to be either collectible or uncollectible. A collectible biomass is a biomass easily isolated from any remaining substrate. Filamentous fungi and algae are examples of collectible biomasses. In one embodiment, harvesting a collectible biomass may be accomplished by mechanically collecting the biomass into a separate container, for example, by manual or automated means. The collected biomass may be broken into smaller pieces by, for example, chopping, grinding or slicing.

In other embodiments, a collectible biomass present in a liquid solution is harvested by separating the liquid solution containing the biomass from any remaining substrate. The collectible biomass may be left in the liquid solution and subjected to autolysis, or the collectible biomass may be harvested from the liquid solution, e.g., by centrifugation, sedimentation, or filtration. In one embodiment, microorganisms in a liquid substrate may be collected using centrifugation or filtration.

In other embodiments, an uncollectible biomass is harvested. Uncollectible biomasses, for example, bacteria and yeast in a liquid substrate, may be left in the aqueous solution when collection methods such as centrifugation, sedimentation, and filtration are not practical. Uncollectible biomasses, for example, bacteria and yeast in a liquid substrate, may be left in their aqueous solutions (i.e., filtrate) when collection methods such as centrifugation, sedimentation, and filtration are not practical.

As discussed above, in certain embodiments, the microorganism is cultured with a substrate in a liquid medium, or the microorganism is cultured with a liquid substrate. Following introduction of the microorganism to the liquid (i.e., a medium containing the substrate or a liquid substrate) and culturing, the liquid will contain soluble products of substrate hydrolysis and soluble products released by the microorganism, such as, e.g., extracellular or secreted proteins or enzymes. This resulting liquid, which contains soluble products of substrate hydrolysis and soluble products release by the microorganism, is referred to herein as the "filtrate." In certain instances, it may be desirable to obtain these soluble products. Accordingly, in particular embodiments of the methods of the present invention, the filtrate is collected together with the microbial biomass, together or separately. For example, when culturing filamentous fungi on a solid substrate in the presence of a liquid medium, the liquid medium from the culture will contain a soluble hydrolysate of the substrate that is in solution (e.g., soluble products), and the liquid medium, or filtrate, may be collected in addition to the biomass.

Autolysis

Once the microorganism or biomass has been harvested, it is subjected to autolysis. Autolysis (i.e., the destruction and break down of a cell by the action of its own enzymes, e.g., after its death) of a microorganism is a natural phenomenon that normally starts around the end of the senescent phase of the growth curve. Inducing autolysis comprises the deliberate initiation of autolysis, typically prior to when it would naturally occur. For example, autolysis may be initiated near the end of the exponential phase of the microorganism's growth curve.

Initiation of Autolysis

There are numerous ways to initiate or induce cellular autolysis of the biomass, and the present invention contemplates the use of any such method. In particular embodiments, inducing autolysis comprises either killing microorganisms of the biomass or inducing a process leading to killing of microorganisms of the biomass. Various exemplary techniques for inducing autolysis of the biomass (i.e., "killing techniques" or "autolysis initiation methods") include, but are not limited to, mechanical, chemical, ultrasonic, enzymatic, and/or thermal methods. Some methods of initiating autolysis are distinctive to specific organisms (e.g., placing algae in a dark environment), while others are non-specific (e.g., sterilization methods); some are relatively expensive (e.g., ultrasonication), while others are inexpensive (e.g., chemical compounds); some are fast (e.g., chlorine containing compounds), while others are slow (e.g., starvation); some have undesirable effects on the cellular components of the microorganism (e.g., hydrogen peroxide), while others do not adversely affect the cellular components (e.g., homogenization); and some kill spores (e.g., chlorine compounds), while others do not kill spores (e.g., homogenization).

The technique or mechanism chosen to initiate autolysis will depend on the microorganism, and it may also be an economic decision (e.g., the cost of necessary supplies and length of time required for autolysis). In certain embodiments, one or more of the techniques described above can be used to initiate autolysis (e.g., chemical or a combination of chemical and thermal). If a combination of autolysis induction methods is used, the different methods can be used simultaneously or in succession.

The killing dosage (i.e., concentration, intensity, and/or exposure time) used to initiate autolysis of a biomass is a function of the autolysis initiation method, the utilized microorganism, and the size and surface area of the biomass (e.g., original size or chopped). In certain embodiments, a preferred killing dosage maximizes the autolysis, while minimizing processing time and undesired effects on cellular components of the microorganism (e.g., chlorination of amino acids and/or oxidation of glucose).

Some materials used in the selected method of inducing autolysis may have one or more adverse effects on cellular components. Therefore, when such a method of inducing autolysis is used, it may be desirable to halt the method once the biomass has undergone autolysis. For example, a chemical compound used to induce autolysis that has adverse effects on cellular components, such as lipid or non-lipid products, may be inactivated following the initiation of autolysis or following a period of autolysis, and before the products are substantially adversely affected. Thus, according to certain embodiments, when the exposure time or the initiation of autolysis is completed, as determined by routine methods and previous experience, the adverse effect is halted or stopped. Stopping the adverse effect can be accomplished by, for example, inhibiting, inactivating, neutralizing, decomposing, and/or removing the source of the adverse effect. In particular embodiments, autolysis initiation using materials with adverse effects on the cellular components that cannot be halted or stopped are excluded from the present invention or not performed according to methods of the present invention. In particular embodiments, toxic compounds that are inhibitors and deactivators capable of halting an adverse effect are excluded from or not used according to the methods of the present invention. In addition, in particular embodiments, autolysis initiation methods, materials, and halting compounds that generate toxic compounds from any of the cellular components are excluded from or not used according to the methods of the present invention.

In certain embodiments, autolysis is initiated by contacting the biomass with chlorine dioxide. Using chlorine dioxide to initiate autolysis is relatively inexpensive and quick, and chlorine dioxide exhibits biocidal activity over a wide pH range from about 3 to 10. In addition, chlorine dioxide does not chlorinate organic compounds, unlike chlorine, and it will not react with natural organic matter in solution to form trihalomethanes or other chlorinated byproducts. Furthermore, chlorine dioxide does not react with ammonia or form chloramines. It is believed that chlorine dioxide induces autolysis by disrupting protein synthesis, and it is capable of killing spores, unlike some other methods of inducing autolysis.

At the end of the initiation of autolysis, the biomass has been killed or at least substantially killed and cellular autolysis, or breakdown, begins or occurs. Autolysis is then allowed to proceed for a suitable duration of time to allow release of most or a substantial amount of lipid and non-lipid products from the biomass, the time period depending in part upon the microorganism being used, as discussed below.

The initiation of autolysis may be performed on a biomass in a liquid solution, e.g., an aqueous solution. In addition, the initiation of autolysis may be performed in the presence of a liquid solution and an organic solvent, as discussed in further detail below.

Organic Solvent

In order to isolate lipids released from the microorganism during autolysis, an organic solvent, such as hexane, is added to the biomass following incubation with the biodegradable substrate. The solvent may be added to the biomass prior to the initiation of autolysis, during autolysis, or following autolysis. In certain embodiments of the invention, the addition of the organic solvent occurs simultaneous with the initiation of autolysis or shortly thereafter. If desired, the organic solvent may be added to the biomass and/or autolysate at multiple time points.

Examples of organic solvents that may be used include, but are not limited to, benzene, ethyl ether, ethylene oxide, glycerin, alkanes such as hexane, isopropyl alcohol, ketones such as acetone, propylene glycol ethers, toluene, and xylene. In particular embodiments of the invention, the organic solvent is hexane. Non-water soluble cellular components, such as certain lipids, will dissolve in the organic solvent.

For example, in one particular embodiment, a collectible biomass is collected and finely chopped and ground in a suitable amount of hexane. About 0.2 g to about 0.4 g of chlorine dioxide in solid form is dissolved in each liter of an aqueous solution. In certain embodiments, the aqueous solution may be contaminated (e.g., with microorganisms and/or heavy metals), uncontaminated fresh or salt water, or it may be the filtrate or substrate's hydrolysate. A suitable amount of the aqueous solution, filtrate, or substrate's hydrolysate (e.g., the total amount of the substrate's hydrolysate), is added to the hexane solution. Chopping, grinding, and chlorine dioxide initiate induced autolysis. Following an exposure time of about 5 to about 15 minutes, the solution is agitated for about 5 to about 10 minutes to decompose the chlorine dioxide. Alternatively, sterile air or oxygen is bubbled through the solution to decompose the chlorine dioxide. Next, the solution may be irradiated with UV light for about 5 minutes to fully decompose the chlorine dioxide and sterilize the solution. Following the decomposition of the chlorine dioxide, any glucose oxidase enzymes present may optionally be blocked as described below.

Inhibiting Cellular Glucose Oxidase

Some microorganisms produce glucose oxidase endoenzymes. These microorganisms may release glucose oxidase during autolysis, and it can oxidize glucose, which is a non-lipid material that may be produced according to the present invention. Accordingly, in particular embodiments, cellular glucose oxidases are inhibited to prevent or reduce oxidation of glucose. One method of inhibiting glucose oxidase relies on the addition of hydrogen peroxide ($H_2O_2$) to the biomass. Hydrogen peroxide oxidizes both glucose oxidase and glucose, and it can be utilized to block the oxidation of glucose by glucose oxidase. Hydrogen peroxide is also a bleaching agent and can be utilized to bleach or discolor the autolysate. Hydrogen peroxide first oxidizes any glucose oxidase present in the solution, so in particular embodiments, it is neutralized before it begins oxidizing glucose.

Accordingly, in certain embodiments of methods of the present invention, hydrogen peroxide is added to the biomass during the initiation of autolysis or to the biomass, lysate and/or autolysate during the time period of autolysis following the initiation of autolysis. In particular embodiments, hydrogen peroxide is added to the hexane and aqueous solution mixture containing the biomass, concurrent with or following the initiation of autolysis (e.g., following the decomposition of chlorine dioxide when used). However, the hydrogen peroxide dosage and exposure time may be readily determined for each combination of microorganism and substrate, the size and any processing (i.e., chopping) of the biomass, and other factors (e.g., volume, concentration, and exposure time). In certain embodiments, hydrogen peroxide is added to achieve a concentration in the aqueous solution equal to about 0.5 ml, about 1.0 ml, about 1.5 ml, about 2.0 ml, about 2.5 ml, about 3.0 ml, about 4.0 ml, about 5.0 ml, or about 10.0 ml of 30% hydrogen peroxide per liter of aqueous solution. In certain embodiments, the hydrogen peroxide exposure time is about 30 minutes, about 1 hour, about 2 hours, about 4 hours, or about 8 hours. The hydrogen peroxide may be subsequently neutralized to prevent or reduce the oxidation of glucose.

In one particular example, about 1.5 ml of 30% hydrogen peroxide per liter of aqueous solution is added to the hexane-aqueous solution mixture containing the biomass immediately following the initiation of autolysis (e.g., following the decomposition of chlorine dioxide). The hydrogen peroxide may then be neutralized by adding about 7.1 g of sodium bicarbonate per liter of aqueous solution to prevent it from oxidizing the glucose. In particular embodiments, the hydrogen peroxide exposure time is about one hour.

In certain embodiments, it is useful to add hydrogen peroxide to the biomass even if the microorganism does not produce glucose oxidase enzymes. For example, hydrogen peroxide will kill almost all (e.g., about 90%, about 95%, about 99%, or more) of any microorganisms that remain alive following autolysis, and it can be used to bleach, i.e., discolor, pigment found in the biomass.

Completion of Autolysis

A period of time is needed to complete autolysis. The duration of autolysis depends on the species of microorganism utilized, size of the biomass, autolysis initiation method, killing dosage, and temperature. Therefore, autolysis may take a period of weeks, days, hours, or minutes depending on the above factors. In certain embodiments, the biomass is incubated for a period of about 0 to about 120 hours following the induction of autolysis. For example, a hexane-aqueous solution mixture comprising the biomass may be incubated for a period of about 0 to about 120 hours or about 0 to about 36 hours at a temperature of about 25° C. to about 45° C. following the induction of autolysis and inhibition of glucose oxidase.

Autolysis may be accelerated in order to generate a greater yield in the same amount of time or from a smaller volume of starting materials. Both situations have a positive economical impact. Autolysis acceleration may be conducted by adding, for example, a compound to the autolysis mixture, biomass, or autolysate. Compounds that may be used for accelerating autolysis include, but are not limited to, sodium chloride, ethanol, toluene, ethyl acetate, aliphatic carbonic acids, acetic acid, thiamine and pyridoxine. If a fermentation step will be included concurrently or subsequently, care should be taken to confirm that the added compound will not negatively affect the fermentation conditions.

During autolysis, as certain cellular lipids are released from the cell, they join and dissolve in the organic solvent layer, e.g., a hexane solution. Polysaccharides and starches are hydrolyzed during autolysis to simple monosaccharides that dissolve in the aqueous layer as they are released from the cell. Other cellular components such as organic and inorganic acids, polyhydric alcohols, sugar related compounds, nitrogenous compounds, and enzymes will also be found in the main aqueous solution after the completion of autolysis.

Autolysate

The end product of autolysis is the autolysate, which comprises two layers. The first autolysate layer is the organic solvent solution containing cellular lipids (e.g., micelles), which may also be referred to as the "organic solvent layer," the "non-aqueous layer" or the "lipid layer." This non-aqueous layer is less dense than and floats on top of the second autolysate layer (i.e., the "aqueous layer"), thereby isolating and protecting the aqueous layer from penetration and contamination by environmental microorganisms.

The organic solvent layer (lipid layer) of the autolysate comprises lipids and fatty acids soluble in the organic solvent. Examples of fatty acids found in the lipid layer include, but are not limited to, caprylic C8, capric C10, lauric C12, tridecanoic C13, C15 pentadecanoic, palmitic C16, C17 heptadecanoic, oleic C18:1, stearic C18, and linoleic C18:2.

The aqueous layer of the autolysate is an aqueous solution that contains water soluble cellular breakdown products such as simple fermentable sugars, amino acids, peptides, organic and inorganic acids, polyhydric alcohols, sugar related compounds, nitrogenous compounds, and enzymes. This layer also contains lipids and fatty acids, including but not limited to, lauric C12, myristic C14, C15 pentadecanoic, C16:1 palmitoleic, palmitic C16, C17 heptadecanoic, oleic C18:1, stearic C18, linoleic C18:2, linolenic C18:3, arachidic C20, and behenic C22 fatty acids. In addition, the aqueous layer also contains antibiotics, macro and micro nutrients, glucose; organic acids, such as, e.g., oxalic acid, citric acid, N, Methylanilin, pyridine, and benzoic acid; elements, such as, e.g., carbon, oxygen, sodium, clorine, potassium, calcium, and zinc; amino acids, such as, e.g., phosphoserine, taurine, aspartic acid, threonine, serine, glutamic acid, proline, glycine, alanine, valine, methionine, isoleucine, leucine, tyrosine, phenylalanine, beta-aminoisubutyric acid, carnosine, ornithine, lysine, and arginine; and phenolic compound, such as, e.g., ferulic acid, gallic acid, and coumaric acid, and the compounds 1,4-diacids (succinic, fumaric and malic); 2,5-furan dicarboxylic acid; 3-hydroxy propionic acid; glucaric acid; itaconic acid; levulinic acid; 3-hydroxybutyrolactone; glycerol; sorbitol; xylitol/arabinitol; aspartic acid; and glutamic acid.

In some embodiments, the biomass is collectible and the lower autolysate layer may contain traces of the substrate and residual microorganism cells or particulates. In certain embodiments wherein the biomass is uncollectible, the lower aqueous layer may contain any remaining substrate. The upper non-aqueous layer will contain lipids and other cellular components soluble in the organic solvent.

Storing the Autolysate

The autolysate resulting from the methods of the invention is the foundation for numerous bioproducts and comprises lipids and non-lipid materials that may be further isolated or purified to yield valuable products or intermediates used in the production of valuable products. Such further product isolation may be performed immediately following the above methods of the present invention, or the autolysate may be stored for later use. As indicated above, the addition of the organic solvent generates two layers in the autolysate, and the upper organic solvent layer protects the lower aqueous layer. Also, the addition of hydrogen peroxide to inhibit glucose oxidases and its subsequent neutralization, for example, by adding sodium bicarbonate before it starts oxidizing the glucose, further preserves the components of the autolysate for storage.

Following the completion of autolysis, the autolysate may be stored short or long term, e.g., at ambient temperature or at a temperature below 10° C. In particular embodiments, the autolysate is stored at ambient temperature for less than 48 or 72 hours. In certain embodiments, the autolysate may be stored at a temperature below 10° C. for at least 24 hours, at least 48 hours, at least 72 hours, at least 4 days, at least 5 days, at least 1 week, at least 2 weeks, at least 1 month, at least 2 months, at least 4 months, at least 6 months, or at least one year. In certain embodiments, the storage temperature is 2-3° C. Also, in one embodiment, the autolysate may be stored and/or transported (e.g., via pipeline) at ambient temperature for up to 36 hours. The autolysate may be stored or transported with both layers present, or the two layers may be separated before storage or transport.

Separating the Autolysate Layers

As described above, the upper non-aqueous autolysate layer comprises the organic solvent and lipids derived from the biomass. The upper layer may be separated from the lower aqueous autolysate layer by, for example, decanting or skimming. In another embodiment, layers are separated using a separation device, e.g., a device described herein. In certain embodiments, the separation device is a container that holds both the non-aqueous layer and the aqueous layer of the autolysate, which allows for the removal of the upper non-aqueous layer, e.g., by a means located to the top of the container and/or which allows for the removal of the lower aqueous layer, e.g., by a means located to the bottom of the container. Such a device may be referred to as a separation tower or autolysate tower. In particular embodiments, the lower aqueous layer present in a separation tower (i.e., an autolysate tower) is drained to separate it from the upper lipid-containing autolysate layer. In certain embodiments, the separation and/or autolysate tower further comprises the properties of a fermentor. Exemplary devices are depicted in the accompanying Figures.

Once the non-aqueous layer has been separated from the aqueous layer, the organic solvent can be separated from the lipids (e.g., micelles), for example, via evaporation and condensation. In this way, the lipids are isolated and the organic solvent can be recycled for use in collecting lipids and other components from the autolysate of a subsequent biomass. In certain embodiments, the organic solvent is hexane, and the low boiling point of hexane (67° C./152° F.) and the high solubility of lipids in hexane are exploited in the process.

Following separation of the autolysate layers, one or both of the autolysate layers may be further processed to isolate or purify valuable products or intermediates to produce biofuel and other products. In one embodiment, both autolysate layers are further processed to isolate or purify valuable products or intermediates to produce biofuel and other products. In particular embodiments, one or more products, e.g., total lipids, in either layer are isolated or purified such that they are at least 75%, at least 85%, at least 90%, at least 95%, at least 98%, at least 99%, at least 99.5%, or at least 99.9% pure. The valuable products and intermediates may be isolated from the autolysate layers using one or more available techniques including, but not limited to, evaporation, condensation, electrophoresis, chromatography, membrane separation, and centrifugation.

Production of Biofuel and Other Products

In some embodiments, lipids and non-lipid materials are isolated from the autolysate layers, once the layers have been separated. In other embodiments, lipid and non-lipid materials can be further processed and generated in the autolysate prior to the separation of the two layers. In this way, additional valuable bioproducts may be generated during or following autolysis within the autolysate and/or filtrate. For example, simple sugars present in the autolysate may be fermented during or following autolysis by the introduction of yeast or bacteria to the aqueous layer of the autolysate. The autolysis conditions may be adjusted in order to generate more of the desired product, e.g., an anaerobic environment in order to enhance fermentation. In other embodiments, the lipid and non-lipid materials are further processed and generated in the aqueous layer or the organic solvent layer once the layers have been separated. In other embodiments, a product or starting material may be isolated from the autolysate prior to any further processing.

Once isolated from the organic solvent, the lipids can be utilized to produce biodiesel (e.g., methyl ester and/or ethyl ester) by methods known in the art. In particular, biodiesel may be generated from the transesterification of the lipids recovered from the autolysate. Biodiesel generated by transesterification comprises a mix of mono-alkyl esters of long chain fatty acids. The most common form of biodiesel is derived from methanol and contains methyl esters because methanol is the cheapest alcohol available, although ethanol can readily be used to produce an ethyl ester biodiesel. Glycerol is a byproduct of the transesterification process, and the ratio of biodiesel to glycerol is typically about 9:1. Transesterification may be carried out by any one of the methods known in the art, such as alkali-, acid-, or lipase-catalysis (see, e.g., Singh et al. Recent Pat Biotechnol. 2008, 2(2):130-143). Various methods of transesterification utilize, for example, use of a batch reactor, a supercritical alcohol, an ultrasonic reactor, or microwave irradiation (Such methods are described, e.g., in Jeong and Park. Appl Biochem Biotechnol. 2006, 131(1-3):668-679; Fukuda et al. Journal of Bioscience and Engineering. 2001, 92(5):405-416; Shah and Gupta. Chemistry Central Journal. 2008, 2(1):1-9; and Carrillo-Munoz et al. J Org. Chem. 1996, 61(22):7746-7749).

The aqueous autolysate layer comprises water soluble cellular breakdown products such as simple fermentable sugars, amino acids, peptides, organic and inorganic acids, polyhydric alcohols, sugar related compounds, nitrogenous compounds, and enzymes. Following the separation of the two autolysate layers, components of the aqueous layer may be isolated by methods known in the art. Once the desired components have been isolated, they can then be used to generate various products such as hydrogen fuel or ethanol.

For example, hydrogen may be generated from glucose contained in the aqueous layer. Glucose may be separated by, for example, liquid chromatography, out of the autolysate aqueous layer. The isolated glucose may then be converted to hydrogen and carbon dioxide, e.g., by a synthetic enzymatic pathway using eleven synthetic enzymes, rather than the thirteen enzymes required for "agricultural" starch utilized in the study by Zhang et al. (PLoS ONE 2(5): e456. doi:10.1371/journal.pone.0000456). In addition, chemical catalysis of glucose to hydrogen and carbon dioxide can be achieved without synthetic enzymes at high temperatures, e.g., around 500 K (Cortright et al. Nature. 2002, 418: 964-967). However, utilizing the synthetic enzyme pathway allows for the production of hydrogen at a high yield under mild conditions and is, therefore, an efficient method of producing hydrogen fuel from the autolysate-derived glucose in a cost effective manner. The hydrogen fuel generated from the autolysate can be used for a variety of applications including, but not limited to, fueling cars, trucks, and trains. Hydrogen produced, e.g., by the enzymatic pathway, can be used immediately as fuel. The carbon dioxide generated in the process can be stored in an acrylic plastic cylinder using a compressor. The stored carbon dioxide can be utilized in various applications, including cell culture. For example, carbon dioxide generated from the autolysate components can be recycled for the cultivation of an algal biomass.

Simple sugars, such as glucose, fructose, and sucrose, contained in the aqueous layer of the autolysate can be fermented to generate ethanol, butanol, acetone, and/or isopropanol. Fermentation is the biological process by which simple sugars such as glucose, fructose, and sucrose are converted into cellular energy and generate alcohol, such as ethanol, and carbon dioxide as metabolic waste products. The sugars may be isolated from the aqueous layer as described above for glucose. In other embodiments, the sugar molecules remain in the aqueous layer, and they may also be concentrated.

The yeast species *Saccharomyces cerevisiae* has been used in fermenting alcoholic beverages for thousands of years and can be utilized to generate ethanol from the sugars contained in the autolysate. In addition, the bacterium *Zymomonas mobilis* is notable for its ethanol producing capability, which surpasses that of *S. cerevisiae* in some aspects (e.g., greater ethanol yield). Microorganisms including, but not limited to, *S. cerevisiae* and *Z. mobilis* may be utilized herein to ferment the sugars (i.e., with or without glucose) contained in the aqueous layer of the autolysate to generate ethanol and carbon dioxide. The emitted carbon dioxide can be stored and utilized as described above. Ethanol is separated from the media by, for example, distillation or pervaporation. The isolated ethanol can then be stored and utilized in various applications, such as a biofuel for motor vehicles.

Some simple sugars within the autolysate are fermented by bacteria including, but not limited to, *Clostridium beijerinckii* (*C. butylicum*), *C. acetobutylicum*, and *C. tetanomorphum* to produce butanol, acetone, isopropanol and/or ethanol. Butanol can be isolated from the aqueous solutions and/or fermentation broth by, for example, steam stripping distillation, adsorption, gas stripping, and pervaporation. The isolated butanol can then be stored and utilized in various applications, including as a biofuel or a solvent.

Remaining valuable materials include, but are not limited to, amino acids, vitamins, antibiotics, elements, phenolic compounds, enzymes, polyhydric alcohols, sugar-based compounds, nitrogenous compounds, and organic and inorganic acids. These valuable materials can be separated, purified, or isolated by using, for example, electrophoresis, chromatography, membrane separation processes, and centrifugation.

Isolated amino acids and peptides can be utilized in nutritional supplements for humans, animals, plants and microorganisms (e.g., fertilizers, livestock feed, and culture media). Using amino acids as a substitute for chemical fertilizers has been shown to result in a 15-20% increase in crop yield and a decrease in emission of nitrogen oxides into the environment.

Enzymes isolated from the autolysate have a variety of industrial uses. For example, lipases derived from the autolysate can be used in a detergent. The compounds 1,4-diacids (succinic, fumaric and malic); 2,5-furan dicarboxylic acid; 3-hydroxy propionic acid; glucaric acid; itaconic acid; levulinic acid; 3-hydroxybutyrolactone; glycerol; sorbitol; xylitol/arabinitol; aspartic acid; and glutamic acid are sugar-based compounds selected by the Pacific Northwest National Laboratory, the National Renewable Energy Laboratory, and the Energy Efficiency and Renewable Energy Program (EERE), for the EERE Office of the Biomass Program, as the 12 chemical building blocks. These building blocks are found in and/or converted from compounds within the autolysate of the microorganism. These valuable building blocks are subsequently converted into a number of high value bio-based chemicals and materials that may be used to generate a wide variety of bioproducts including, but not limited to, solvents, fuels, antifreeze and deicers, emulsifiers, chelating agents, plasticizers, pH control agents, resins, polyacrylates, polyacrylimides, polyethers, polypyrrolidones, polyesters, polyamides (e.g., nylons), polycarbonates, polyurethanes, and polysaccharides. These bioproducts can be utilized in a variety of industries including, but not limited to, transportation, textiles, food supply, environment, communication, housing, recreation, and health and hygiene (see, e.g., Werpy and Petersen, eds. Top Value Added Chemicals from Biomass: Volume 1—Results of Screening for Potential Candidates from Sugars and Synthesis Gas [online], [Retrieved on May 18, 2009]. Retrieved from the Internet: <URL: www1.eere.energy.gov/biomass/pdfs/35523.pdf>1).

For example, 2,5 furan dicarboxylic acid may be generated by the oxidative dehydration of six carbon sugars (e.g., glucose). In addition, glucose can be hydrogenated to produce sorbitol. Similarly, xylose can be hydrogenated to produce xylitol. The oxidative degradation of starches (e.g., via hydrogen peroxide) results in the production of 3-hydroxybutyrolactone (Werpy and Petersen, eds. supra). Alternatively, glucose can be oxidized with nitric acid to produce glucaric acid. The distillation of citric acid generates itaconic acid. Levulinic acid may also be generated from glucose as described by Girisuta et al. (*Chemical Engineering Research and Design*, 2006; 84(A5):339-349). 3-hydroxypropionic acid can be generated from glycerol (see, e.g., U.S. Pat. No. 6,852,517). It would be readily apparent to the skilled artisan that glucose, xylose, and citric acid are found in the autolysate.

Products obtained from the autolysate have a variety of valuable uses, including, but not limited to the examples that follow. Gallic acid is an antioxidant and protects cells against oxidative damage. It has also been shown to be cytotoxic against cancer cells, without harming healthy cells. In addition, it is used as a remote astringent in cases of internal haemorrhage, used to treat albuminuria and diabetes, and used for making dyes and inks. Glutamic acid, asparatic acid, alanine, valine and leucine are amino acids needed by plants. Lysine, methionine and threonine are amino acids needed by animals as food supplement. Carnosine has been shown to retard cancer growth and protect against alcohol-induced oxidative stress and ethanol-induced chronic liver damage. Isoleucine is known for its ability to increase endurance and help heal and repair muscle tissue and encourage clotting at the site of injury. Benzoic acid is an important precursor for the synthesis of many other organic substances. Benzoic acid and its salts are used as a food preservative. Benzoic acid is a constituent of Whitfield's Ointment, which is used for the treatment of fungal skin diseases such as tinea. Pyridine is an important solvent and reagent in organic synthesis, and it is the precursor to myriad insecticides, herbicides, pharmaceuticals, food flavorings, dyes, rubber chemicals, adhesives, paints, explosives and disinfectants. Oxalic acid is used as a cleaning agent, especially for the removal of rust or removal of iron from minerals specimens. Many household chemical products contain oxalic acid. About 25% of produced oxalic acid is used as a mordant in dyeing processes. Oxalic acid is also used in bleaches and is an important reagent in lanthanide chemistry. Oxalic acid is used in the restoration of old wood. Citric acid is used as a flavoring and preservative in food and beverages, especially soft drinks. Citric acid's ability to chelate metals makes it useful in soaps and laundry detergents. Citric acid is the active ingredient in some bathroom and kitchen cleaning solutions. Citric acid is used in biotechnology and the pharmaceutical industry. In certain industries, it is used to dissolve rust from steel. Linolenic acid, an n-3 fatty acid, is a member of the group of essential fatty acids, so called because they cannot be produced within the body and must be acquired through diet. Studies have found evidence that linolenic acid is related to a lower risk of cardiovascular disease. Dietary linolenic acid has been assessed for its role in cardiovascular health.

Linoleic acid has become increasingly popular in the beauty products industry because of its beneficial properties on the skin. Linoleic acid is also used in making soaps, emulsifiers, and quick-drying oils. Oleic acid may help boost memory. One of the most important aromatic amines is aniline. Aniline is the starting material in the dye manufacturing industry and as in the manufacture of others. Aniline is converted into sulfanilic acid which is the parent compound of the sulfa drugs. N-methylaniline or aniline is also important in the manufacture of rubber-processing chemicals, antioxidants and varnishes.

In addition to obtaining lipid and non-lipid materials from the autolysate of the biomass, it is also contemplated herein that these valuable materials may be produced indirectly, for example, in the media. In this way, the microorganism produces the desired product by extracellular secretion or by hydrolyzing or fermenting the substrate into the medium.

For example, succinic acid is a fermentation product of a variety of microorganisms including *Actinobacillus succinogenes, Anaerobiospirillum succiniciproducens, Mannheimia succiniciproducens*, and recombinant *E. coli* (Song and Lee. *Enzyme and Microbial Technology*, 2006; 39(3): 352-361.). Fungi are known for their organic acid-producing capability and have been used in fermentation processes to generate fumaric acid. Among these strains, *Rhizopus* species (i.e., *R. nigricans, R. arrhizus, R. oryzae*, and *R. formosa*) yield the greatest amount of fumaric acid under aerobic and anaerobic conditions (see, e.g., Engel et al. *Appl Microbial Biotechnol*, 2008; 78:379-389). The production of malic acid by fermentation has been observed for a wide range of microorganisms, and it has been most successfully demonstrated with *Aspergillus flavus* and *Saccharomyces cerevisiae* (Zelle et al. *Applied and Environmental Microbiology*, 2008; 74(9):2766-2777). It has also been demonstrated that itaconic acid is a fermentation product of an *Aspergillus terreus* mutant strain (U.S. Pat. No. 6,171,831) and *Aspergillus itaconicus* (Ainsworth. *Introduction to the History of Mycology*. Cambridge University Press, New York, 1976). However, as noted above, the distillation of citric acid produces itaconic acid, and it is well known that citric acid can be produced by *Aspergillus niger* on an industrial scale. Tada et al. demonstrated that *Candida magnoliae* are capable of producing xylitol by fermenting corn cob hydrolysate containing hemicellulose (*Journal of Bioscience and Bioengineering*, 2004; 98(3):228-230). Arabinitol is also a fermentation product of yeast, including *Candida albicans, C. tropicalis, C. parapsilosis, C. pseudotropicalis*, and *Torulopsis glabrata* (Bernard et al. *Journal of Clinical Microbiology*, 1981; 14(2):189-194).

In addition to utilizing microorganisms to generate the above fermentation products in the medium along with the lipid and non-lipid materials in its autolysate, it should also be noted that it is contemplated herein to utilize a microorganism biomass that is considered a waste product in certain industries. For example, the yeast, fungi, and bacteria used in the manufacture of products in the pharmaceutical, brewing, and fermentation industries can be autolysed as described herein to generate lipid and non-lipid materials. Therefore the waste byproducts generated in these processes are no longer considered waste products, but rather a source of further valuable materials.

In certain embodiments where it is undesirable or not feasible (e.g., necessary separation equipment is not available) to isolate the remaining materials, the remaining aqueous layer of the autolysate can be used as a nutritional supplement for animals and/or plants, or it could be recycled as a nutritional supplement for culturing a microorganism.

Fresh water and/or purified water may also be produced utilizing the present invention. In particular embodiments, intracellular water isolated from an autolysate is free of impurities and is a source of potable fresh water. Extracellular water may be biologically, toxically, or poisonously contaminated water. Accordingly, the present invention includes methods of producing fresh water or pure water by utilizing salt water or contaminated water when culturing the microorganism on a biodegradable substrate in solution.

In certain embodiments, the contaminated water is treated before it is added to media used to culture the microorganism. In other embodiments, the microorganism is tolerant to the contaminant, and the contaminated water can be added to the media used to culture the microorganism without treatment. Contaminated extracellular water may be purified so that some or all of the impurities are removed.

For example, microorganisms may be incubated with a biodegradable substrate in the presence of water that is not fresh or is contaminated with impurities and then subjected to autolysis as described herein. Fresh water or water that is purified from some or all of the impurities may then be obtained from the autolysate. Additionally, the biodegradable substrate may contain water that is not fresh or is contaminated with impurities (e.g., irrigation water), and this water may be taken up by a microorganism incubated with the biodegradable substrate. Following autolysis of the microorganism, fresh water or water purified from some or all of the impurities may be obtained from the autolysate. Following the methods of the present invention, one ton of rice straw utilized as a substrate by fungi is expected to produce about 28.5 tons of fresh water from the microorganism's cultivating media, which contains irrigation water stored in the rice straw. Accordingly, it is expected that one acre of rice straw would produce, using the technology of the present invention, 100-114 tons of fresh water, with each acre producing 3.5-4 tons of rice straw.

Accordingly, the present invention includes a method for producing fresh water or purified water from various water sources, such as, e.g., agricultural waste, waste water, or brackish or salt water. Waste water can include any water that has undergone human influence. It includes liquid waste released from domestic and commercial properties, industry, and/or agriculture and can encompass a wide range of possible contaminants at varying concentrations. In certain embodiments, waste water may be contaminated with one or more toxins and be considered poisonous or toxic. Salt water typically ranges in salinity between 3.1% and 3.8%, the average being 3.5%, and this is mostly, but not entirely, made up of sodium chloride (NaCl) ions. Brackish water has more salinity than freshwater, but not as much as seawater. Brackish water typically contains between 0.5% and 3% salinity. With respect to salinity, fresh water typically has less than 0.5% salinity. In one embodiment, fresh water has less than 500 parts per million (ppm) of dissolved salts.

In one embodiment, fresh water is produced by culturing or incubating a microorganism with a biodegradable substrate in the presence of brackish or salt water, inducing autolysis of the microorganism, allowing the biomass to undergo autolysis, collecting the resulting autolysate, and isolating fresh water from the autolysate, according to procedures described infra, e.g., evaporation and condensation. In particular embodiments, the fresh water is isolated by purifying other products from the autolysate, leaving fresh water as a byproduct. Without wishing to be bound by theory, it is believed that when the microorganism is cultured or incubated with the biodegradable substrate in the presence of brackish or salt water, the microorganism takes up and desalinates some of this water. Following autolysis, fresh water may be obtained from the autolysate.

Fresh water obtained from culturing a biomass in brackish or salt water may be used to water plants and crops. In one embodiment, the water obtained from the aqueous layer of the autolysate has a reduced salt content in comparison to the brackish or salt water, and organic fertilizers can be dissolved in the water with reduced salt content. In a related embodiment, irrigation water is added to the aqueous layer with the reduced salt content thereby further reducing the salinity of the solution, and the amino acids present in the autolysate help plants overcome stress due to the salinity of the solution. In a related embodiment, purified water is produced by culturing or incubating a microorganism with a biodegradable substrate in the presence of waste water or contaminated water, inducing autolysis of the microorganism, allowing the biomass to undergo autolysis, collecting the resulting autolysate, and isolating purified water from the autolysate, according to procedures described infra. In particular embodiments, the purified water is isolated by purifying other products from the autolysate, leaving purified water as a byproduct. In particular embodiments, the microorganism is cultured or incubated with the biodegradable substrate in the presence of waste water or contaminated water, and the microorganism takes up and decontaminates some of this water. Following autolysis, pure water may be obtained from the autolysate.

It is understood that the term "purified water" indicates that the water contains less of one or more contaminants. In particular embodiments, it contains less than 75%, less than 50%, or less than 25% of one or more contaminants as compared to the level before being subjected to a method of the present invention. The pure water may be partially purified, e.g., such that it is useful for agricultural use, e.g., irrigation, or it may be substantially purified, e.g., such that it is suitable for drinking by animals.

In addition, it is understood that when a microorganism is cultured or incubated with a biodegradable substrate in the presence of brackish water, salt water, waste water or contaminated water, the water may be present in the cultivating media and/or it may be present in the biodegradable substance. In both cases, the water is taken up by the microorganism, which is then used to produce autolysate from which fresh water is obtained.

In certain embodiments, the methods of the present invention may also be used to retrieve the irrigation water stored in agricultural waste, thus effectively recycling the irrigation water. For example, irrigation water present in feedstock, e.g., agricultural crops or agricultural waste, may be retrieved from autolysate following the culturing of a microorganism with a feedstock containing the irrigation water.

The methods of the present invention may also be used to desalinate salt and brackish waters, e.g., by culturing a microorganism with feedstock in the presence of salt or brackish water, or where the feedstock has been grown in salt or brackish water. In particular embodiments, the microorganism is capable of growing or living in salt or brackish water, e.g., the microorganism is salt water-tolerant. In certain embodiments, the microorganism is an algae, e.g., a salt water-tolerant red, green, blue-green or red algae.

In particular embodiments, the resulting fresh water can be purified of other products, or it can be used as a carrier for fertilizers or food supplements, e.g., food supplements for livestock, poultry or fish.

In order to achieve water having a desired salinity or purity, methods of the present invention may also be practiced repeatedly or consecutively.

Biomass Processing Apparatus

The present invention further includes a processing system useful for performing methods of the present invention. This processing system and associated apparatus may be used to perform one or more steps of a method of the present invention. In particular embodiments, the processing system of the present invention is used to conduct autolysis in the presence of both an organic solvent and an aqueous solution, thus facilitating the extraction or release of lipids and other products from a biomass, and also allowing the separation of extracted lipids and other products into either the organic solvent or aqueous solution, from which they may then be purified.

In further embodiments, additional processing steps may be performed in the processing system. For example, a fermentation step may optionally be performed in the processing system. Fermentation of sugars present in an autolysate may be performed, e.g., by introducing yeast into the lower aqueous layer present in the processing system. Upon introduction of yeast, the lower layer may be stirred to facilitate yeast growth and fermentation, and air may be introduced. Subsequently, the introduction of air may be stopped, to facilitate anaerobic fermentation of fermentable sugars present in the aqueous layer of the autolysate.

In particular embodiments, a biomass is introduced into the processing system after being collected. In certain embodiments, it is introduced into the processing system after being collected and after the initiation of autolysis. This embodiment is particularly useful when the processing system is being used to process biomass in a continuous system. For example, as biomass is processed and autolysate and/or products are removed from the system, additional biomass and/or lysate may be provided to the system. By initiating autolysis before introducing the biomass into the processing system, the possibility that the method of initiating autolysis (e.g., the method used to kill the biomass microorganisms) will damage other components of the processing system (e.g., microorganisms used for fermentation) is avoided.

However, the present invention further contemplates that either or both culturing or generation of the biomass on a biodegradable substrate and/or the initiation of autolysis may be performed in the processing system. This is particularly applicable when the biodegradable substrate is a liquid substrate or is present in solution, e.g., where a biomass is not collectible.

In particular embodiments, a biomass may be present in an aqueous solution when it is introduced into a processing system, or it may be introduced into a processing system together with an aqueous solution. In certain embodiments, autolysis of the biomass is initiated and some autolysis will have occurred before the biomass is introduced into the processing system, so a mixture of biomass and lysate is introduced into the processing system. In this context, the term "lysate" indicates autolysed biomass. An organic solvent is also introduced into the processing system, and this organic solvent forms a layer above the aqueous solution. The biomass is typically present in the aqueous solution layer. As the biomass undergoes autolysis, it releases cellular components, which are soluble in either or both of the organic solvent or aqueous solution. Therefore, the resulting "autolysate" comprises: (1) the layer comprising the organic solvent and cellular components soluble in the organic solvent, e.g., lipids; and (2) the layer comprising the aqueous solution and cellular components soluble in the aqueous solution, e.g., sugars.

As a biomass undergoes autolysis and its cellular components are released into the organic solvent or aqueous solution, additional biomass and/or lysate may be added to the system. In addition, either or both of at least a portion of the layer comprising the organic solvent layer or layer comprising the aqueous solution may be withdrawn or removed from the system, e.g., in order to extract or purify cellular components therefrom. In addition, autolysate (or a layer thereof) remaining from a previous processing run may be added back to the system. For example, after extraction of desired cellular components from the organic solvent layer, the remaining organic solvent may be recycled and used in subsequent processing runs. Thus, biomass, lysate, and/or autolysate may be added to the processing system from one or more biomass, lysate, or autolysate sources.

In addition to the apparatus where autolysis, fermentation, and separation of lipids and other products occurs, the processing system may further include additional components useful for isolating or purifying one or more desired products from either the organic solvent or aqueous layer. For example, the processing system may include one or more separation or extraction units, e.g., to extract aqueous layer or products therein and/or to extract non-aqueous layer or products therein. Separation and extraction allows room for additional biomass, lysate, autolysate and/or filtrate to be added to the processing system, which, in turn, allows for a longer processing time, thus producing increased amounts of lipids and other products.

For any of the methods described herein, various starting materials and processing materials may be added to the system via any suitable inlet unit, e.g., one that introduces material into either the organic solvent layer or the aqueous layer.

In one embodiment, the present invention includes an apparatus for processing a microorganism biomass, which comprises: (1) a container for holding biomass and autolysate, wherein said autolysate comprises an organic solvent layer and an aqueous layer, wherein said organic solvent layer is above the aqueous layer; (2) a mixing apparatus for mixing the biomass and aqueous layer; (3) one or more input ports for introducing organic solvent, autolysate, or other components into the system; and (4) one or more output ports for removing either or both organic solvent layer or aqueous layer from the container. In certain embodiments, the apparatus comprises at least two output ports; one located towards the bottom the container for removing aqueous layer and one located towards the top of the container for removing organic solvent layer.

The apparatus may be part of a processing system that further includes one or more of: (1) a feed apparatus including a biomass and/or lysate source coupled to the container and an organic solvent source coupled to the container; (2) a collection unit in fluid communication with the container, the collection unit configured to collect either or both of aqueous layer or organic solvent layer of the autolysate and components therein; and (3) a controller communicatively coupled to the feed apparatus and the collection unit, wherein the controller is configurable to command the collection unit to remove aqueous layer and/or organic solvent layer from the chamber and, optionally, to separate or extract the components from either layer, and is configured to command the feed apparatus to adjust the composition of the autolysate.

FIG. 1 shows a processing system 100 for processing biomass. The processing system 100 includes a separation tower 108, a feed apparatus 110, and a controller 112 communicatively coupled to the separation tower 108 and the feed apparatus 110. The processing system 100 can be used to induce fermentation, hold biomass during autolysis and/or fermentation, separate components of the biomass, and/or otherwise process or store biomass. Autolysis can be performed to produce autolysates. Separation can be performed to facilitate removal or purification of desired substances from the autolysate, e.g., lipids and other materials.

Generally, the feed apparatus 110 can deliver biodegradable substrates, biomass (e.g., harvested microorganism biomass), lysates, autolysates, filtrates, organic solvents, additives, or combinations thereof to a container 114. Biomass in the container 114 can undergo autolysis, fermentation, separation, or other suitable process. Autolysates can undergo fermentation, separation of the organic solvent and aqueous layers, and other suitable processes. A collection unit 120 can extract or separate components of the biomass, and/or it can extract the aqueous layer (or a portion thereof). In a continuous production cycle, autolysis can take place simultaneously with a fermentation process. This allows for generally continuous processing. The collection unit 120 can continuously or intermittently draw and process the aqueous layer (and products therein). In other production cycles, the processing system 100 can sequentially process the biomass, autolysate, and/or filtrate. For example, the biomass can undergo autolysis, and products released from the biomass or contained within the autolysate or filtrate can be subsequently separated into the organic layer or aqueous layer. The separated components can be individually processed, and products therein can be purified.

Figure 2:
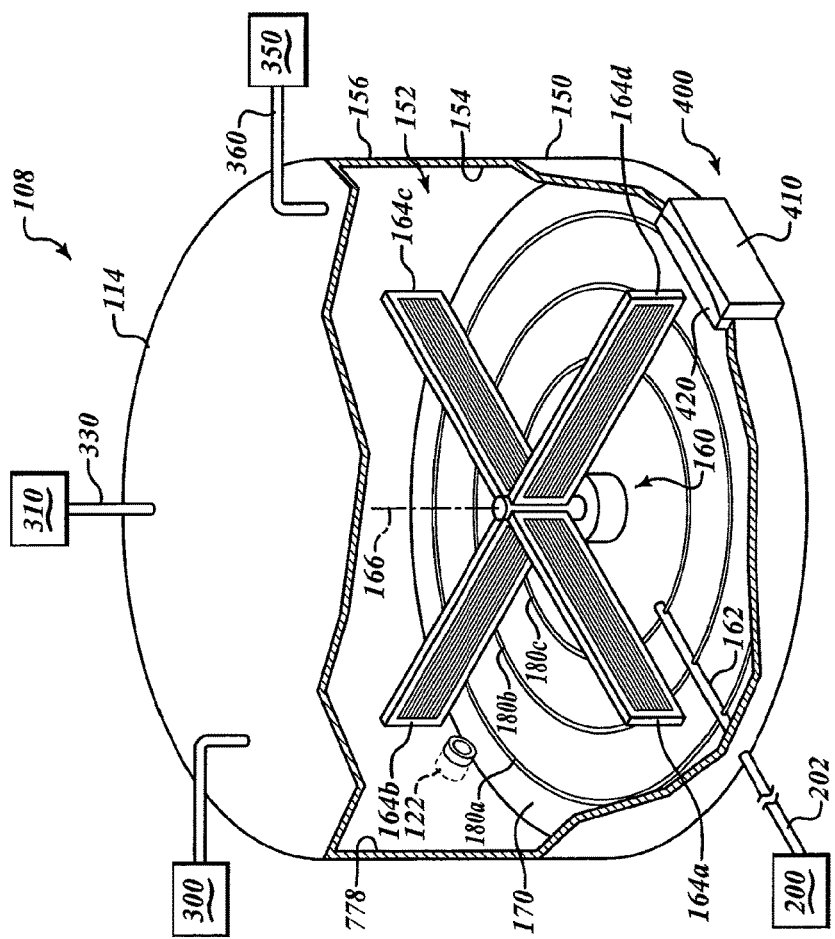
FIG. 2 is a partial cutaway view of the processing system of FIG. 1.

Referring to FIG. 2, the container 114 includes a main body 150, a mixing apparatus 160, and an aeration device 162. The main body 150 defines a closed chamber 152 and can be made, in whole or in part, of glass, metal (e.g., stainless steel), ceramics, or other types of inert materials. Coatings can be applied to an interior surface 154 of the main body 150. Such coatings can be made, in whole or in part, of inert polymers, enamels, or other suitable materials for contacting the biomass. A sidewall 156 of the main body 150 can define a wide range of different geometrical shapes (as viewed from above), including an elliptical shape, a circular shape, or a polygonal shape. The illustrated chamber 152 has a generally circular cross-sectional profile.

The container 114 can be used to control the temperature of the biomass and/or autolysate, e.g., to control the temperature during autolysis and fermentation. To heat biomass and/or autolysate, a heated fluid can be passed through channels embedded in the main body 150. To cool the biomass and/or autolysate, a chilled fluid can be passed through the channels. Additionally or alternatively, thermal elements (e.g., resistive heaters, Peltier devices, or other types of electric heaters) can convert electrical energy to thermal energy to heat or cool the biomass and/or autolysate. In some alternative embodiments, a thermal jacket can surround the main body 150 and can be used to increase or decrease the temperature of the biomass and/or autolysate.

Referring again to FIG. 1, the feed apparatus 110 includes a first source 210, a second source 220, and a reservoir 230. A line 232 extends from the first source 210 to a first inlet 240 of the container 114. A line 250 extends from the second source 220 to a second inlet 260 of the container 114. A line 270 extends from the reservoir 230 to an outlet 280 of the container 114. The first and second sources 210, 220 and the reservoir 230 can cooperate to adjust the composition of the biomass or autolysate. For example, the feed apparatus can deliver biomass, lysate, autolysate, filtrate, organic solvent, aqueous solution, and/or yeast into the container.

The sources 210, 220 can include, without limitation, one or more containers (e.g., tanks, vats, reservoirs, towers, canisters, or the like), pumps, filters, sensors, or the like. If the first source 210 is an autolysate source, a pump can pressurize the autolysate. The pressurized autolysate is delivered through the line 232 to the container 114. The first source 210 can hold materials to be processed using the processing system. For example, these materials may be biomass having initiated autolysis and its resulting lysate. The first source 210 can further hold filtrate and organic solvent that were mixed with the biomass, e.g., during preparation of the biomass or near initiation of autolysis. In addition, the first source 210 can hold additives or supplements, including biomass and/or lysate processed elsewhere that contains useful intracellular or extracellular materials, e.g., enzymes to expedite autolysis or components desired in an end product. For example, if the end product is an animal or plant nutritional supplement, and certain components, e.g., vitamins, are desired in this end product, a biomass with such vitamins may be processed elsewhere and delivered to the container 114 through the source 210. Thus, the first source 210 can hold, without limitation, biomass, lysate, autolysate, filtrates, additives, and organic solvent. In other embodiments, the first source 210 includes a first container holding a material (e.g., biomass and/or lysate) and a second container holding a different material (e.g., filtrates). The biomass and/or lysate and filtrates can be delivered through separate lumens in the line 232. In yet other embodiments, the first source 210 can be in the form of a bioreactor, separation tower, biomass processing system (e.g., biomass system for inducing autolysis), or the like. Biomass, lysate, and/or autolysate in source 210 can be delivered through the line 232 to the container 114. Multiple biomass processing units can deliver biomass, lysate, and/or autolysate to the same container 114 through the first source 210. These biomass processing units can be processing units for fungal, algal and/or bacterial processing. The second source 220 can hold, without limitation, organic solvent. In certain embodiments, the second source 220 includes a container that holds organic solvent. In yet other embodiments, the second source 220 can hold other types of materials, such as inorganic materials (e.g., inorganic non-aqueous solvents), additives for treating lipids, combinations thereof, or the like. The second source 220 can sequentially deliver materials or deliver mixtures to the container 114.

The mixing apparatus 160 of FIG. 2 can mix, agitate, stir, or otherwise mechanically process the biomass by rotating mixing elements, illustrated in the form of fins 164*a*, 164*b*, 164*c*, 164*c* (collective "164"), about an axis of rotation 166. The fins 164 can help distribute air from the aeration device 162, ensure that components (e.g., enzymes, compounds, or the like) are properly mixed together, and/or facilitate movement of the biomass towards the collection unit 120. For example, the fins 164 can help move autolysate, fermentation byproducts, or other targeted substances towards the entrance of the collection unit 120.

The aeration device 162 can rest on a bottom 170 of the container 114 and can include a plurality of lines 180*a*, 180*b*, 180*c* (collectively "180"). The lines 180 can be tubes, hoses, pipes, or conduits and can be made of an inert material to contact the biomass. The aeration device 162 can be removed from the container 114 to perform, for example, inspections or routine maintenance. Movable grills or other types of structures can cover the aeration device 162. In other embodiments, the aeration device 162 is integrally formed in the bottom 170. For example, the lines 180 can be a network of passageways in the bottom 170. The aeration device 162 can also include valves, perforated plates, baffles, or the like.

A pressurization device 200 can deliver compressed air through a line 202 to the aeration device 162. The pressurized air exits openings in the lines 180 and is distributed through the biomass. To avoid contamination, the pressurized air can be biologically filtered air. The pressurization device 200 can include different types of air filters for producing biologically filtered air.

The controller 112 of FIG. 1 can generally include, without limitation, one or more computers, central processing units, processing devices, microprocessors, digital signal processors, central processing units, processing devices, microprocessors, digital signal processors (DSP), application-specific integrated circuits (ASIC), readers, and the like. To store information, the controller 112 can include, without limitation, one or more storage elements, such as volatile memory, non-volatile memory, read-only memory (ROM), random access memory (RAM), or the like. The stored information can include, without limitation, optimization programs, biomass preparation programs, autolysis programs, fermentation programs, calibration programs, collection programs, or other executable programs. Data or other information obtained during processing can be stored by the controller 112. The controller 112 can execute optimization programs to optimize performance (e.g., reduce cycle times, increase productivity, improve processing consistency, or the like), determine processing parameters (e.g., processing temperatures, mixing sequences, or the like), monitor the biomass or autolysate, or the like. The controller 112 can be communicatively coupled to the first source 210, second source 220, reservoir 230, a valve of the output 122, or any other component, such as the collection unit 120 or mixing apparatus 160.

Referring to FIG. 1, a valve 300 can serve as a safety valve to control the processing pressure. The valve 300 can be in fluid communication with another processing apparatus, such as a bioreactor or a photoreactor. Air containing carbon dioxide produced by alcoholic fermentation can be delivered to the photoreactor. Thus, waste gases can be delivered to another system while maintaining a desired pressure.

A pressurization device 310 can supply pressurized fluid to regulate the processing pressure and can include, without limitation, one or more air compressors, pumps, or other types of devices. A filter can be used to filter fluid (e.g., air) delivered through a line 330 and into the container 114. By way of example, the pressurization device 310 can continuously or intermittently supply biologically filtered air to keep the pressure substantially greater than the organic solvent pressure to control the amount of solvent vapor in the container 114. Such embodiments are well suited to control or eliminate evaporation of solvents.

A condenser 350 is capable of condensing organic solvent vapors and returning the condensate back to the chamber 152. A line 360 can be a multi-lumen line through which solvent vapors flow away from the container 114 and liquid solvent flows in the other direction back to the container 114. Alternatively, the condensate can be returned to the container 114 via the line 250.

An access door 400 can include an outer door 410 and an inner door 420. The inner door 420 can form a seal (e.g., a watertight seal or an airtight seal) to prevent biomass from escaping out of the container 114. To remove residue or to clean the chamber 152, tools (e.g., mechanical shovels, sterilization equipment, hoses, or the like) can be passed through the opened door 400. In other embodiments, the door 400 can be a single door.

The outlet 122 is positioned opposite the door 400. Pumps or other types of suction devices can be coupled to the outlet 122. Residue within the container 114 can flow through the outlet 122 under its own weight or via a vacuum. For example, at the end of a production cycle, residue on the floor 170 can be conveniently removed via the outlet 122.

Figure 3:
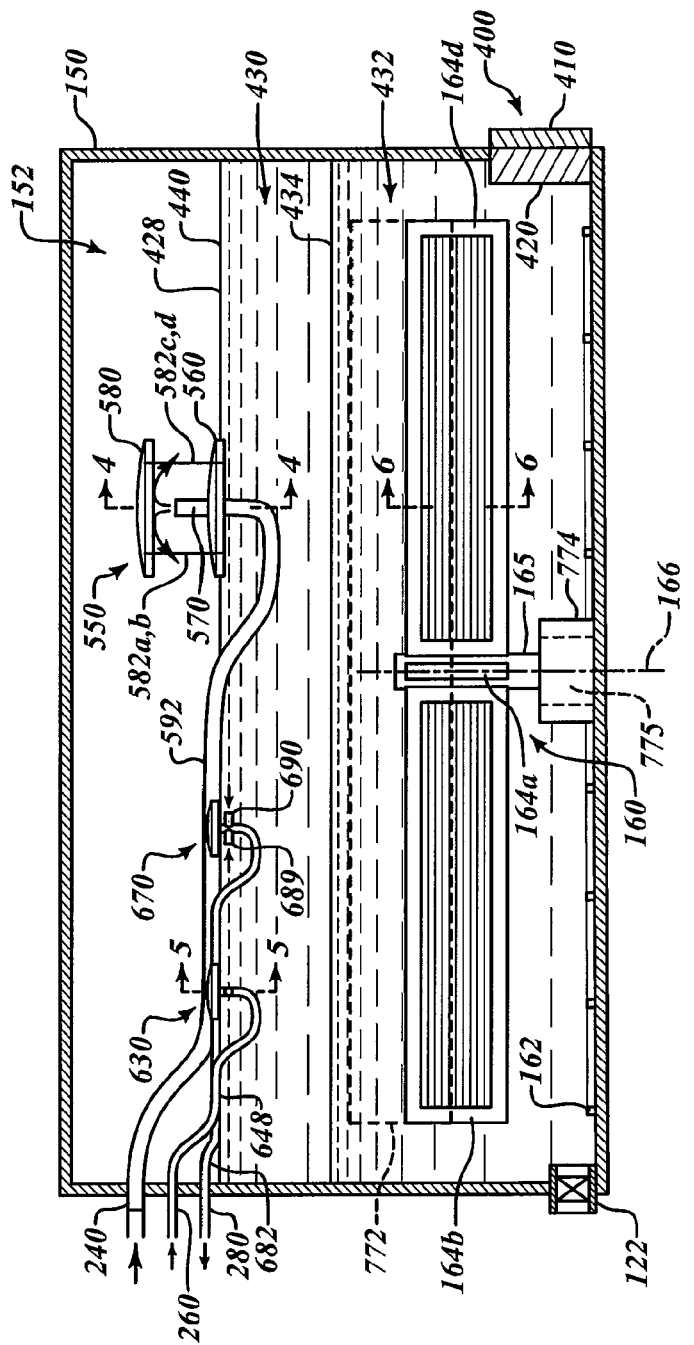
FIG. 3 is a cross-sectional elevational view of a container of the processing system of FIG. 1. The container is shown holding biomass.

FIG. 3 shows the container 114 containing a non-aqueous layer 430 (i.e., an organic solvent layer) and an aqueous layer 432. The aqueous layer 432 can be in the form of a cellular autolysate layer. To prevent disruption (e.g., unwanted mixing or agitation) of the non-aqueous layer 430, the fins 164 can be positioned below an interface 434 of the layers 430, 432.

Figure 4:
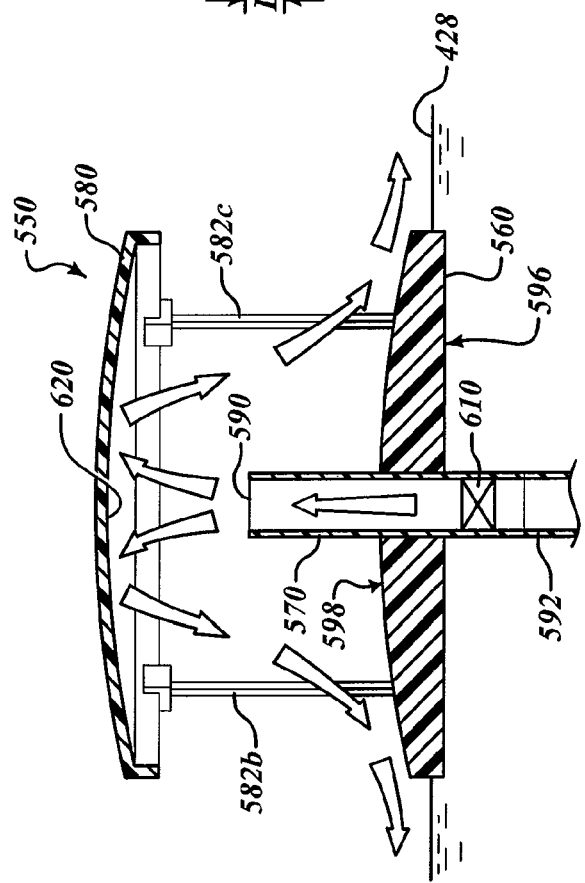
FIG. 4 is a cross-sectional view of an inlet unit taken along a line 4-4 of FIG. 3.

An inlet device 550 is floating on top of the non-aqueous layer 430 and includes a lower member 560, a delivery tube 570, and an upper member 580. The upper member 580 is spaced apart from the lower member 560 by a plurality of columns 582a, 582b, 582c, 582d (collectively "582"). The delivery tube 570 is carried by the lower member 560 and extends in a generally vertical direction during use. As shown in FIG. 4, an opening 590 of the delivery tube 570 is positioned between the members 560, 580.

Referring to FIGS. 3 and 4, the lower member 560 can be a float that includes a generally planar bottom surface 596 and a non-planar upper surface 598. The upper surface 598 can be a curved surface, such as a partially spherical surface or partially elliptical surface. The shape, dimensions, and curvature of the upper surface 598 can be selected to facilitate the flow of material towards the periphery of the lower member 560, as indicated by the arrows. The lower member 560 can have a density that is sufficiently low so as to keep the upper surface 598 from being submerged. Different types of materials (e.g., inert foams, synthetic materials, polymers, or rubbers) can be used to form the lower member 560.

The tube 570 can be a rigid tube made, in whole or in part, of metal, rigid polymers, or the like and can be permanently or temporarily coupled to a line 492, which extends from the tube 570 to the inlet 240. A valve 610 is positioned along the conduit 570 and can be a one-way valve (e.g., a duckbill duct valve or a check valve) that allows flow of the flowable material into the container 114 and substantially prevents the flow of biomass out of the container 114. The line 592 is a generally flexible hose that can float to keep the line 592 from contacting the mixing apparatus 160. Material (e.g., biomass, lysate, autolysate or filtrate) from the source 210 can flow through the line 592 to the inlet device 550.

When material is delivered out of the outlet 590, the material can fall onto the upper surface 598. The upper member 580 can help deflect the material towards the lower member 560 and limit excessive spraying or dispersion of the material. If the material strikes a lower surface 620 of the member 580, the material can be deflected back towards the surface 598. The deflected material can flow along the surface 598 due to gravity. In this manner, the material drains to the non-aqueous layer 430. The material, in some embodiments, can be delivered at a relatively high flow rate without appreciably disrupting the non-aqueous layer 432.

Figure 5:
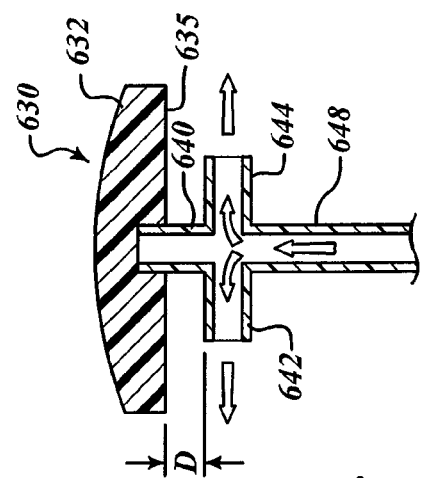
FIG. 5 is a cross-sectional view of an inlet unit taken along a line 5-5 of FIG. 3.

Referring to FIGS. 3 and 5, an inlet unit 630 can deliver substances directly into the non-aqueous layer 430 and includes a float 632 and a conduit 640 coupled to the float 632. The conduit 640 includes delivery ports 642, 644. A line 648 extends between the conduit 640 and the inlet 260. When a material (e.g., organic solvent) flows through the line 648 (indicated by arrows), the material flows out of the port 642, 644 and into the non-aqueous layer 430. A distance D between a bottom surface 635 of the float 632 and the ports 642, 644 can be selected to ensure that the ports 642, 644 are positioned within the non-aqueous layer 430. For example, the distance D can be equal to the diameters of the ports 642, 644. In some embodiments, the distance D is in a range of about 5 mm to about 20 mm. Other distances are also possible, if needed or desired. In other embodiments, ports can be located at different heights. Each port can be in fluid communication with a different lumen in the line 648. Different flowable substances can be delivered at different locations. In some embodiments, the ports can be positioned to deliver material to and/or remove material from layers 430, 432. By way of example, the line 648 can pass through both layers 430, 432. Ports of the line 648 can be positioned in each of the layers 430, 432. A first lumen in the line 648 can provide fluid communication with the layer 432 and another lumen can provide fluid communication with the layer 430.

An outlet unit 670 of FIG. 3 is generally similar to the inlet unit 630, except as detailed below. The outlet unit 670 includes a line 682 that extends from a float to the outlet 280. Inlet ports 689, 690 are positioned in the non-aqueous layer 430. Material in the non-aqueous layer 430 can be drawn into the inlets 689, 690 and flows through the line 682. The material proceeds along the line 682 and is ultimately delivered to the reservoir 230 (FIG. 1).

Figure 7:
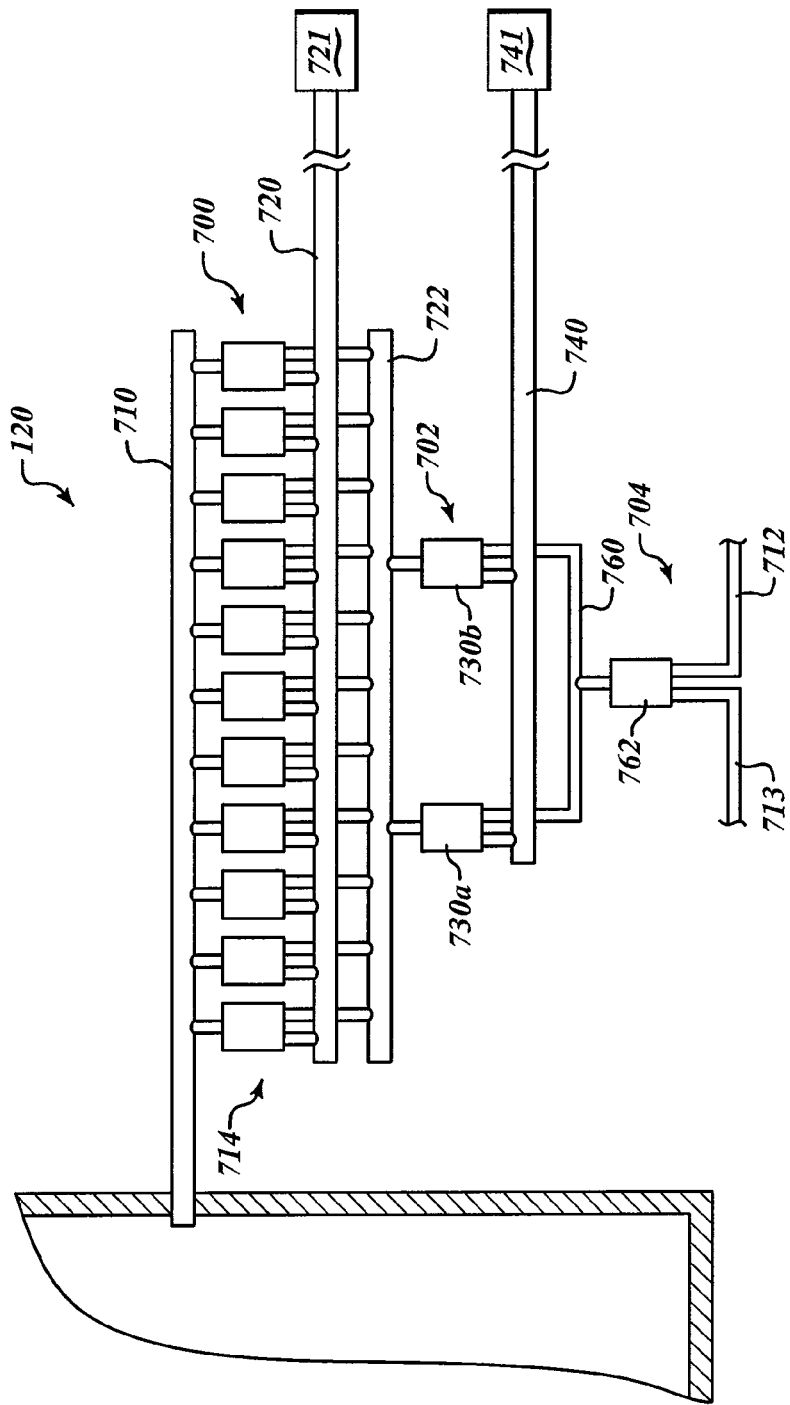
FIG. 7 is a detailed elevational view of a collection unit.

Referring to FIGS. 1 and 7, the collection unit 120 includes a first filter device 700 for filtering biomass, a second filter device 702 for filtering material from the first filter device 700, and a third filter device 704 that filters material from the second filter device 702. Material can be delivered through the filter devices 700, 702, 704 to sequentially process (e.g., extract, separate, etc.) material. If the filter devices 700, 702, 704 separate biomass components, the separation sequence can be selected based on the percent volume of the components. By way of example, the first filter device 700 can separate out the component with the greatest percentage by volume. The second filter device 702 can separate out the component with the second greatest percentage by volume (i.e., the greatest volume by percentage in the material from the first filter device 700). This process can be repeated to sequentially separate materials.

The first filter device 700 includes a feed line 710 and an output line 720. Biomass flows through the feed line 710 and through filters 714. An entrance to the feed line 710 can be positioned along the aqueous layer 432 to ensure that aqueous material is drawn into the collection unit 120. The illustrated embodiment of FIG. 7 has eleven filters 714 arranged in parallel. A greater or lesser number of filters 714 can be used and can be arranged in series. If the aqueous material comprises mostly water by volume, the filters 714 can separate out water. The water can be delivered to the output line 720, which in turn delivers the water to a water-holding container 721. The dewatered material (e.g., partially or completely dewatered fluid) can be delivered to a feed line 722.

The feed line 722 is fluidically coupled to a pair of filters 730a, 730b (collectively "730"). The filters 730 can separate the dewatered material. In some embodiments, the filters 730 separate out and deliver alcohol to a filtrate line 740 coupled to a reservoir 741. The other portion of the material is delivered to a feed line 760 in fluid communication with a filter 762. The filter 762 can separate or extract one or more targeted substances. The filtrate can be delivered through an output line 712. The remaining autolysate can be delivered via a line 713 to another processing unit or to the container 114 for further processing. In this manner, aqueous material can be successively processed. The number of filter devices and filters can be selected based on the number of substances to be extracted or separated. Additionally, any number of collection units can be used. For example, multiple collection units can be used simultaneously process biomass.

To begin a production cycle, the container 114 of FIGS. 1 and 2 can be sterilized. Material can be pumped under pressure into the chamber 152. A mixture comprising sterilized biomass, lysate, autolysate, filtrate, and/or organic solvents can be delivered through the line 232. The mixture flows through the line 592 and out of the inlet unit 550. As the container 114 is filled, the internal pressure may gradually increase. The valve 300 can regulate the pressure in the container 114 to ensure that the pressure in the container 114 is kept at or below a desired level. As the mixture fills the chamber 152, the inlet unit 550, the inlet unit 630, and the outlet unit 670 can float on the surface 440. The sources 210 and 220 can deliver materials to the container 152 during the filling process. The outlet unit 670 may or may not withdraw fluids (e.g., organic solvent layer) from the container 114 during the filling sequence. The organic solvent and the aqueous layer of the autolysate can separate to form different layers. FIG. 3 shows the non-aqueous layer (e.g., organic solvent layer or lipid layer) 430 and the separate aqueous layer 432. The non-aqueous layer 430 can include an organic solvent and lipids that can serve as a buffer between the aqueous layer 432 and the unfilled portion of the chamber 152.

After partially or completely filling the chamber 152, the aqueous layer 432 can be inoculated with fermenting organisms (e.g., microorganisms capable of converting carbohydrates into alcohols or acids; e.g., yeast). The aeration device 162 delivers air into the aqueous layer 432. The valve 300 can be used to control the working pressure, especially if the air from the aeration device 162 causes the pressure to become excessively high. The length of the aeration period can be selected based on the volume of the container, number of inoculated microorganisms, composition of the biomass, processing temperatures, airflow rate, mixing action, and the like.

The fermenting organisms can begin to multiply. The mixing apparatus 160 can rotate the fins 164 to help distribute the organisms and air in the aqueous layer 432. The rotational speed of a shaft 165 carrying the fins 164 can be increased or decreased to adjust the distribution of organisms, air, and temperature profile of the biomass/autolysate. For example, the fins 164 can be rotated at a rotational speed sufficient to generally evenly distribute the organisms and filtered air in the aqueous layer 432. The fins 164 can be moved vertically to ensure that substantially the entire height of the aqueous layer 432 is adequately mixed. For example, a drive device 774 (FIG. 3) can extend the shaft 165 to mix an upper region of the aqueous layer 432. The drive device 774, in some embodiments, can move the fins 164 away from or towards the bottom 170 while the fins 164 rotate. The fins 164 shown in FIG. 3 are in a lowered position and can be elevated to a raised position 772 (shown in dashed line). The vertical position of the fins 164 can be selected based on characteristics (e.g., temperature, viscosity, composition, or the like) of the biomass or autolysate.

Figure 6:
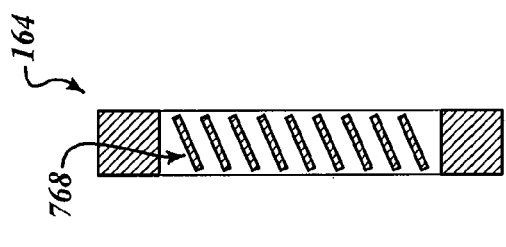
FIG. 6 is a cross-sectional view of a fin taken along a line 6-6 of FIG. 3.

The aqueous layer 432 can flow through the fins 164 to enhance mixing action. The fin 164 of FIG. 6 has slits defined between spaced apart slats 768. Alternatively, fins can have openings, perforations, or other holes through which the biomass can flow. Other types of fins, stirrers, or agitators can also be used, if needed or desired.

The drive device 774 can include a motor 775 (e.g., an energizable electric motor) with the drive shaft 165. The motor 775, drive shaft 165, and fins 164 can move together to move the fins 164 in the vertical direction. Alternatively, the motor 775 can have an extendable shaft 165. The motor 775 can thus be fixedly coupled to the container 114.

To produce alcohol, aeration can be reduced or substantially stopped. During autolysis, any number of compounds can be released out of the biocells before and during alcohol production. Certain lipids will join the upper solvent layer 430 while additional compounds can remain in the aqueous layer 432. The mixing apparatus 160 can stir the aqueous material during fermentation, if needed or desired.

At any time during production, the collection unit 120 can process the aqueous layer 432. The feed line 710 can be positioned below the interface 434 between the layers 430, 432 such that only aqueous material is drawn into the collection unit 120. The collection unit 120 can be coupled to an inlet unit that draws in the aqueous layer (or the aqueous portion thereof), as discussed in connection with FIG. 8. The collection unit 120 can separate water and alcohol, and extract any number of targeted compounds within the autolysate and filtrate. The remaining materials can be returned to the container 114, to another processing system, or to a recycling system. In some embodiments, the collection unit 120 periodically draws material for processing. In other embodiments, the collection unit 120 continuously draws material for processing.

The outlet unit 670 can draw non-aqueous material (e.g., lipids) from the non-aqueous layer 430. To maintain a suitably thick non-aqueous layer 430, non-aqueous material (e.g., organic solvent) can be delivered through the inlet unit 630 to replace the moved liquid volumes. For example, the volumetric flow rate of lipids being removed using the outlet unit 670 can be generally equal to the volumetric flow rate of the organic solvents delivered through the inlet unit 630. Of course, the flow rates can be adjusted to increase or decrease the thickness of the non-aqueous layer 430.

During a production cycle, the temperature, pH levels, composition of the biomass and/or autolysate, and other processing characteristics may be monitored. FIG. 2 shows a sensor 778 that can send signals to the controller 112, which can adjust operation of components of the processing system 100 based on the signals. The sensor 778 can include, without limitation, one or more temperature sensors, pH sensors, viscosity sensors, probes, or the like. For example, the controller 112 can adjust the temperature of the biomass based on signals from the sensor 778 in the form of a temperature sensor. Alkaline, acid, water, or the like can added or removed to adjust the pH value or other characteristics of the biomass.

Any number of partial and complete fillings can be performed. Subsequent fillings can be performed in a similar manner as discussed above, except as detailed below. The organic solvent volume can be reduced in subsequent fillings. In the first filling process, the organic solvent volume can be sufficient to form a sufficiently thick organic solvent layer 430 that covers the entire upper surface of the aqueous layer 432. The successive filling operations can have a lower organic solvent volume that is sufficient to dissolve the lipids within the filling process. By way of example, a sufficient volume of the organic solvent can be the first substance delivered into the chamber. The organic solvent can coat and fill the chamber to a desired height. Subsequent loads can have a sufficient volume of organic solvent so as to dissolve the lipids for the particular loading process. Advantageously, additional inoculation processes and aeration processes do not have to be performed. In this manner, components can be delivered into the container 114 any number of times to continuously produce desired materials.

When the container 114 is filled to a desired level, the production cycle can be completed. The length of time to complete a cycle can be about 2 to about 4 weeks, depending on the volume of the container 114. The length of a cycle can be determined based on the last upload time for partial autolysis. The controller 112 can automatically calculate an estimated cycle length based, at least in part, on the length of time of the last production cycle. After autolysis, a sterilizing material can be delivered into the container 114 to kill fermentative organisms. The fermentative organisms can also conduct autolysis. The completion of the autolysis or killing of the fermentative organisms can take about 2 to about 4 weeks. Another upload process can be performed to achieve a desired autolysis percentage and a desired fermentative organism autolysis percentage. During a phase-out period, the processing apparatus 100 can operate normally with or without using the units 630, 670.

After a production cycle, the container 114 can be evacuated of solid residues. During a phase-out period, the collection unit 120 may or may not process biomass. The door 400 can be opened to provide access to the chamber 152. Mechanical tools, washer units, or the like can be used to remove solid residue. The bottom 170 can be angled or sloped to help urge the material towards the outlet 122. In some embodiments, a vacuum can be applied to suck most of the residue through the outlet 122. When most of the residue is taken out of the container 114, the door 400 is opened and the rest of the solid residue is removed. The interior of the container 114 is then washed and sterilized.

The length of a production cycle can be sufficiently long to allow substantially 100% hydrolysis of the cells. To achieve almost 100% hydrolysis, two or more processing systems can work in parallel to allow for enough time for substantially 100% autolysis. A single production cycle can also last for years. The production cycle is the cycle between two sterilization processes. To maintain high production rates, a plurality of processing systems can operate concurrently. During phase-out or idle times of one processing system, one or more other processing systems can output desired substances. Any number of processing systems can be used to provide uninterrupted production of desired substances. The processing system 100 can be used to produce a wide range of desired substances, including, but not limited to, acids, vitamins, antibiotics, enzymes, or other desired byproducts produced via autolysis, fermentation, or similar processes.

FIG. 8 shows a processing system 800 with inlet units 810, 812 and outlet units 820, 822 positioned at different locations. The inlet unit 810 can rapidly deliver material (e.g., organic solvents or autolysates) directly to a non-aqueous layer 840 without disrupting an upper surface 843 of an aqueous layer 844. The inlet unit 812 and the outlet unit 822 can be fluidically coupled to collection unit 120. The inlet unit 812 can rapidly deliver substances from the collection unit 120 directly to the aqueous layer 844. Aqueous solution can be removed by the collection unit 120 via the outlet unit 822 even if the aqueous layer 844 is at a relatively low level. Of course, one or more collection units can be coupled directly to the container 860. Any number of inlet units and outlet units can be positioned at different locations or at different interfaces to provide processing flexibility.

The overall density of the inlet unit 812 and outlet unit 822 can be less than the density of water and greater than the density of the solvent in the layer 844. Such units 812, 822 can "float" on the aqueous layer 844. The distance between the ports of the inlet unit 812 and the mushroom shaped float of the unit 812 can be less than twice the diameters of the ports. The distance between the ports of the outlet unit 822 and the mushroom shaped float of the unit 822 can be less than twice the diameters of the ports.

Referring to FIG. 9, a container 860 includes a main body 862 and a heating/cooling jacket 864 surrounding the main body 862. The heating/cooling jacket 864 can include heating/cooling channels 868. Heat can be transferred between the biomass 802 and the heating/cooling jacket 864 via the main body 862. The heat is transferred to or away from a working fluid in the channels 868 depending on whether the heat heating/cooling jacket 864 is cooling or heating the biomass 802. The main body 862 can be made, in whole or in part, of a highly conductive material, such as stainless steel, copper, or combinations thereof. In some embodiments, the main body 862 is made of copper (including copper alloys) that is coated with stainless steel or enamel to provide an inert interface with the biomass 802.

EXAMPLES

Example 1

Generation of a Biomass

This example describes one exemplary method of generating a biomass.

In order to generate a biomass, the fungus *Aspergillus fumigatus* was utilized as the microorganism, and well-chopped rice straw, a lignocellulosic material, was provided as the biodegradable substrate. 10 g of rice straw was placed in each of 10 flasks. The rice straw was washed and dried in the flask, and the weight of the clean, dry straw was recorded (see Table 1). The percentage of weight lost by the rice straw due to washing and drying was calculated. Once the dry weight of the clean straw was recorded, 200 ml of water was added to each flask.

Glycerol (0.1 ml/flask) and urea (0.01 g/flask) were added to the rice straw as nutritional supplements. Glycerol was chosen as a supplement, because it is a byproduct of biodiesel production, and using glycerol as a supplement is one way to recycle this abundant, inexpensive, and readily available byproduct. Urea, a common component of fertilizers, was chosen as a supplement, because the price of urea is anticipated to decrease as more fertilizers comprise amino acids derived from the autolysis of biomasses.

Seven of the 10 flasks were inoculated with *Aspergillus fumigatus* spores (Flasks A-G), and the remaining 3 flasks were left as controls (Blanks 1-3). The flasks were incubated at 29° C. for one week. Mycelia were collected and dried. The dry weights of the mycelia were recorded. The straw remaining in the flasks was dried, and the final weight of the dried rice straw was recorded. The difference in weight between the final dry weight and the initial dry weight of the rice straw in the 3 control flasks was calculated and averaged. This average represents the average rice straw weight loss due to adding water and drying. This control average weight loss value was added to the weights of the dried rice straw in the 7 inoculated flasks to more precisely determine the amount of rice straw left unconsumed by the *A. fumigatus*. This number was subtracted from the initial starting dry weight of rice straw in each of the 7 flasks to determine the amount of rice straw consumed by the *A. fumigatus*. The "Efficiency of Growth" was calculated by dividing the mycelia dry weight by the weight of consumed rice straw.

Since the substrate, in most cases, is almost valueless, the most important economical factor is the amount of biomass growth per incubation area per incubation period. The "Area Growth Rate" was calculated and recorded.

Area Growth Rate=mycelia dry weight/unit area/incubation period

The area of the flasks utilized in these experiments was 0.00785 square meters. The experiment was repeated four times, and the average dry weight of the *A. fumigatus* biomass, including mycelia and spores, was 129% of the weight of the consumed rice straw (see Table 1).

The fresh weight of the *A. fumigatus* samples was also measured (see Table 2). These measurements indicate that the dry weight of *A. fumigatus* is almost 17% of the fresh weight and that the water content in the fresh mycelium is almost 83% of the total weight.

TABLE 1

Efficiency of *Aspergillus fumigatus* growth on rice straw.

| | Flask (A) | Flask (B) | Flask (C) | Flask (D) | Flask (E) | Flask (F) | Flask (G) | Blank1 | Blank2 | Blank3 | Average |
|---|---|---|---|---|---|---|---|---|---|---|---|
| Field straw (g) | 10.00 | 10.00 | 10.00 | 10.00 | 10.00 | 10.00 | 10.00 | 10.00 | 10.00 | 10.00 | |
| Washed & dried straw (g) | 8.54 | 8.54 | 8.38 | 8.58 | 8.53 | 8.55 | 8.27 | 8.5 | 8.32 | 8.62 | 8.483 |
| Losses due to washing % | 14.60% | 14.60% | 16.20% | 14.20% | 14.70% | 14.50% | 17.30% | 15.00% | 16.80% | 13.80% | 15.17% |
| mycelium dry weight (g) | 0.29 | 0.52 | 0.25 | 0.37 | 0.39 | 0.40 | 0.40 | ******* | ******* | ******* | |
| straw weight after collecting mycelium & drying (g) | 7.685 | 7.625 | 7.82 | 8.02 | 7.59 | 7.90 | 7.50 | 8.14 | 7.98 | 8.11 | |
| losses due to over drying (g) | ******* | ******* | ******* | ******* | ******* | ******* | ******* | 0.36 | 0.34 | 0.51 | 0.403 |
| Remaining clean straw + average losses due to drying | 8.09 | 8.03 | 8.22 | 8.42 | 7.99 | 8.30 | 7.90 | ******* | ******* | ******* | |
| straw losses due to fungus (g) | 0.45 | 0.51 | 0.16 | 0.16 | 0.54 | 0.25 | 0.37 | ******* | ******* | ******* | |
| Efficiency of growth | 64.21% | 101.63% | 159.57% | 236.17% | 72.67% | 162.16% | 108.27% | ******* | ******* | ******* | 129.24% |
| mycelium dry weight (g)/square meter/week | 36.94 | 66.24 | 31.85 | 47.13 | 49.68 | 50.96 | 50.57 | ******* | ******* | ******* | 47.63 |
| mycelium dry weight (g)/square meter/day | 5.28 | 9.46 | 4.55 | 6.73 | 7.10 | 7.28 | 7.22 | ******* | ******* | ******* | 6.80 |

TABLE 2

Relationship between fresh and dry weights of *Aspergillus fumigatus*.

| Fresh weight (g) | Dry weight (g) | Dry/Fresh |
|---|---|---|
| 2.84 | 0.445 | 0.15669 |
| 2.58 | 0.365 | 0.14147 |
| 2.9 | 0.56 | 0.1930 |
| 2.7 | 0.49 | 0.1814 |
| 1.5 | 0.33 | 0.2200 |
| 2.03 | 0.3 | 0.14778 |
| 1.45 | 0.205 | 0.14137 |
| Total 16 g | Total 2.695 g | Average 0.168 |

Example 2

Autolysis Induction

This example describes one exemplary method of inducing autolysis of a biomass.

In order to induce autolysis of the *A. fumigatus* biomass, the mycelia biomass generated in Example 1 were first collected for chopping and grinding to increase the exposed surface area. After being chopped, the biomass was returned to the liquid media, and 0.2 to 0.4 g of a chlorine dioxide tablet was dissolved in the media. The biomass was exposed to the chlorine dioxide for 5 to 15 minutes to induce autolysis. Following the exposure time, the flask was agitated for about 5 to 10 minutes to let the air penetrate into the solution and decompose the chlorine dioxide. Next, the flask was incubated in UV light for about 5 minutes to decompose any remaining chlorine dioxide and sterilize the flask. Hydrogen peroxide (1.5 ml of 30% $H_2O_2$/liter of media) was then added to inhibit glucose oxidase, bleach any dyes in the biomass, and kill any surviving microorganisms. After a 1 hour incubation, 7.1 g sodium bicarbonate/liter of media was added to the flask to neutralize the hydrogen peroxide. The biomass was incubated for about 36 hours at 25-45° C. to conduct autolysis.

Example 3

Characterization of Fatty Acids and Other Products in Autolysate

This example demonstrates the production of fatty acids and other useful products using two different fungal strains according to methods of the present invention.

Briefly, 30 flasks were washed and sterilized. Culture media was prepared containing 0.5 ml of glycerol, 0.05 grams of urea, and 0.1 grams of chlorine dioxide dissolved in 1000 ml of water. 200 ml of culture media was distributed to each flask. 5 grams of well-chopped rice straw was added to each flask, where it soaked in the culture media for 10 minutes. The flasks were then agitated for 5 minutes, following which the flasks were placed under UV lamps for 10 minutes. The flasks were then inoculated with spores; 15 flasks were inoculated with *Aspergillus fumigatus* spores, and 15 flasks were inoculated with *Trichoderma viride* spores. All flasks were incubated for 6 days at 29±1° C.

Following incubation, fresh mycelia were collected and weighed. The remaining filtrate was retained. The mycelia were then dried and weighed. The dried mycelia were very well chopped with some amount of water and 0.5 grams of chlorine dioxide per liter was added. The chopped mycelia were then well-grinded with an amount of hexane sufficient to dissolve the biocell lipids and serve as a buffer between the environment and remaining autolysate, and the flasks containing the resulting suspension were agitated for 5 minutes. These flasks were then placed under UV light for 10 minutes, after which 1.5 ml of $H_2O_2$ (30% concentration) was added to each liter of suspension, and the flasks were left for one hour. After the one hour, the $H_2O_2$ was neutralized by adding 7.1 grams of sodium bicarbonate per liter of suspension. The suspension was then stored at 35-40° C. for 24-36 hours, before being stored at 7-10° C. for 4 days.

The resulting autolysates were analyzed by high performance liquid chromatography (HPLC) to determine the identity and concentrations of fatty acids and other useful products. Fatty acid content was determined for the aqueous layer of the autolysates, and glucose, organic acid, element, amino acid, and phenolic compound contents were determined for the aqueous layer of the autolysates and filtrates.

High performance liquid chromatography (HPLC) was performed by Al-Azhar University, The Regional Center for Mycology and Biotechnology, Cairo, Egypt, to analyze the contents of the filtrates and autolysates. In order to perform the HPLC assays, the samples were extracted with 250 ml of boiling water for 45 minutes and then filtered through Whatman No. 4 filter paper. The resulting extracts were lyophilized. The lyophilized extracts were then dissolved in water prior to HPLC analysis. The HPLC system used comprised two pumps (GBC Scientific LC 1110) and a UV/visible chromatography detector (GBC Scientific LC 1210). The Win Chrome software was used for data acquisition and analysis. The conditions of the system varied based on the component to be analyzed. For example, the mobile phase used to detect phenolic components comprised acetonitrile and water in an 85:15 ratio, while the mobile phase used to detect organic acids comprised methanol and 0.05 M phosphate buffer (pH 3.5) in a 40:60 ratio. The results of these experiments are provided in the following tables and the accompanying figures.

The tables below provide data related to mycelia growth (Table 3) and rice straw consumption (Table 4), as well as the intracellular (i.e., autolysate) and extracellular (i.e., filtrate) contents of the mycelia after growth on rice straw for 6 days (Tables 5 and 6). The analysis also revealed the absence of the following mycotoxins in the autolysates: aflotoxins ($B_1$, $B_2$, $G_1$, and $G_2$), ochratoxins, patulin, gliotoxin, and fuminosins (data not shown). The absence of these mycotoxins was attributed to harvesting the biomass prior to the generation of secondary metabolites.

TABLE 3

Mycelial weight after growth on rice straw for 6 days. All values shown are grams/liter.

| | Aspergillus fumigatus | | | Trichoderma viride | | |
|---|---|---|---|---|---|---|
| | Fresh weight | Dry weight | Lyophilized cells | Fresh weight | Dry weight | Lyophilized cells |
| Mean | 10.07 | 1.32 | 1.2 | 21.53 | 3.47 | 2.98 |
| SD | 0.41 | 0.352 | .21 | .74 | .95 | .88 |

TABLE 4

The consumption rate of rice straw after growth of fungi for 6 days. All values shown are grams/liter.

|  | Aspergillus fumigatus | | Trichoderma viride | |
| --- | --- | --- | --- | --- |
| Control (straw) | Straw Wt after treatment | Consumption rate | Straw Wt after treatment | Consumption rate |
| Mean 19.6 | 19.16 | 2.25% | 18.87 | 3.7% |
| SD | 0.12 | | 0.178 | |

TABLE 5

Intracellular total soluble protein, carbohydrates and lipids produced after growing on rice straw for 6 days. Data are expressed in mg/gm lyophilized cells. All values shown are grams/liter.

|  | Aspergillus fumigatus | Trichoderma viride |
| --- | --- | --- |
| Total Soluble Protein | 2.3 ± 0.3 | 0.85 ± 0.29 |
| Total Soluble Carbohydrates | 3.1 ± 0.38 | 0.62 ± 0.019 |
| Total Lipids | 7.425 ± 0.69 | 3.1 ± 0.468 |

TABLE 6

Enzymes produced after growing on rice straw for 6 days.

|  | Aspergillus fumigatus | | Trichoderma viride | |
| --- | --- | --- | --- | --- |
|  | Intracellular | Extracellular | Intracellular | Extracellular |
| Amylase | − | ++ | − | + |
| Protease | + | + | + | + |
| Lipase | − | + | − | + |
| Cellulase | − | + | − | ++ |

Table 7 summarizes the consumption of rice straw and the amount of lipids and glucose present in the *A. fumigatus* and *T. viride* (combined totals for all 15 flasks for each species).

TABLE 7

Feed stock consumption and utilization by *A. fumigatus* and *T. viride*.

|  | Aspergillus fumigatus | Trichoderma viride |
| --- | --- | --- |
| Rice straw control (mg) | 19600 | 19600 |
| Rice straw after growth (mg) | 19160 | 18870 |
| consumed rice straw (mg) | 440 | 730 |
| Mycelial fresh weight after 6 days (mg) | 10070 | 21530 |
| Mycelial dry weight after 6 days (mg) | 1320 | 3470 |
| Mycelial dry weight/consumed rice straw | 300.00% | 475.34% |
| Percentage of water in fresh mycelia | 86.89% | 83.88% |
| Intracellular total lipid (mg) | 67.72 | 119.37 |
| Extracellular total lipid (mg) | 290.33 | 500 |
| Total Lipids produced (mg) | 358.05 | 619.37 |
| [Intracellular total lipid (mg) + Extracellular total lipid (mg)]/consumed rice straw (mg) | 81.38% | 84.85% |
| Intracellular glucose (mg) | 126.72 | 183.91 |
| Extracellular glucose (mg) | 166.1 | 49.83 |
| Total Glucose produced (mg) | 292.82 | 233.74 |
| [Intracellular total glucose (mg) + Extracellular total glucose (mg)]/consumed rice straw (mg) | 66.55% | 32.02% |
| Weight of produced FRESH water/consumed rice straw | 1989% | 2474% |
| Efficiency of growth | 3 | 4.75 |

The amount of various fatty acids measured in the filtrate is shown in Tables 8 and 9, where Table 8 shows data obtained from *A. fumigatus*, and Table 9 shows data obtained from *T. viride*.

TABLE 8

Chromatography peak report for fatty acids present in the *A. fumigatus* filtrate. Time values shown are minutes.

| Peak No. | R. Time | I.Time-F.Time | Area | Height | A/H (sec) | MK | % Total | Name |
| --- | --- | --- | --- | --- | --- | --- | --- | --- |
| 1 | 9.923 | 9.750-10.233 | 5559398 | 428137 | 12.985 |  | 2.39 | Lauric C12 |
| 2 | 13.059 | 12.883-13.358 | 4837954 | 377289 | 12.823 |  | 2.08 | Myristic C14 |
| 3 | 16.242 | 16.100-16.425 | 1470944 | 130060 | 11.310 |  | 0.63 | C16:1 Palmitoleic |
| 4 | 16.673 | 16.425-17.108 | 47302703 | 3211057 | 14.731 | V | 20.31 | Palmitic C16 |
| 5 | 17.943 | 17.550-18.400 | 58925404 | 3163965 | 18.624 |  | 25.30 | C17 Heptadecanoic |
| 6 | 19.792 | 19.450-20.092 | 44231224 | 2331329 | 18.973 |  | 18.99 | Oleic C18:1 |
| 7 | 20.331 | 20.092-20.642 | 38820806 | 2830249 | 13.716 | V | 16.67 | Stearic C18 |
| 8 | 21.067 | 20.842-21.208 | 6149272 | 386932 | 15.892 |  | 2.64 | Linoleic C18:2 |
| 9 | 21.431 | 21.208-21.983 | 25615323 | 1352653 | 18.937 | V | 11.00 | Linolenic C18:3 |
| Total |  |  | 232913028 |  |  |  | 100 |  |

TABLE 9

Chromatography peak report for fatty acids present in the *T. viride* filtrate.
Time values shown are minutes.

| Peak No. | R. Time | I.Time-F. Time | Area | Height | A/H (sec) | MK | % Total | Name |
|---|---|---|---|---|---|---|---|---|
| 1 | 9.660 | 9.483-10.250 | 1113409 | 62605 | 17.785 | | 0.21 | Lauric C12 |
| 2 | 12.788 | 12.575-13.117 | 1478526 | 102957 | 14.361 | | 0.28 | Myristic C14 |
| 3 | 14.502 | 14.300-14.842 | 1039099 | 72396 | 14.353 | | .020 | C15 Pentadecanoic |
| 4 | 15.967 | 15.733-16.058 | 69973 | 54212 | 12.856 | | 0.13 | C16:1 Palmitoleic |
| 5 | 16.393 | 16.058-16.892 | 72014349 | 4960616 | 14.517 | V | 13.69 | Palmitic C16 |
| 6 | 17.813 | 17.275-18.783 | 38814898 | 1380500 | 28.117 | | 7.38 | C17 Heptadecanoic |
| 7 | 19.590 | 19.067-19.908 | 243232962 | 11977062 | 20.308 | | 46.25 | Oleic C18:1 |
| 8 | 20.067 | 19.908-20.350 | 29938478 | 2152378 | 13.909 | V | 5.69 | Stearic C18 |
| 9 | 20.681 | 20.350-20.875 | 54025769 | 2884020 | 18.733 | V | 10.27 | Linoleic C18:2 |
| 10 | 21.045 | 20.875-23.017 | 80048729 | 2481480 | 32.258 | V | 15.22 | Linolenic C18:3 |
| 11 | 23.889 | 23.650-24.467 | 2056219 | 89203 | 23.051 | | 0.39 | Arachidic C20 |
| 12 | 24.782 | 24.533-25.125 | 1480283 | 81179 | 18.235 | | 0.28 | Behenic C22 |
| Total | | | 525939694 | | | | 100 | |

The amount of organic acids measured in the filtrates and aqueous layers of autolysates from *A. fumigatus* and *T. viride* is shown in Tables 10-13, where Tables 10 and 11 show data obtained from *A. fumigatus* filtrate and autolysate, respectively, and Tables 12 and 13 show data obtained from *T. viride* filtrate and autolysate, respectively.

TABLE 10

Chromatography peak report for organic acids present in the *A. fumigatus* filtrate.

| Peak Name | R. Time (min) | Conc. (mg/ml) | Height | Area |
|---|---|---|---|---|
| Oxalic Acid | 3.0 | 100.00 | 160231.0 | 6492009.0 |
| Citric Acid | 4.4 | 190.00 | 444651.0 | 11404204.0 |

TABLE 11

Chromatography peak report for organic acids present in the *A. fumigatus* autolysate.

| Peak Name | R. Time (min) | Conc. (mg/ml) | Height | Area |
|---|---|---|---|---|
| N, Methylanilin | 6.1 | 47.64 | 66604.0 | 3628066.0 |
| Oxalic Acid | 13.3 | 0.17 | 6442.0 | 407239.0 |

TABLE 12

Chromatography peak report for organic acids present in the *T. viride* filtrate.

| Peak Name | R. Time (min) | Conc. (mg/ml) | Height | Area |
|---|---|---|---|---|
| Oxalic Acid | 2.9 | 13.70 | 1816.0 | 468209.0 |
| Citric Acid | 4.8 | 17.78 | 7571.0 | 1067248.0 |

TABLE 13

Chromatography peak report for organic acids present in the *T. viride* autolysate.

| Peak Name | R. Time (min) | Conc. (mg/ml) | Height | Area |
|---|---|---|---|---|
| Pyridine | 3.0 | 0.03 | 3157.0 | 153003.0 |
| Benzoic Acid | 10.9 | 327.41 | 251653.0 | 65121580.0 |

The amount of various elements measured in the aqueous layers of autolysates from *A. fumigatus* and *T. viride* is shown in Tables 14 and 15, where Table 14 lists data obtained from *A. fumigatus*, and Table 15 lists data obtained from *T. viride*.

TABLE 14

Chromatography peak report for elements present in the *A. fumigatus* autolysate. Data from 3 samples. The mean represents mean value of normalized element percentage of total elements measured.

| | Item | Min | Max | Mean | Stddev |
|---|---|---|---|---|---|
| Elem % | C | 17.040 | 21.580 | 18.787 | 2.444 |
| Elem % | O | 68.560 | 74.010 | 72.060 | 3.038 |
| Elem % | Na | 4.210 | 5.130 | 4.673 | 0.460 |
| Elem % | Al | 1.480 | 2.210 | 1.797 | 0.374 |
| Elem % | Cl | 0.290 | 0.340 | 0.317 | 0.025 |
| Elem % | K | 0.630 | 0.860 | 0.757 | 0.117 |
| Elem % | Ca | 1.030 | 2.080 | 1.520 | 0.528 |
| Elem % | Zn | 0.020 | 0.170 | 0.090 | 0.139 |

TABLE 15

Chromatography peak report for elements present in the *T. viride* autolysate. Data from 3 samples. The mean represents mean value of normalized element percentage of total elements measured.

| | Item | Min | Max | Mean | Stddev |
|---|---|---|---|---|---|
| Elem % | C | 4.390 | 30.310 | 22.740 | 12.276 |
| Elem % | O | 62.480 | 80.130 | 67.318 | 8.551 |
| Elem % | Na | 4.690 | 5.830 | 5.255 | 0.465 |
| Elem % | Cl | 0.700 | 1.200 | 0.830 | 0.247 |

TABLE 15-continued

Chromatography peak report for elements present in the *T. viride* autolysate. Data from 3 samples. The mean represents mean value of normalized element percentage of total elements measured.

| Item | | Min | Max | Mean | Stddev |
|---|---|---|---|---|---|
| Elem % | K | 0.660 | 3.290 | 1.332 | 1.305 |
| Elem % | Ca | 0.750 | 2.160 | 1.193 | 0.651 |
| Elem % | Zn | 0.390 | 3.000 | 1.332 | 1.145 |

The amount of various amino acids measured in the aqueous layers of autolysates from *A. fumigatus* and *T. viride* is shown in Tables 16 and 17, where Table 16 shows data obtained from *A. fumigatus*, and Table shows data obtained from *T. viride*.

TABLE 16

Chromatography peak report for amino acids present in the *A. fumigatus* autolysate.

| Peak No. | Name | Time (min) | Concentration (µg/ml) | Concentration % |
|---|---|---|---|---|
| 1 | Phosphoserine | 4.08 | 31.34 | 4.32 |
| 2 | Taurine | 6.18 | 8.08 | 1.11 |
| 3 | Phosphoethanolamine | 7.98 | 1.88 | 0.26 |
| 4 | Aspartic Acid | 15.39 | 76.62 | 10.57 |
| 5 | Threonine | 21.26 | 21.97 | 3.03 |
| 6 | Serine | 23.19 | 10.09 | 1.39 |
| 7 | Glutamic Acid | 26.68 | 75.90 | 10.47 |
| 9 | Glycine | 36.04 | 18.81 | 2.60 |
| 10 | Alanine | 36.72 | 74.45 | 10.27 |
| 11 | Citrulline | 38.43 | 95.89 | 13.23 |
| 12 | Valine | 40.40 | 42.26 | 5.83 |
| 13 | Isoleucine | 54.69 | 39.13 | 5.40 |
| 14 | Leucine | 57.98 | 44.20 | 6.10 |
| 15 | Tyrosine | 62.06 | 10.54 | 1.45 |
| 16 | Phenylalanine | 65.66 | 16.61 | 2.29 |
| 18 | Beta-Aminoisobutyrc | 86.07 | 18.40 | 2.54 |
| 19 | Gama Amino-n-butyric | 87.84 | 19.80 | 2.73 |
| 20 | 3-Methyl-histidine | 91.65 | 17.69 | 2.44 |
| 21 | Carnosine | 102.09 | 63.63 | 8.78 |
| 22 | Ornithine | 104.57 | 8.94 | 1.23 |
| 23 | Lysine | 106.73 | 16.80 | 2.32 |
| 24 | Ammonium Sulfate | 107.97 | 4.19 | 0.58 |
| 25 | Arginine | 116.07 | 7.59 | 1.05 |
| Totals: | | | 724.81 | 100.00 |

TABLE 17

Chromatography peak report for amino acids present in the *T. viride* autolysate.

| Peak No. | Name | Time (min) | Concentration (µg/ml) | Concentration % |
|---|---|---|---|---|
| 1 | Phosphoserine | 4.10 | 13.39 | 2.64 |
| 2 | Taurine | 6.32 | 6.66 | 1.31 |
| 3 | Aspartic Acid | 15.41 | 37.91 | 7.47 |
| 4 | Threonine | 21.42 | 29.98 | 5.91 |
| 5 | Serine | 23.28 | 25.07 | 4.94 |
| 6 | Glutamic Acid | 26.75 | 39.26 | 7.74 |
| 8 | Proline | 34.38 | 14.26 | 2.81 |
| 9 | Glycine | 36.07 | 11.29 | 2.23 |
| 10 | Alanine | 36.74 | 48.29 | 9.52 |
| 11 | Valine | 40.45 | 26.68 | 5.26 |
| 12 | Methionine | 49.63 | 4.88 | 0.96 |
| 13 | Isoleucine | 54.79 | 33.45 | 6.59 |
| 14 | Leucine | 58.06 | 37.45 | 7.38 |
| 15 | Tyrosine | 62.14 | 10.86 | 2.14 |
| 16 | Phenylalanine | 65.72 | 15.48 | 3.05 |
| 19 | Beta-Aminoisobutyrc | 86.07 | 17.09 | 3.37 |
| 20 | Gama Amino-n-butyric | 88.04 | 5.40 | 1.07 |
| 21 | Carnosine | 102.32 | 79.67 | 15.71 |
| 22 | Ornithine | 104.55 | 13.20 | 2.60 |
| 23 | Lysine | 106.71 | 19.13 | 3.77 |
| 24 | Ammonium Sulfate | 107.97 | 4.09 | 0.81 |
| 25 | Arginine | 116.03 | 18.79 | 2.72 |
| Totals: | | | 507.27 | 100.00 |

The amount of various phenolic compounds measured in: (1) the filtrates and (2) the aqueous layers of autolysates from *A. fumigatus* and *T. viride* is shown in Tables 18-21, where Tables 18 and 19 show data obtained from *A. fumigatus*, and Tables 20 and 21 show data obtained from *T. viride*. Tables 18 and 20 show data obtained from the filtrates, and Tables 19 and 21 show data obtained from the autolysates.

TABLE 18

Chromatography peak report for phenolic compounds present in the *A. fumigatus* filtrate.

| Peak Name | R. Time (min) | Conc. (µg/ml) | Height | Area |
|---|---|---|---|---|
| Ferulic Acid | 5.17 | 0.21 | 3328.0 | 50284.0 |

TABLE 19

Chromatography peak report for phenolic compounds present in the *A. fumigatus* autolysate.

| Peak Name | R. Time (min) | Conc. (µg/ml) | Height | Area |
|---|---|---|---|---|
| Gallic Acid | 5.03 | 4682.93 | 242195.0 | 4068479.0 |
| Ferulic Acid | 5.35 | 19.56 | 207731.0 | 4576377.0 |
| Coumaric Acid | 5.62 | 98.73 | 198012.0 | 6329395.0 |

TABLE 20

Chromatography peak report for phenolic compounds present in the *T. viride* filtrate.

| Peak Name | R. Time (min) | Conc. (µg/ml) | Height | Area |
|---|---|---|---|---|
| Gallic Acid | 4.68 | 527.98 | 11931.0 | 458701.0 |
| Coumaric Acid | 5.63 | 1.03 | 3911.0 | 65755.0 |

TABLE 21

Chromatography peak report for phenolic compounds present in the *T. viride* autolysate.

| Peak Name | R. Time (min) | Conc. (µg/ml) | Height | Area |
|---|---|---|---|---|
| Coumaric Acid | 5.47 | 974.96 | 1084167.0 | 62502168.0 |
| Caffeic Acid | 9.17 | 120.19 | 19310.0 | 534040.0 |

The amount of various fatty acids measured in the aqueous layers of autolysates from *A. fumigatus* is shown in Table 22, and the amount of various fatty acids measured in the organic solvent layers of the *A. fumigatus* autolysates is shown in Table 23. Similarly, the amount of various fatty acids measured in the aqueous and organic solvent layers of the *T. viride* autolysates is shown in Table 24 and Table 25, respectively.

TABLE 22

Chromatography peak report for fatty acids present in the aqueous layer of the *A. fumigatus* autolysate. Time values are shown as minutes unless indicated otherwise.

| Peak No. | R. Time | I.Time-F. Time | Area | Height | A/H (sec) | MK | % Total | Name |
|---|---|---|---|---|---|---|---|---|
| 1 | 16.033 | 15.800-16.150 | 177044 | 13124 | 13.490 | | 0.37 | C16:1 Palmitoleic |
| 2 | 16.406 | 16.150-16.800 | 2903574 | 200360 | 14.492 | V | 6.01 | Palmitic C16 |
| 3 | 17.663 | 17.125-18.458 | 4105011 | 180353 | 22.761 | | 8.50 | C17 Heptadecanoic |
| 4 | 19.000 | 18.858-19.133 | 17329 | 1817 | 9.534 | | 0.04 | Oleic C18:1 |
| 5 | 19.567 | 19.133-19.850 | 7459653 | 416570 | 17.907 | | 15.44 | Stearic C18 |
| 6 | 20.047 | 19.850-20.292 | 2060280 | 127901 | 16.108 | V | 4.27 | Linoleic C18:2 |
| 7 | 20.793 | 20.292-21.183 | 14169781 | 628545 | 22.544 | V | 29.34 | Linolenic C18:3 |
| 8 | 21.208 | 21.183-21.867 | 2790240 | 149814 | 18.625 | V | 5.78 | Linolenic C18:3 |
| 9 | 23.076 | 22.250-23.475 | 2356977 | 54218 | 43.472 | | 4.88 | |
| 10 | 23.984 | 23.475-24.175 | 2263936 | 72043 | 31.424 | | 4.69 | Arachidic C20 |
| 11 | 25.031 | 24.175-25.975 | 9994771 | 16852 | 59.308 | V | 20.69 | Behenic C22 |
| Total | | | 48298595 | | | | 100 | |

TABLE 23

Chromatography peak report for fatty acids present in the organic solvent layer of the *A. fumigatus* autolysate. Time values are shown as minutes unless indicated otherwise.

| Peak No. | R. Time | I.Time-F. Time | Area | Height | A/H (sec) | MK | % Total | Name |
|---|---|---|---|---|---|---|---|---|
| 1 | 3.880 | 3.608-4.558 | 26334142 | 1108121 | 23.765 | | 3.44 | Caprylic C8 |
| 2 | 6.777 | 6.467-7.508 | 19094988 | 752099 | 25.389 | | 2.50 | Capric C10 |
| 3 | 9.969 | 9.667-10.600 | 17003233 | 774297 | 21.960 | | 2.22 | Lauric C12 |
| 4 | 13.140 | 12.733-13.900 | 60270564 | 2576875 | 23.389 | | 7.88 | Tridecanoic C13 |
| 5 | 14.971 | 14.658-15.700 | 15818539 | 605443 | 26.127 | | 22.07 | C15 Pentadecanoic |
| 6 | 16.823 | 16.142-17.650 | 227091320 | 9783336 | 23.212 | | 29.70 | Palmitic C16 |
| 7 | 18.075 | 17.650-18.283 | 5684823 | 240326 | 23.655 | | 0.74 | C17 Heptadecanoic |
| 8 | 18.665 | 18.283-19.358 | 31953956 | 991964 | 32.213 | V | 4.18 | |
| 9 | 20.153 | 19.517-20.33 | 163020581 | 6300738 | 25.873 | | 21.32 | Oleic C18:1 |
| 10 | 20.466 | 20.33-21.392 | 149760200 | 6056894 | 24.726 | V | 19.59 | Stearic C18 |
| 11 | 22.100 | 21.392-23.158 | 48614992 | 899670 | 54.036 | V | 6.36 | Linoleic C18:2 |
| Total | | | 764647337 | | | | 100 | |

TABLE 24

Chromatography peak report for fatty acids present in the aqueous layer of the *T. viride* autolysate. Time values are shown as minutes unless indicated otherwise.

| Peak No. | R. Time | I.Time-F. Time | Area | Height | A/H (sec) | MK | % Total | Name |
|---|---|---|---|---|---|---|---|---|
| 1 | 16.516 | 16.133-17.333 | 3011912 | 179385 | 16.790 | | 53.12 | Palmitic C16 |
| 2 | 19.056 | 18.700-19.267 | 230547 | 11261 | 20.473 | | 4.07 | |

TABLE 24-continued

Chromatography peak report for fatty acids present in the aqueous layer of the *T. viride* autolysate. Time values are shown as minutes unless indicated otherwise.

| Peak No. | R. Time | I.Time-F. Time | Area | Height | A/H (sec) | MK | % Total | Name |
|---|---|---|---|---|---|---|---|---|
| 3 | 19.674 | 19.267-19.842 | 774533 | 34701 | 22.320 | V | 13.66 | Oleic C18:1 |
| 4 | 20.085 | 19.842-20.658 | 1484489 | 79665 | 18.634 | V | 26.18 | Stearic C18 |
| 5 | 21.357 | 21.108-21.800 | 124969 | 5989 | 20.865 | | 2.20 | Linoleic C18:2 |
| 6 | 24.054 | 23.883-24.383 | 43182 | 2218 | 19.466 | | 0.76 | Arachidic C20 |
| Total | | | 5669632 | | | | 100 | |

TABLE 25

Chromatography peak report for fatty acids present in the organic solvent layer of the *T. viride* autolysate. Time values are shown as minutes unless indicated otherwise.

| Peak No. | R. Time | I.Time-F. Time | Area | Height | A/H (sec) | MK | % Total | Name |
|---|---|---|---|---|---|---|---|---|
| 1 | 10.933 | 10.717-11.383 | 512216 | 31280 | 16.375 | | 0.03 | Lauric C12 |
| 2 | 12.900 | 12.642-13.450 | 2261362 | 122225 | 18.502 | | 0.13 | Tridecanoic C13 |
| 3 | 14.698 | 14.475-15.250 | 871706 | 44402 | 19.632 | | 0.05 | Myristic C14 |
| 4 | 16.840 | 15.758-17.333 | 397235027 | 15430996 | 25.743 | | 22.12 | Palmitic C16 |
| 5 | 17.721 | 17.442-18.050 | 3224942 | 141672 | 22.763 | | 0.18 | C17 Heptadecanoic |
| 6 | 18.772 | 18.050-19.142 | 8304974 | 197235 | 42.107 | V | 0.46 | |
| 7 | 20.354 | 19.142-22.250 | 1362890718 | 31119732 | 43.795 | SV | 75.91 | Oleic C18:1 |
| 8 | 21.038 | 21.017-21.225 | 2481598 | 159791 | 15.530 | T | 0.14 | Stearic C18 |
| 9 | 21.572 | 21.292-22.008 | 13189989 | 766072 | 17.218 | T | 0.73 | Linoleic C18:2 |
| 10 | 22.761 | 22.425-23.050 | 756131 | 41327 | 18.296 | | 0.04 | Linolenic C18:3 |
| 11 | 23.569 | 23.367-23.767 | 316292 | 23430 | 13.499 | | 0.02 | |
| 12 | 24.176 | 23.767-24.633 | 3423482 | 213743 | 16.017 | V | 0.19 | Arachidic C20 |
| Total | | | 1795468436 | | | | 100 | |

It was also noted that Vitamins B, C and E were not present in the *A. fumigatus* and *T. viride* autolysate samples. Similar to the absence of mycotoxins noted above, the absence of these vitamins was attributed to harvesting the biomass prior to the generation of secondary metabolites.

Example 4

Simultaneous Saccharification and Fermentation

According to methods of the present invention, autolysis conditions were further optimized to prolong autolysis of the biomass and to demonstrate that ethanol production can occur in the anaerobic environment beneath the organic solvent layer.

In Example 2, the chopped and ground biomass was incubated for about 36 hours at 25-45° C. to conduct autolysis. Autolysis was stopped at about 36 hours, when glucose in the autolysate started to decline. This decline was attributed to thermal decomposition, destruction, or degradation of glucose at the high temperature used to conduct autolysis (25-45° C.).

Upon analysis of the filtrate and autolysate in the previous Example (see Tables 3-6), it appeared that extending autolysis beyond 36 hours may increase the production of autolysate and increase the amount of some or all products that could be obtained from the biomass. In addition, it was determined that the filtrate does contain valuable bio-products in addition to simple fermentable sugars, lipids and enzymes. Further, the surplus extracellular cellulase and amylase (Table 6) present in the filtrate were available, but were removed from the substrate and, therefore, not utilized to further hydrolyze the substrate to produce additional glucose in the filtrate.

Accordingly, methods that prolonged the duration of autolysis, while at the same time making use of all the glucose released from the microorganism during autolysis were developed. Two such methods included: (1) the Simultaneous Saccharification and Fermentation (SSF) process; and (2) glucose extraction (e.g. by membrane) from the media upon release from the cell. Following extraction in the glucose extraction method, glucose could be stored at a suitable temperature, fermented directly, or stored then fermented.

In this example, the SSF process is outlined, although the glucose extraction process is also applicable. In certain situations, the glucose extraction method may be more desirable, because xylose may be extracted separately. Since it is difficult to ferment glucose and xylose together, by extracting both sugars separately, and therefore fermenting both sugars separately, the ethanol yield would be greater.

Saccharification is part of the autolysis process because autolysis converts polysaccharides to simple fermentable sugars. Ethanol fermentation converts simple fermentable sugars, present in the lower aqueous layer, into ethanol, carbon dioxide and water. Ethanol fermentation is an anaerobic process, and the upper lipid layer of the autolysate creates an anaerobic environment for the lower aqueous layer.

Since it is unlikely the biomass will be dried when this process is replicated on a larger scale, filtrate was added to the dried mycelia instead of water, as was added in Example 3. Furthermore, adding the filtrate instead of water to the dry mycelia may provide the following benefits: (1) adding the substrate's hydrolysate to the microorganism's autolysate will expand production volume (e.g., coumaric acid is present in both the filtrate and autolysate from *T. viride*; see Tables 20 and 21) and production scope (e.g., caffeic acid is present in the *T. viride* filtrate but not in the autolysate, while gallic acid is present in the *T. viride* autolysate but not in the filtrate; see Tables 20 and 21); (2) proteases and amylases present in the filtrate (Table 6) may expedite autolysis and therefore reduce production time; (3) cellulases and amylases present in the filtrate (Table 6) may be utilized to produce additional glucose from the substrate if some of the substrate is added to the fermentation broth into the fermentor; and (4) a second batch of microorganisms, incubated on the remaining substrate of the first batch, will not find readily available nutrients (i.e., glucose, amino acids, fatty acids, etc.) that would be present in the filtrate of the first batch and will be forced to hydrolyze the substrate further to feed itself, thereby providing a second filtrate and additional bio-products, including energy. By autolysis, most of the nutrients present in the media will also be converted indirectly to bio-energy and bio-products.

It should be noted that if the bio-products are intended for nutritional additives or supplements for animals, one may not wish to add additional substrate to the fermentor as indicated in item 3 above, because the cellulases and amylases found in the filtrate will help to hydrolyze the animal's cellulosic food to glucose, thereby reducing livestock enteric $CH_4$ emissions and increasing the animal's output (e.g., milk, meat and/or power).

For this experiment, 30 flasks were washed and sterilized. Culture media was prepared containing 0.5 ml of glycerol, 0.05 grams of urea, and 0.1 grams of chlorine dioxide dissolved in 1000 ml of water. 200 ml of culture media was distributed to each flask. 5 grams of well-chopped rice straw was added to each flask, where it soaked in the culture media for 10 minutes. The flasks were then agitated for 5 minutes, following which the flasks were placed under UV lamps for 10 minutes. The flasks were then inoculated with spores; 15 flasks were inoculated with *Aspergillus fumigatus* spores, and 15 flasks were inoculated with *Trichoderma viride* spores. All flasks were incubated for 6 days at 29±1° C.

Following incubation, the fresh mycelia were very well chopped with a minor quantity of the filtrate and 0.5 grams of chlorine dioxide per liter of the total filtrate volume (200 ml×15). The chopped mycelia were then well-ground with an amount of hexane sufficient to dissolve the biocell lipids and to serve as a buffer between the environment and remaining autolysate. The remaining filtrate was added, with the rice straw, to the prepared slurry in a sterilized colorless transparent plastic container (box). The container holding the resulting suspension with the rice straw was agitated for 15 minutes. The container was placed under UV light for 15 minutes, after which 1.5 ml of $H_2O_2$ (30% concentration) was added to each liter of suspension, and the container was left for one hour. After the one hour, the $H_2O_2$ was neutralized by adding 7.1 grams of sodium bicarbonate per liter of suspension.

The plastic box was converted into a fermentor to satisfy the required purpose. It was made as air tight as possible to prevent the volatile hexane from evaporating. The fermentor was connected to an aquarium pump and an air filter to supply the lower aqueous layer with sterilized air. Any type of fermentor may be used for the fermentation step.

Immediately after neutralization, the lower aqueous layer was inoculated with the yeast *Saccharomyces cerevisiae*. The fermentor was placed in an incubator at 28±1° C. For 30 hours the lower aqueous layer was supplied with filtered air for aeration and to allow the yeast to multiply. After 30 hours, the air pump was stopped to initiate the anaerobic phase, and the *S. cerevisiae* was expected to produce ethanol.

After 10 days a sample was taken from the lower aqueous layer to be analyzed for ethanol. The presence and concentration of ethanol was detected using gas chromatography (GC). The retention time, i.e., the time required to travel through the column, was measured. Undiluted and 20% ethanol were used as controls. Ethanol was detected in both the *A. fumigatus* and *T. viride* samples as summarized below in Table 26.

TABLE 26

Detection of ethanol in the *A. fumigatus* and *T. viride* aqueous fermented layer.

| Sample | Ret Time (min) | Type | Width (min) | Area (pA * s) | Height (pA) | Area % |
|---|---|---|---|---|---|---|
| Control: undiluted ethanol | 1.187 | BB S | 0.0822 | 8.63217e5 | 1.76007e5 | 99.99667 |
| Control: 20% ethanol | 1.059 | BBAS | 0.0903 | 1.73049e5 | 2.87025e4 | 1.000e2 |
| *A. fumigatus* | 1.111 | BB | 0.0786 | 559.79517 | 91.18233 | 73.45245 |
| *T. viride* | 1.088 | BV | 0.0222 | 12.98238 | 8.81493 | 34.32508 |

Example 5

Simultaneous Saccharification and Fermentation in a Modified Fermentor

According to the methods described herein, a collectible biomass and filtrate were subjected to simultaneous saccharification and fermentation (SSF) in a modified fermentor in order to determine if the ethanol concentration increases over time and to further confirm that autolysis and fermentation occur simultaneously.

Eighteen flasks were washed and sterilized. Culture media was prepared containing 0.5 ml of glycerol, 0.05 grams of urea, and 0.1 grams of chlorine dioxide dissolved in 1000 ml of water. 200 ml of culture media was distributed to each flask. Well-chopped rice straw (5 grams) was added to each flask, where it soaked in the culture media for 10 minutes.

The flasks were then agitated for 5 minutes, following which the flasks were placed under UV lamps for 10 minutes. The flasks were then inoculated with spores; 9 flasks were inoculated with *Aspergillus fumigatus* spores, and 9 flasks were inoculated with *Trichoderma viride* spores. All flasks were incubated for 6 days at 29±1° C.

Figure 10:
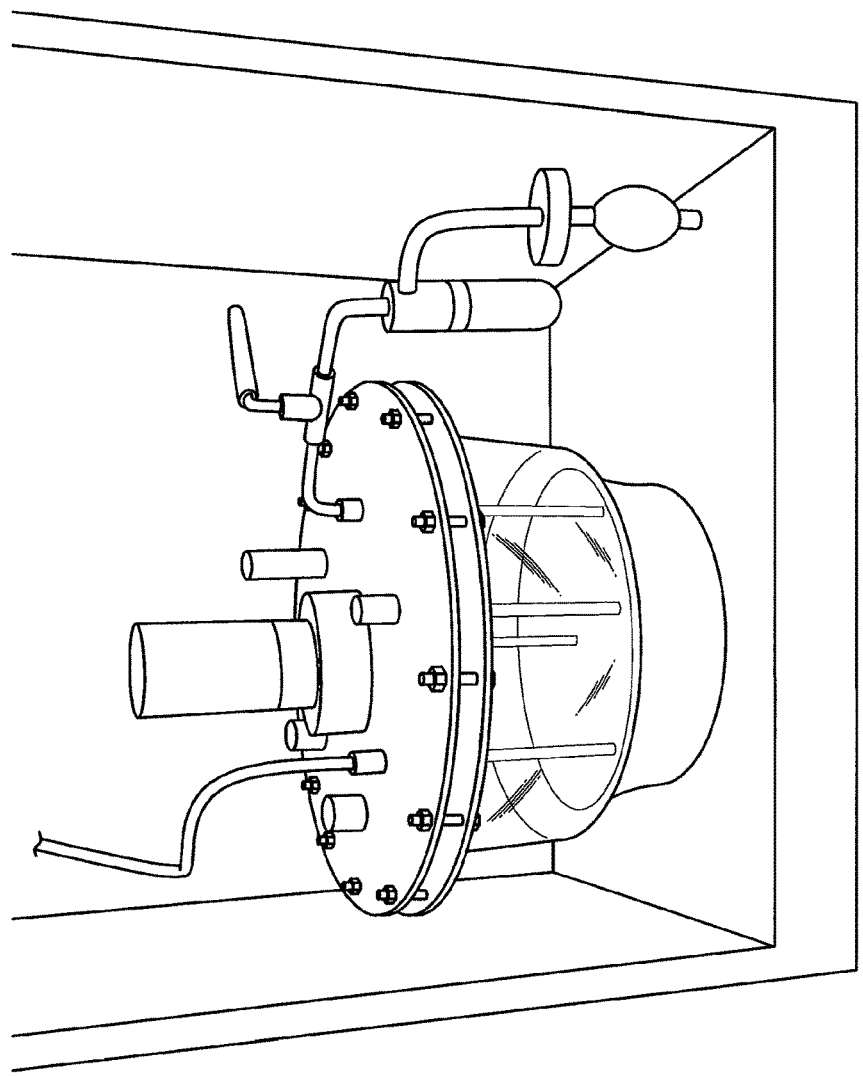
FIG. 10 shows one embodiment of an exemplary fermentor that may be used for any or all of the steps of autolysis, fermentation, separation and storage.

Following incubation, the fresh mycelia (i.e., the *A. fumigatus* and *T. viride* biomasses) were very well chopped together with a minor quantity of their respective filtrate and 0.5 grams of chlorine dioxide per liter of the total filtrate volume (200 ml×18). The chopped mycelia were then well-ground with an amount of hexane sufficient to dissolve the biocell lipids and to serve as a buffer between the environment and remaining autolysate, and the mixture was placed in a fermentor. The remaining filtrates were added with the rice straw to the prepared slurry in the sterilized fermentor (see FIG. 10). The fermentor holding the resulting suspension with the rice straw was aerated by bubbling filtered air for 15 minutes through the aeration tube. The open fermentor (i.e., the glass vessel without the stainless steel cover) was placed under UV light for 15 minutes, after which 1.5 ml of $H_2O_2$ (30% concentration) was added to each liter of suspension, and the container was left for one hour. After the one hour, the $H_2O_2$ was neutralized by adding 7.1 grams of sodium bicarbonate per liter of suspension.

Immediately after neutralization, the lower aqueous layer was inoculated with the yeast *Saccharomyces cerevisiae*. The covered and sealed fermentor was placed in an incubator at 30±1° C. Following inoculation with *S. cerevisiae*, the fermentor's stirrer was set at low speed (i.e., about 200 rpm) for the remainder of the process. In addition, a compressor applied pressure greater than the vapor pressure of hexane at 30° C. in order to prevent the hexane from evaporating. A 1.5 bar safety valve regulated the pressure inside the fermentor. The lower aqueous layer was supplied with filtered air through the aeration tube for about 24 hours. The air pump was stopped after 24 hours to initiate the anaerobic phase. In this manner, the biomass underwent autolysis and fermentation in the fermentor containing the aqueous and organic solvent layers that separate the bio-products based on solubility.

After 10 days, samples were taken from the lower aqueous layer to be analyzed for enzymatic activity. As shown below in Table 27, the surplus extracellular enzymes, such as cellulose and amylase present in the filtrate of Example 1 (see Table 6), were fully utilized in the present study to produce glucose from the substrate and autolysate. These results confirm that any extracellular enzymes present in the filtrate can be used to further hydrolyze the biomass and remaining substrate and generate more valuable products.

TABLE 27

Enzymatic Evaluation

| Enzyme | Activity |
| --- | --- |
| Cellulase | No activity |
| Amylase | No activity |
| Protease | Weak activity |
| Lipase | Weak activity |

Over a period of 10 days from the time the air pump was stopped, samples were taken every 48 hours from the lower aqueous layer via the sampling unit to be analyzed for ethanol concentration, total reducing sugars, pH, and total viable *S. cerevisiae* (Table 28). The presence and concentration of ethanol was detected using gas chromatography (GC). HP-5 capillary columns were used with (5%-phenyl)-methylpolysiloxane as the stationary phase and $N_2$ as the carrier gas in an Agilent 7890 GC (Agilent Technologies, Santa Clara, Calif.). The samples were heated to 250° C. for injection, and the detector was heated to 300° C. The retention time, i.e., the time required to travel through the column, was measured. In order to determine the concentration of ethanol in the samples, a standard curve was generated using ethanol solutions of 5%, 10%, 15%, 20% and 25% ethanol.

The pH of each sample was measured using a pH meter. The concentration of reducing sugars (e.g., glucose and fructose) was determined using a spectrophotometer. The number of viable *S. cerevisieae* in each sample was determined by plating serial dilutions of the sample and performing CFU counts.

TABLE 28

Analysis of the lower aqueous layer.

| Sample No. | Time point | pH | Total Reducing Sugar (mg/ml) | Yeast Count | Ethanol content (%) |
| --- | --- | --- | --- | --- | --- |
| 1 | 0 (aeration stopped) | 9.01 | 1377 | 490 | 0.25 |
| 2 | 48 h | 9.01 | 1049 | 160 | 1.6 |
| 3 | 96 h | 9.27 | 1054 | 60 | 1.4 |
| 4 | 144 h | 9.28 | 1023 | 30 | (no data) |
| 5 | 192 h | 9.32 | 1006 | 20 | 2.57 |
| 6 | 240 h | 9.55 | 952 | 10 | 3.9 |

These results demonstrate that over the course of 10 days in the fermentor under anaerobic conditions, the concentration of ethanol increased as expected. By 48 hours, the amount of reducing sugars present in the aqueous layer remained stable and decreased slightly over time. This finding confirms that autolysis, including saccharification, did occur simultaneously with fermentation.

Also note that the pH of the samples was increasingly alkaline. It is known that *S. cerevisiae* optimally produce ethanol in an acidic environment. Although the alkaline environment was killing the yeast, as indicated by the sharp decline in viable count, the yeast was striving to produce ethanol. The survival of the yeast in such an alkaline environment was attributed to the rich substrate, i.e., the autolysate and filtrate. Therefore, it is expected that the yeast will have a much greater ethanol yield in optimized conditions.

In order to determine the amount of various monosaccharides present in the aqueous layer of the autolysate after 10 days of anaerobic conditions in the fermentor, samples were analyzed by HPLC. The monosaccharide contents were quantified by HPLC 10A on a Shimaduzu Shim-Pack SCR-101N column (7.9 mm×30 cm) using deionized water as the mobile phase (flow rate 0.5 ml/min at 40° C.) and refractive index detection as described by Asker et al. (Carbohydrate Polymers, 77:563-567, 2009). The results are summarized below in Table 29. Notably, glucose was not detected in the samples. These findings indicate that all of the glucose present in the sample was utilized by the yeast in the generation of ethanol. Also, the xylose that was detected in the sample can either be utilized as a fermentation substrate to generate additional ethanol or hydrogenated to generate xylitol as described supra.

TABLE 29

HPLC analysis of the lower aqueous layer.
Time values are shown as minutes.

| Monosaccharide | Retention Time (RT) | mg/L |
|---|---|---|
| Glucouronic acid | 7.269 | 432.07 |
| Xylose | 12.282 | 69.15 |
| Arabinose | 15.823 | 13.401 |
| Ethanol | 17.094 | — |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Aspects of the embodiments can be modified, if necessary, to employ concepts of the various patents, applications and publications described herein to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of processing a microorganism biomass comprising:
    providing the microorganism biomass in an aqueous solution comprising uncontaminated fresh or purified water;
    treating the aqueous solution with chlorine dioxide to induce autolysis of the microorganism biomass, wherein the treating results in production of an autolysate of the microorganism biomass;
    aerating the aqueous solution after a suitable exposure time to the chlorine dioxide, wherein the aerating halts the adverse effect of the chlorine dioxide on the microorganism biomass autolysate; and
    providing a volume of an organic solvent to float on top of the aqueous solution, after said treating, wherein the volume of the organic solvent is sufficient to dissolve the lipids of the autolysate;
    wherein said providing the volume of the organic solvent causes the autolysate to separate into an upper layer comprising the organic solvent and the lipids; and a lower layer comprising the aqueous solution and non-lipid materials of the autolysate;
    wherein said upper layer protects said lower layer from environmental microbial contamination.

2. The method of claim 1, further comprising:
    contacting the lower layer comprising the aqueous solution with a microorganism capable of fermenting a fermentable sugar, wherein the lower layer further comprises a fermentable sugar;
    fermenting the fermentable sugar in the lower layer to produce an alcohol; and
    separately collecting at least a portion of one or both of the upper layer and the lower layer, wherein the fermenting occurs prior to the collecting.

3. A method of producing lipid materials, materials, or lipid and non-lipid materials comprising:
    providing an aqueous solution comprising a biodegradable substrate contaminated with a first microorganism biomass;
    treating the aqueous solution with chlorine dioxide, to induce autolysis of the first microorganism biomass and produce a first autolysate, and to sterilize the aqueous solution;
    aerating the aqueous solution after a suitable exposure time to the chlorine dioxide, wherein the aerating halts the adverse effect of the chlorine dioxide on the biodegradable substrate and the first autolysate;
    culturing a second microorganism on the biodegradable substrate, wherein the culturing produces a cultured microorganism biomass, and allows the cultured microorganism to produce a filtrate;
    optionally, harvesting the cultured microorganism biomass;
    treating the aqueous solution comprising the cultured microorganism biomass with chlorine dioxide, to induce autolysis of the cultured microorganism biomass and produce a second autolysate;
    aerating the aqueous solution after a suitable exposure time to chlorine dioxide to halt the adverse effect of chlorine dioxide on the second autolysate;
    providing an organic solvent to float on top of the aqueous solution after the autolysis of the second microorganism is induced, wherein the organic solvent dissolves lipids released from the cultured microorganism biomass during said autolysis, and lipid materials present in the filtrate;
    wherein said providing the organic solvent causes materials that were present in the aqueous solution to separate into an upper layer comprising: the organic solvent, the lipids released from the cultured microorganism biomass during said autolysis, and the lipid materials present in the filtrate; and a lower layer comprising: the aqueous solution, non-lipid materials released from the cultured microorganism biomass during said autolysis, and non-lipid materials present in the filtrate;
    wherein said upper layer protects said lower layer comprising the aqueous solution from environmental microbial contamination; and
    separately collecting at least: a portion of the upper layer, thereby producing lipid materials; a portion of the lower layer, thereby producing non-lipid materials; or portions of both the upper layer and the lower layer, thereby producing both lipid materials and non-lipid materials.

4. The method according to claim 1, wherein the microorganism is a fungus, a bacterium, an algae, or a protist.

5. The method according to claim 3, wherein the biodegradable substrate is a solid substrate, a liquid substrate, or an autolysate remnant from a prior microorganism biomass.

6. The method according to claim 3, further comprising a step of optimizing the physiochemical conditions for said culturing.

7. The method according to claim 3, wherein said harvesting comprises mechanically collecting the cultured microorganism biomass or collecting a liquid solution comprising the cultured microorganism biomass.

8. The method according to claim 1, further comprising a step of isolating at least a portion of the lipids from the upper layer.

9. The method according to claim 8, further comprising producing biofuel or biodiesel from the lipids.

10. The method according to claim 1, wherein the lower layer comprises glucose, a fermentable sugar, an amino acid, an organic acid, an inorganic acid, a polyhydric alcohol, a nitrogenous compound, an enzyme, or a vitamin.

11. The method according to claim 10, further comprising producing hydrogen or carbon dioxide from the glucose.

12. The method according to claim 10, further comprising fermenting the fermentable sugar to produce an alcohol or an acid.

13. The method according to claim 1, further comprising a step of isolating at least a portion of the non-lipid materials.

14. The method according to claim 3, wherein a gas is provided during said culturing.

* * * * *